United States Patent
Gregson et al.

[11] Patent Number: 5,889,178
[45] Date of Patent: Mar. 30, 1999

[54] 2-6-DIAMINOPURINE PRECURSORS

[75] Inventors: Michael Gregson, Stevenage; Barry Edward Ayres, deceased, late of Hitchin, by Diane Sally Ayres, executor; George Blanch Ewan; Frank Ellis, both of Stevenage; John Knight, Arlesey, all of Great Britain

[73] Assignee: Glaxo Group Limited, Middlesex, Great Britain

[21] Appl. No.: 934,540

[22] Filed: Sep. 22, 1997

Related U.S. Application Data

[62] Division of Ser. No. 446,727, filed as PCT/EP94/00145 Jan. 18, 1994.

[30] Foreign Application Priority Data

Jan. 20, 1993 [GB] United Kingdom .................. 93 01000

[51] Int. Cl.⁶ .................................................. C07H 19/00
[52] U.S. Cl. ......................................................... 536/27.22
[58] Field of Search ............................... 536/28.9; 514/43

[56] References Cited

U.S. PATENT DOCUMENTS

| | | | |
|---|---|---|---|
| 3,983,104 | 9/1976 | Vorbruggen | 536/27.61 |
| 4,663,313 | 5/1987 | Bristol et al. | 514/46 |
| 4,704,381 | 11/1987 | Schaumann et al. | 514/46 |
| 4,757,747 | 7/1988 | Hamilton et al. | 514/46 |
| 4,968,697 | 11/1990 | Hutchison | 514/46 |
| 4,985,409 | 1/1991 | Yamada et al. | 514/46 |
| 5,043,325 | 8/1991 | Olsson et al. | 514/46 |
| 5,106,837 | 4/1992 | Carson et al. | 514/46 |
| 5,219,839 | 6/1993 | Bru-Magniez et al. | 514/46 |
| 5,219,840 | 6/1993 | Gadient et al. | 514/46 |
| 5,446,139 | 8/1995 | Seela et al. | 536/26.7 |
| 5,459,255 | 10/1995 | Cook et al. | 536/27.13 |

FOREIGN PATENT DOCUMENTS

| | | |
|---|---|---|
| A-139358 | 5/1985 | European Pat. Off. . |
| A-0 222 330 | 5/1987 | European Pat. Off. . |
| A-0 277 917 | 8/1988 | European Pat. Off. . |
| 0423777 | 4/1991 | European Pat. Off. . |
| A-0 423 777 | 4/1991 | European Pat. Off. . |
| A-2203149 | 10/1988 | United Kingdom . |
| WO88/03148 | 5/1988 | WIPO . |
| WO-A-89 08658 | 9/1989 | WIPO . |
| WO-A-92 03463 | 3/1992 | WIPO . |
| WO95/02604 | 1/1995 | WIPO . |

OTHER PUBLICATIONS

Goodman, "Chemical Syntheses and Transformations of Nucleosides," Chapter 2 in *Basic Principles in Nucleic Acid Chemistry*, vol. 1, P.O.P.Ts'o (ed.), Academic Press, New York, NY, 1974, pp. 94–208, only pp. 94, 154, 159–160 and 203–204 supplied.

Hutchison et al., Journal of Medicinal Chemistry, vol. 33, No. 7, Jul. 1990, 1919–1924.

*Primary Examiner*—Marian C. Knode
*Assistant Examiner*—L. Eric Crane
*Attorney, Agent, or Firm*—Bacon & Thomas, PLLC

[57] ABSTRACT

The present invention relates to compounds of formula (IV):

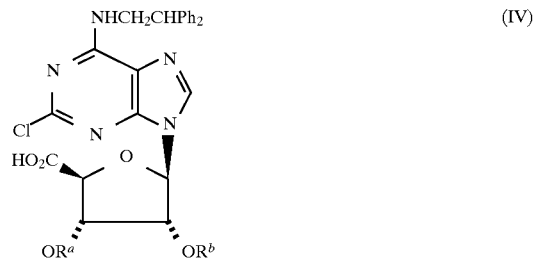

wherein $R^a$ and $R^b$ each represent a hydrogen atom or together form an alkylidene group.

3 Claims, No Drawings

2-6-DIAMINOPURINE PRECURSORS

This application is a Division of application Ser. No. 08/446,727, filed Sep. 18, 1995, now allowed, which is a 371 of International Application PCT/EP94/00145, filed Jan. 18, 1994.

The present invention relates to therapeutically active 2,6-diaminopurine-β-D-ribofuranuronamide derivatives, processes for the manufacture of said compounds, pharmaceutical formulations containing said compounds and the use of said compounds in chemotherapy. In particular, we have found a group of novel compounds which are effective in treating inflammatory diseases.

Inflammation is a primary response to tissue injury or microbial invasion and is characterised by circulating leukocytes binding to and extravasion through vascular endothelium. Circulating leukocytes include neutrophils, eosinophils, basophils, monocytes and lymphocytes. Different forms of inflammation involve different types of infiltrating leukocytes, the particular profile being regulated by gene expression in vascular endothelium in response to a variety of inflammatory mediators.

The primary function of leukocytes is to defend the host from invading organisms such as bacteria and parasites. Once a tissue is injured or infected a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment and resolution are not adequately controlled and the inflammatory reaction causes tissue destruction.

We have now found a novel group of compounds with broad anti-inflammatory properties which inhibit leukocyte recruitment and activation. The compounds are therefore of potential therapeutic benefit in providing protection from leukocyte-induced tissue damage in diseases where leukocytes are implicated at the site of inflammation. The compounds of the invention may also represent a safer alternative to corticosteroids in the treatment of inflammatory diseases, whose uses are severely limited by their side-effect profiles.

Thus, according to one aspect of this invention, we provide a compound of general formula (I)

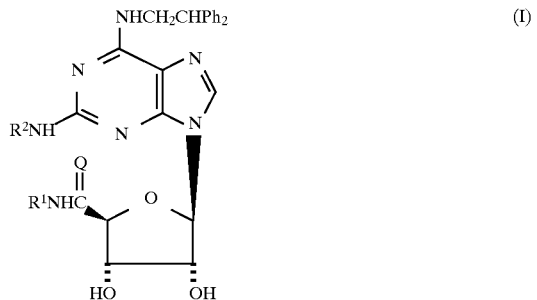

and salts and solvates thereof, wherein:
$R^1$ represents a hydrogen atom or a $(C_{3-8})$cycloalkyl or $(C_{1-6})$alkyl group;
$R^2$ represents a group selected from
(i) $(C_{3-8})$cycloalkyl
(ii) $(C_{3-8})$cycloalkyl substituted by one or more groups (e.g. 1, 2 or 3 groups) which may be the same or different and are selected from $C_{2-7}$acylamino, guanidino, carboxyl, oxo and $(CH_2)pR^3$ (where p is zero or 1 and $R^3$ is hydroxy, $NH_2$, $(C_{1-6})$alkylamino or di$(C_{1-6})$alkylamino)
(iii) pyrrolidinyl-3-yl, 2-oxopyrrolidin-4-yl, 2-oxopyrrolidin-5-yl, piperidinyl-3-yl or piperidin-4-yl in which the ring nitrogen atom is substituted by hydrogen, $(C_{1-6})$alkyl or aryl$(C_{1-6})$alkyl (e.g. benzyl)
iv) pyrrolidin-3-yl, -piperidin-3-yl or piperidin-4-yl in which the ring nitrogen atom is substituted by hydrogen, $(C_{1-6})$alkyl or aryl$(C_{1-6})$alkyl (e.g. benzyl) and one or more of the ring carbon atoms (e.g. 1, 2 or 3 ring carbon atoms) is substituted by the same or different groups selected from $(C_{2-7})$acylamino, guanidino, oxo and $(CH_2)pR^3$ (where p and $R^3$ are as defined previously)
(v) $(C_{3-8})$cycloalkyl $(C_{1-6})$alkyl
(vi) $(C_{3-8})$cycloalkyl$(C_{1-6})$alkyl in which one or more of the ring carbon atoms (e.g. 1, 2 or 3 ring carbon atoms) is substituted by the same or different groups selected from $(C_{2-7})$acylamino, guanidino, carboxyl, oxo and $(CH_2)pR^3$ (where p and $R^3$ are as defined previously)
(vii) —$Alk_1Y$ where $Alk_1$ is a $(C_{2-6})$alkylene group and Y is a group selected from $(C_{2-7})$acylamino, guanidino, hydroxyl, $NH_2$, $(C_{1-6})$alkylamino, di$(C_{1-6})$alkylamino or

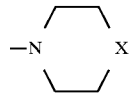

(where X is a bond, O, $CH_2$ or $NR^4$ in which $R^4$ is hydrogen, $(C_{1-6})$alkyl or aryl$(C_{1-6})$alkyl) and
(viii) —$(CHR^5)_m(Alk_2)_nZ$ where m and n each independently represent zero or 1 except that when m is 1 then n must also represent 1, $R^5$ is a hydrogen atom or a carboxy group or a group $CH_2R^6$ (where $R^6$ is $(C_{2-7})$acylamino, guanidino, hydroxy, methoxy, $NH_2$, $(C_{1-6})$alkylamino or di$(C_{1-6})$alkylamino), $Alk_2$ is a $(C_{1-5})$alkylidene group and Z is a hydrogen atom or an optionally substituted aromatic ring selected from phenyl, pyridyl, pyrimidinyl, imidazolyl, triazolyl, tetrazolyl and benzimidazolyl where the ring is optionally substituted by one or more groups (e.g. 1, 2 or 3 groups) which may be the same or different and are selected from $(C_{1-6})$alkyl, $(C_{2-7})$ acylamino, guanidino, carboxyethyl, hydroxy, $NH_2$, $(C_{1-6})$alkylamino or di$(C_{1-6})$alkylamino;

Q represents an oxygen or sulphur atom; and
Ph represents phenyl.

Suitable salts of the compounds of formula (I) include physiologically acceptable salts such as acid addition salts derived from inorganic or organic acids, for example hydrochlorides, hydrobromides, sulphates, phosphates, acetates, benzoates, citrates, succinates, lactates, tartrates, fumarates and maleates, and, if appropriate, inorganic base salts such as alkali metal salts, for example sodium salts. Other salts of the compounds of formula (I) include salts which are not physiologically acceptable but may be useful in the preparation of compounds of formula (I) and physiologically acceptable salts thereof. Examples of such salts include trifluoroacetates.

Examples of suitable solvates of the compounds of formula (I) include hydrates.

It will be appreciated that when $R^2$ in compounds of formula (I) contains one or more asymmetric carbon atoms the invention includes all diastereoisomers of compounds of formula (I) and mixtures thereof. Otherwise, the stereochemical configuration of compounds of the invention is as depicted in formula (I) above.

It is to be understood that all tautomeric forms of the compounds of formula (I) are included within the scope of this invention.

The cycloalkyl group within $R^1$ or $R^2$ may be a monocyclic or bridged cyclic ring. Particular examples of suitable cycloalkyl ring systems include $(C_{3-8})$monocyclic cycloalkyl groups, such as cyclopropyl, cyclopentyl and cyclohexyl. Within $R^2$ the $(C_{3-8})$cycloalkyl group may particularly represent cyclopentyl or cyclohexyl.

The term 'aryl' as part of an aryl$(C_{1-6})$alkyl group may represent, for example, a phenyl group optionally substituted by one or more substituents (e.g. 1, 2 or 3 substituents) which may be the same or different and are selected from halogen, hydroxyl, $(C_{1-3})$alkoxy and $(C_{1-3})$alkyl.

The term 'alkyl' as a group or part of a group means a straight or branched chain alkyl group. Particular examples of suitable alkyl groups include methyl, ethyl, n-propyl, i-propyl, n-butyl, s-butyl and t-butyl.

The term 'alkylene' as part of a group means a straight or branched alkylene chain. Particular examples of suitable alkylene chains include —CH$_2$—, —CH$_2$CH$_2$—, —CH$_2$CH$_2$CH$_2$—, —CHCH$_3$CH$_2$— and —CH$_2$C(CH$_3$)$_2$CH$_2$—.

When $R^2$ represents a group —Alk$_1$Y the $(C_{2-6})$alkylene group may particularly represent —CH$_2$CH$_2$—, —CH$_2$CH$_2$CH$_2$— or —CH$_2$C(CH$_3$)$_2$CH$_2$—.

When $R^2$ represents a group —(CHR$^5$)$_m$(Alk$_2$)$_n$Z the chain —(CHR$^5$)$_m$(Alk$_2$)$_n$— may particularly represent a bond, —CH$_2$—, —CH$_2$CH$_2$—, —CHR$^5$CHCH$_3$CH$_2$— or —CHR$^5$CH$_2$— (where R$^5$ is a group CH$_2$R$^6$ and R$^6$ is as defined previously).

The term '$(C_{2-7})$acylamino' within $R^2$ means a $(C_{2-7})$ alkanoylamino group wherein the $(C_{1-6})$alkyl portion thereof is a straight or branched alkyl group as previously defined and may be optionally substituted by one or more halogen atoms such as fluorine. Examples of suitable $(C_{2-7})$ alkanoylamino groups within $R^2$ include acetamido and trifluoroacetamido.

Within Z, the term 'pyridyl' means a 2-, 3- or 4-pyridyl group; the term 'pyrimidinyl' means a 2-, 4 or 5-pyrimidinyl group; the term 'imidazolyl' means a 1-, 2-, 4- or 5-imidazolyl group; and the term 'triazolyl' means a 1,2,4-triazolyl group (e.g. 1,2,4-triazol-1-yl or 1,2,4-triazol-3-yl).

$R^1$ preferably represents a $(C_{1-3})$alkyl group, especially ethyl.

Compounds of formula (I) in which Q represents an oxygen atom are generally preferred.

Compounds of formula (I) in which $R^1$NHC(=Q)— represents ethylaminocarbonyl are particularly preferred.

A preferred group of compounds of the invention are compounds of formula (I) in which $R^2$ represents a substituted cyclopentyl or cyclohexyl group wherein the ring is substituted by one or two groups, especially one or two groups selected from hydroxy, NH$_2$, methylamino, dimethylamino, acetamido or trifluoroacetamido. Preferred substituents include hydroxy, dihydroxy, NH$_2$ and dimethylamino.

A further preferred group of compounds of the invention are compounds of formula (I) in which $R^2$ represents a pyrrolidin-3-yl or piperidin-3-yl group in which the ring nitrogen atom is substituted by hydrogen, $(C_{1-3})$alkyl (e.g. ethyl) or benzyl.

Another preferred group of compounds of the invention are compounds of formula (I) in which $R^2$ represents (CHR$^5$)$_m$(Alk$_2$)$_n$Z where R$^5$, m and n are as defined previously and Z is an optionally substituted imidazolyl group. Particularly preferred are those compounds in which —(CH$_2$R$^5$)$_m$(Alk$_2$)$_n$— represents —CH$_2$CH$_2$—.

It is to be understood that the present invention covers all combinations of particular and preferred groups referred to hereinabove.

Specific compounds of the present invention include:

(1S-trans)-1-deoxy-1-[6-[(2,2-diphenylethyl)amino]-2-[(3-hydroxycyclopentyl)amino]-9H-purin-9-yl]-N-ethyl-β-D-ribofuranuronamide;

(1R-trans)-1-deoxy-1-[6-[(2,2-diphenylethyl)amino]-2-[(3-hydroxycyclopentyl)amino]-9H-purin-9-yl]-N-ethyl-β-D-ribofuranuronamide;

[1S-(1α,2β,3β)]-1-deoxy-1-[2-[(2,3-dihydroxycyclopentyl)amino]-6-[(2,2-diphenylethyl)amino]-9H-purin-9-yl]-N-ethyl-β-D-ribofuranuronamide;

[cis-(±)]-1-[2-[(3-aminocyclopentyl)amino]-6-[(2,2-diphenylethyl)amino]]-9H-purin-9-yl]-1-deoxy-N-ethyl-β-D-ribofuranuronamide;

(trans)-1-[2-[(2-aminocyclopentyl)amino]-6-[(2,2-diphenylethyl)amino]]-9H-purin-9-yl]-1-deoxy-N-ethyl-β-D-ribofuranuronamide, isomer 1;

(1S-trans)-1-[2-[(3-aminocyclopentyl)amino]-6-[(2,2-diphenylethyl)amino]]-9H-purin-9-yl]-1-deoxy-N-ethyl-β-D-ribofuranuronamide;

[(1R-trans)]-1-[2-[(3-aminocyclopentyl)amino]-6-[(2,2-diphenylethyl)amino]]-9H-purin-9-yl]-1-deoxy-N-ethyl-β-D-ribofuranuronamide;

[trans-(±)]-1-deoxy-1-[6-[(2,2diphenylethyl)amino]-2-[[3-[(trifluoroacetyl)amino]cyclopentyl]amino]-N-ethyl-9H-purin-9-yl]-β-D-ribofuranuronamide;

1-deoxy-1-[6-[(2,2-diphenylethyl)amino]-2-[[2-(1H-imidazol-4-yl)ethyl]amino]-9H-purin-9-yl]-N-ethyl-β-D-ribofuranuronamide;

(1S)-1-deoxy-1-[6-[(2,2-diphenylethyl)amino]-2-[[1-(hydroxymethyl)-2-phenylethyl]amino]-9H-purin-9-yl]-N-ethyl-β-D-ribofuranuronamide;

(trans)-1-deoxy-1-[6-[(2,2diphenylethyl)amino]-2-(4-hydroxycyclohexyl)amino]-9H-purin-9-yl]-N-ethyl-β-D-ribofuranuronamide;

(cis)-1-deoxy-1-[6-[(2,2-diphenylethyl)amino]-2-[(4-hydroxycyclohexyl)amino]-9H-purin-9-yl]-N-ethyl-β-D-ribofuranuronamide;

1-deoxy-N-ethyl-1-[2-[(3-hydroxypropyl)amino]-6-[(2,2-diphenylethyl)amino]-9H-purin-9-yl]-β-D-ribofuranuronamide;

1-[2-[(4-aminophenyl)amino]-6-[(2,2-diphenylethyl)amino]]-9H-purin-9-yl]-1-deoxy-N-ethyl-β-D-ribofuranuronamide;

1-deoxy-1-[2-[[4-(dimethylamino)phenyl]amino]-6-[(2,2-diphenylethyl)amino]]-9H-purin-9-yl]-N-ethyl-β-ribofuranuronamide;

(1α,2β,5β)-1-deoxy-1-[2-[[2,5-dihydroxycyclopentyl]amino]-6-[(2,2-diphenylethyl)amino]]-9H-purin-9-yl]-N-ethyl-β-ribofuranuronamide;

[trans-(±)]-1-deoxy-1-[6-[(2,2-diphenylethyl)amino]-2-(4-hydroxy-3-pyrrolidinyl)amino]-9H-purin-9-yl]-ethyl-β-D-ribofuranuronamide;

(±)-1-deoxy-1-[6-[(2,2-diphenylethyl)amino]-2-[(N-ethylpiperidin-3-yl)amino]-9H-purin-9-yl]-N-ethyl-β-D-ribofuranuronamide;

1-deoxy-1-[6-[(2,2-diphenylethyl)amino]-2-[[2-(1-piperidinyl)ethyl]amino]-9H-purin-9-yl]-N-ethyl-β-D-ribofuranuronamide;

1-deoxy-1-[6-[(2,2-diphenylethyl)amino]-2-[[2-(4morpholinyl)ethyl]amino]-9H-purin-9-yl]-N-ethyl-β-D-ribofuranuronamide;

1-deoxy-1-[6-[(2,2-diphenylethyl)amino]-2-[[-2-(2-pyridinyl)ethyl]amino]-9H-purin-9-yl]-N-ethyl-β-D-ribofuranuronamide;

1-deoxy-1-[6-[(2,2-diphenylethyl)amino]-2-[[2-(pyrrolidin-1-yl)ethyl]amino]-9H-purin-9-yl]-N-ethyl-β-D-ribofuranuronamide;

(1S)-1-deoxy-1-[6-[(2,2-diphenylethyl)amino]-2-[[1-(hydroxymethyl)-2-(3-pyridinyl)ethyl]amino]-9H-purin-9-yl]-N-ethyl-β-D-ribofuranuronamide;

(1S)-1-deoxy-1-[6-[(2,2-diphenylethyl)amino]-2-[[1-(hydroxymethyl)-2-(methyl)propyl]amino]-9H-purin-9-yl]-N-ethyl-β-D-ribofuranuronamide;

[cis-(±)]-1-deoxy-1-[6-[(2,2-diphenylethyl)amino]-2-[(3-hydroxycyclopentyl)amino]-9H-purin-9-yl]-N-ethyl-β-D-ribofuranuronamide;

1-deoxy-1-[2-[[2-(N,N-dimethylamino)ethyl]amino]-6-[(2,2-diphenylethyl)amino]-9H-purin-9-yl]-N-ethyl-β-D-ribofuranuronamide;

1-deoxy-1-[2-[[3-(N,N-dimethylamino)propyl]amino]-6-[(2,2-diphenylethyl)amino]-9H-purin-9-yl]-N-ethyl-β-D-ribofuranuronamide;

(1α,3β,4β)-1-deoxy-1-[2-[(3,4-dihydroxycyclopentyl)amino]-6-[(2,2-diphenylethyl)amino]]-9H-purin-9-yl]-ethyl-β-D-ribofuranuronamide;

[(1S)-trans]-1-deoxy-1-[2-[(3-N,N-dimethylamino)cyclopentylamino]-6-[(2,2-diphenylethyl)amino]-9H-purin-9-yl]-N-ethyl-β-D-ribofuranuronamide;

(3S)-1-deoxy-1-[6-[(2,2-diphenylethyl)amino]-2-[(3-pyrrolidinyl)amino]-9H-purin-9-yl]-N-ethyl-β-D-ribofuranuronamide;

(3R)-1-deoxy-1-[6-[(2,2-diphenylethyl)amino]-2-[(3-pyrrolidinyl)amino]-9H-purin-9-yl]N-ethyl-β-D-ribofuranuronamide;

(3R)-1-deoxy-1-[6-[(2,2-diphenylethyl)amino]-2-[[1-(phenylmethyl)-3-pyrrolidinyl]amino]-9H-purin-9-yl]-ethyl-β-D-ribofuranuronamide;

(±)-1-deoxy-1-[6-[(2,2-diphenylethyl)amino]-2-[(1-ethyl-3-pyrrolidinyl)amino]-9H-purin-9-yl]-ethyl-β-D-ribofuranuronamide;

1-deoxy-1-[6-[(2,2diphenylethyl)amino]-2-[(1-ethyl-4-piperidinyl)amino]-9H-purin-9-yl]-N-ethyl-β-D-ribofuranuronamide;

(trans)-1-[2-[(4-aminocyclohexyl)amino]-6-[(2,2-diphenylethyl)amino]-9H-purin-9-yl]-1-deoxy-N-ethyl-β-D-ribofuranuronamide;

[(1α,2β,3β)-(±)]-1-[2-[(3-acetylamino-2-hydroxycyclopentyl)amino]-6-[(2,2-diphenylethyl)amino]-9H-purin-9-yl]-1-deoxy-N-ethyl-β-D-ribofuranuronamide;

(1R-trans)-1-deoxy-1-[6-[(2,2-diphenylethyl)amino]-2-[(2-hydroxycyclopentyl)amino]-9H-purin-9-yl]-N-ethyl-β-D-ribofuranuronamide;

1-deoxy-1-[6-[(2,2-diphenylethyl)amino]-2-[[2-(1-methyl-1H-imidazol-4-yl)ethyl]amino]-N-ethyl-9-H-purin-9-yl]-β-D-ribofuranuronamide;

1-deoxy-1-[6-[(2,2-diphenylethyl)amino]-2-[[2-(1H-imidazol-2-yl)ethyl]amino]-9H-purin-9-yl]-N-ethyl-β-D-ribofuranuronamide;

1-deoxy-1-[6-[(2,2-diphenylethyl)amino]-2-[[3-(1H-imidazol-4-yl)propyl]amino]-9H-purin-9yl]-N-ethyl-β-D-ribofuranuronamide;

1-deoxy-1-[6-[(2,2-diphenylethyl)amino]-2-[[(2-(1H-1,2,4-triazol-3-yl)ethyl]amino]-9H-purin-9-yl]-N-ethyl-β-D-ribofuranuronamide;

(trans)-1-deoxy-1-[2-[(4-N,N-dimethylaminocyclohexyl)amino]6-[(2,2-diphenylethyl)amino]-9H-purin-9-yl]-N-ethyl-β-D-ribofuranuronamide;

1-deoxy-1-[6-[(2,2-diphenylethyl)amino]-2-[[2-(2-methyl-1H-imidazol-4-yl)ethyl]amino]-9H-purin-9-yl]-N-ethyl-β-D-ribofuranuronamide;

1-deoxy-1-[2-[[2-[(aminoiminomethyl)amino]ethyl]amino]-6-[(2,2-diphenylethyl)amino]-9H-purin-9-yl]-N-ethyl-β-D-ribofuranuronamide;

1-deoxy-1-2-[[3-[(aminoiminomethyl)amino]propyl]amino]-6-[(2,2-diphenylethyl)amino]-9H-purin-9-yl]-N-ethyl-β-D-ribofuranuronamide;

1-[2-[[(6-amino-2-pyridinyl)methyl]amino]-6-[(2,2-diphenylethyl)amino]-9H-purin-9-yl]-1-deoxy-N-ethyl-β-D-ribofuranuronamide;

and physiologically acceptable salts and solvates thereof.

Particular compounds of the present invention include:

(1S-trans)-1-deoxy-1-[6-[(2,2-diphenylethyl)amino]-2-[(3-hydroxycyclopentyl)amino]-9H-purin-9-yl]-N-ethyl-β-D-ribofuranuronamide;

[1S-(1α,2β,3β)]-1-deoxy-1-[2-[(2,3-dihydroxycyclopentyl)amino]-6-[(2,2-diphenylethyl)amino]-9H-purin-9-yl]-N-ethyl-β-D-ribofuranuronamide;

[(1S)-trans]-1-deoxy-1-[2-[(3-N,N-dimethylamino)cyclopentylamino]-6-[(2,2-diphenylethyl)amino]-9H-purin-9-yl]-N-ethyl-β-D-ribofuranuronamide;

(3S)-1-deoxy-1-[6-[(2,2-diphenylethyl)amino]-2-[(3-pyrrolidinyl)amino]-9H-purin-9-yl]-N-ethyl-β-D-ribofuranuronamide;

(trans)-1-[2-[(4-aminocyclohexyl)amino]-6-[(2,2-diphenylethyl)amino]-9H-purin-9-yl]-deoxy-N-ethyl-β-D-ribofuranuronamide;

1-deoxy-1-[6-[(2,2-diphenylethyl)amino]-2-[[2-(1-methyl-1H-imidazol-4-yl)ethyl]amino]-N-ethyl-9H-purin-9-yl]-β-D-ribofuranuronamide;

(trans)-1-deoxy-1-[2-[(4-N,N-dimethylaminocyclohexyl)amino]6-[(2,2-diphenylethyl)amino]-9H-purin-9-yl]-N-ethyl-β-D-ribofuranuronamide;

1-deoxy-1-[6-[(2,2-diphenylethyl)amino]-2-[[2-(2-methyl-1H-imidazol-4-yl)ethyl]amino]-9H-purin-9-yl]-N-ethyl-β-D-ribofuranuronamide;

and physiologically acceptable salts and solvates thereof.

A particularly preferred compound of formula (I) is:

(trans)-1-[2-[(4-aminocyclohexyl)amino]-6-[(2,2diphenylethyl)amino]-9H-purin-9-yl]-1-deoxy-N-ethyl-β-D-ribofuranuronamide;

and physiologically acceptable salts and solvates thereof, including the hydrochloride salt.

The potential for compounds of formula (I) to inhibit leukocyte function may be demonstrated, for example, by their ability to inhibit superoxide ($O_2^-$) generation from neutrophils stimulated with chemoattractants such as N-formylmethionyl-leucyl-phenylalanine (fMLP). Accordingly, compounds of formula (I) are of potential therapeutic benefit in providing protection from leukocyte-induced tissue damage in diseases where leukocytes are implicated at the site of inflammation.

Examples of disease states in which the compounds of the invention have potentially beneficial anti-inflammatory effects include diseases of the respiratory tract such as adult respiratory distress syndrome (ARDS), bronchitis (including chronic bronchitis), cystic fibrosis, asthma (including allergen-induced asthmatic reactions), emphysema, rhinitis and septic shock. Other relevant disease states include diseases of the gastrointestinal tract such as intestinal inflammatory diseases including inflammatory bowel disease (e.g. Crohn's disease or ulcerative colitis), *Helicobacter-pylori* induced gastritis and intestinal inflammatory diseases secondary to radiation exposure or allergen exposure, and non-steroidal anti-inflammatory drug-induced gastropathy. Furthermore, compounds of the invention may be used to treat skin diseases such as psoriasis, allergic dermatitis and hypersensitivity reactions.

Further examples of disease states in which compounds of the invention have potentially beneficial effects include cardiac conditions such as peripheral vascular disease, post-ischaemic reperfusion injury and idiopathic hypereosinophilic syndrome.

Compounds of the invention which inhibit lymphocyte function also have use in the treatment of auto-immune diseases such as rheumatoid arthritis and diabetes.

Compounds of the invention may also be useful in inhibiting metastasis.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory agents.

There is thus provided as a further aspect of the invention a compound of formula (I) or a physiologically acceptable salt or solvate thereof for use in human or veterinary medicine, particularly in the treatment of patients with inflammatory conditions who are susceptible to leukocyte-induced tissue damage.

According to another aspect of the invention, there is provided the use of a compound of formula (I) or a physiologically acceptable salt or solvate thereof for the manufacture of a medicament for the treatment of patients with inflammatory conditions who are susceptible to leukocyte-induced tissue damage.

In a further or alternative aspect there is provided a method for the treatment of a human or animal subject with an inflammatory condition who is susceptible to leukocyte-induced tissue damage, which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in anti-inflammatory therapy, comprising a compound of formula (I) or a physiologically acceptable salt or solvate thereof together, if desirable, with one or more physiologically acceptable carriers or excipients.

The compounds according to the invention may, for example, be formulated for oral, buccal, parenteral, topical or rectal administration, preferably for parenteral or topical (e.g. by aerosol) administration.

Tablets and capsules for oral administration may contain conventional excipients such as binding agents, for example syrup, acacia, gelatin, sorbitol, tragacanth; mucilage of starch, cellulose or polyvinyl pyrrolidone, fillers, for example, lactose, microcrystalline cellulose, sugar, maize, starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan monooleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insulator, solutions for nebulisation or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetra-fluoroethane, 1,1,1,2,3,3,3-heptafluoropropane, 1,1,1,2-tetrafluorethane, carbon dioxide or other suitable gas.

Intranasal sprays may be formulated with aqueous or non-aqueous vehicles with the addition of agents such as thickening agents, buffer salts or acid or alkali to adjust the pH, isotonicity adjusting agents or anti-oxidants.

Capsules and cartridges of for example gelatin, or blisters of for example laminated aluminium foil, for use in an inhaler or insufflator may be formulated containing a powder mix of a compound of the invention and a suitable powder base such as lactose or starch.

Solutions for inhalation by nebulation may be formulated with an aqueous vehicle with the addition of agents such as acid or alkali, buffer salts, isotonicity adjusting agents or antimicrobials. They may be sterilised by fission or heating in an autoclave, or presented as a non-sterile-product.

The pharmaceutical compositions according to the invention may also be used in combination with other therapeutic agents, for example anti-inflammatory agents such as corticosteroids or NSAIDs.

The invention thus provides, in a further aspect a combination comprising a compound of formula (I) or a physiologically acceptable salt or solvate thereof together with another therapeutically active agent, for example an anti-inflammatory agent such as a corticosteroid or NSAID.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

Compounds of the invention may conveniently be administered in amounts of, for example, 0.01 to 500 mg/kg body weight, preferably 0.01 to 100 mg/kg body weight, 1 to 4 times daily. The precise dose will of course depend on the age and condition of the patient and the particular route of administration chosen.

The compounds of formula (I) and salts and solvates thereof may be prepared by the methodology described hereinafter, constituting a further aspect of this invention. In the following procedures, the groups $R^1$, $R^2$ and Q are as defined for compounds of formula (I) unless otherwise stated.

Thus, according to first process (A), a compound of formula (I) may be prepared by treating a compound of formula (II)

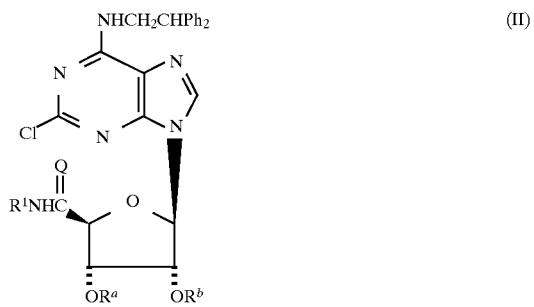

(wherein $R^a$ and $R^b$ each represent a hydrogen atom or together form an alkylidene group such as isopropylidene) with an amine $R^{2a}NH_2$ (wherein $R^{2a}$ is a group $R^2$ or is a protected derivative thereof), followed, where necessary, by the removal of any protecting groups present.

The displacement reaction to introduce the amine moiety may be carried out by heating the reagents at a temperature in the range of 50° to 150° C. optionally in the presence of a solvent such as dimethylsulphoxide.

A compound of formula (II) in which Q represents a sulphur atom may be prepared from a compound of formula (II) in which Q represents an oxygen atom and $R^a$ and $R^b$ together form an alkylidene group such as isopropylidene by thianation followed, if appropriate, by the removal of the alkylidene group.

The thianation reaction may be conveniently effected using known thianation agents such as hydrogen sulphide, phosphorus pentasulphide or Lawesson's reagent (p-methoxyphenylthiophosphine sulphide dimer). The reaction may be carried out in a known manner. For example when hydrogen sulphide is used an acid such as hydrochloric acid may conveniently be added in catalytic amounts and the reaction carried out in a polar solvent such as acetic acid or ethanol. When using Lawesson's reagent, the reaction may conveniently be carried out in a dry solvent such as toluene or methylene chloride.

A compound of formula (II) in which Q represents an oxygen atom may be prepared by treating a compound of formula (III)

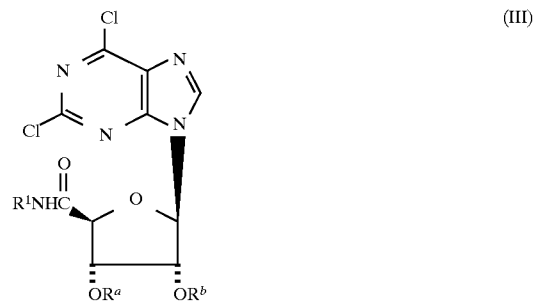

(wherein $R^a$ and $R^b$ are as defined previously) with 2,2-diphenylethylamine, preferably in the presence of a base such as an amine base (e.g. diisopropylethylamine) and in a solvent such as an alcohol (e.g. isopropanol) at an elevated temperature (e.g. reflux), followed if desired by removing any protecting groups present.

A compound of formula (II) in which Q represents an oxygen atom may also be prepared by treating a compound of formula (IV)

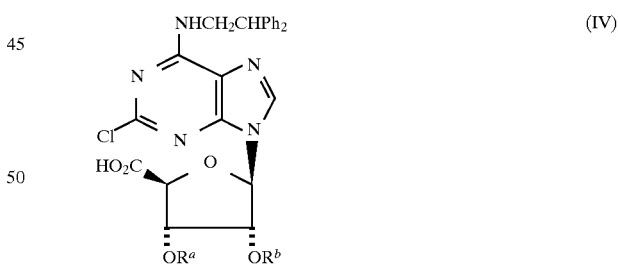

(wherein $R^a$ and $R^b$ are as defined previously) or an active derivative thereof such as the corresponding acid halide with an amine $R^1NH_2$, followed if desired by removing any protecting groups present.

The amination reaction may be effected in known manner, for example by adding the amine in a solvent such as a halogenated hydrocarbon (e.g. methylene chloride) at about 0° to 20° C. to the compound (IV) or, more particularly, the corresponding acid chloride. The acid chloride may be prepared by treating compound (IV) with thionyl chloride, conveniently at an elevated temperature.

A compound of formula (IV) may be prepared by oxidising a compound of formula (V)

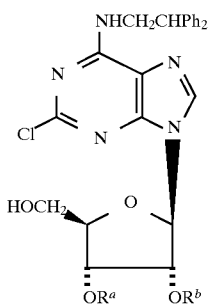

or a salt thereof (wherein $R^a$ and $R^b$ together form an alkylidene group such as isopropylidene), followed if desired by removing the alkylidene group. The oxidation reaction may be effected in known manner using an oxidising agent such as potassium permanganate or pyridinium dichromate.

A compound of formula (V) or a salt thereof may be prepared by treating a compound of formula (VI)

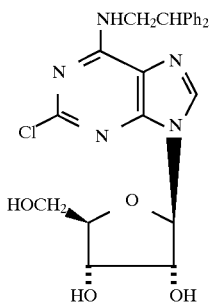

with a ketone such as acetone and/or with 2,2-dimethoxypropane in the presence of an acid, for example p-toluenesulphonic acid, conveniently at about room temperature.

A compound of formula (VI) may be prepared by deprotecting a compound of formula (VII)

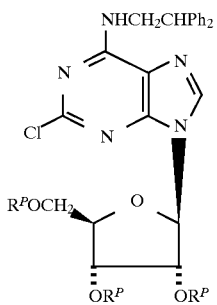

(wherein $R^P$ is a suitable hydroxyl protecting group). Suitable methods of deprotection are described hereinafter.

A compound of formula (VII) may be prepared by treating a compound of formula (VIII)

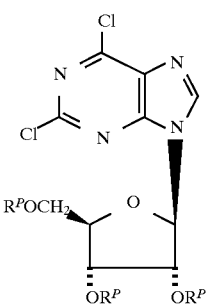

(wherein $R^P$ is as defined previously) with 2,2-diphenylethylamine under the conditions described previously for preparing compounds of formula (II) from compounds of formula (III).

The compounds of formulae (III) and (VIII) are either known compounds or may be prepared by methods analogous to those described in the art for preparing the known compounds of formulae (III) and (VIII).

The amines $R^{2a}NH_2$ are either known in the art or may be prepared by the methods described in the Examples Section hereinafter or by methods analogous to such methods hereinafter.

Compounds of formulae (II) and (IV) are novel intermediates and represent further aspects of the present invention. Compounds of formula (II) in which $R^a$ and $R^b$ represent hydrogen atoms are also active compounds in their own right and constitute a further particular aspect of the present invention.

It will be appreciated that in addition to 2',3'-diol groups, groups present within $R^2$ may need to be protected, and deprotection may be required as an intermediate or final step to yield the desired compound. Thus, according to another general process (B), a compound of formula (I) may be prepared by subjecting a protected derivative of a compound of formula (I) to reaction to remove the protecting group or groups. Protection and deprotection of functional groups may be effected using conventional means. Thus, for example, amino groups may be protected by a group selected from aralkyl (e.g. benzyl), acyl (e.g. benzyloxycarbonyl or t-butoxycarbonyl) or sulphonyl (e.g. allysulphonyl or tosyl); subsequent removal of the protecting group being effected when desired by hydrolysis or hydrogenolysis as appropriate using standard conditions. Hydroxyl groups may be protected using any conventional hydroxyl protecting group, for example, as described in "Protective Groups in Organic Chemistry", Ed. J. F. W. McOmie (Plenum Press, 1973) or "Protective Groups in Organic Synthesis" by Theodora W. Greene (John Wiley and Sons, 1991). Examples of suitable hydroxyl protecting groups include groups selected from alkyl (e.g. methyl, t-butyl or methoxymethyl), aralkyl (e.g. benzyl, diphenylmethyl or triphenylmethyl), heterocyclic groups such as tetrahydropyranyl, acyl (e.g. acetyl or benzoyl) and silyl groups such as trialkylsilyl (e.g. t-butyldimethylsilyl). The hydroxyl protecting groups may be removed by conventional techniques. Thus, for example alkyl, silyl, acyl and heterocyclic groups may be removed by solvolysis, e.g. by hydrolysis under acidic or basic conditions. Aralkyl groups such as triphenylmethyl may similarly be removed by solvolysis, e.g. by hydrolysis under acidic conditions. Aralkyl groups such as benzyl may be cleaved by hydrolysis in the presence of a Noble metal catalyst such as palladium-on-charcoal. Silyl groups may also conveniently be removed using a source of fluoride ions such as tetra-n-butylammonium fluoride. Carboxyl protecting groups may conveniently be represented by appropriate hydroxyl protecting groups above with deprotection effected according to the method described above. An example of such a group is an alkyl (e.g. methyl or t-butyl) group which can be removed by acid hydrolysis (e.g. using trifluoroacetic or hydrochloric acid) or an aralkyl (e.g. benzyl) group which can be removed by catalytic hydrogenolysis.

Particularly suitable hydroxyl protecting groups represented by $R^P$ include acyl groups such as acetyl or benzoyl. An alkylidene protecting group may conveniently be removed by acid-catalysed hydrolysis, for example using trifluoroacetic, sulphuric or hydrochloric acid.

Compounds of formula (I) may also be prepared from other compounds of formula (I) or protected derivatives thereof using conventional interconversion procedures, including N-acylation, N-debenzylation and oxidation of a hydroxyl group to a ketone, followed, if necessary, by the removal of any protecting groups present.

Individual isomers of formula (I) may either be prepared from starting materials having the desired stereochemistry or by epimerisation, resolution or chromatography (e.g. HPLC separation) at an appropriate stage in the synthesis of the required compounds of formula (I) using conventional means.

When it is desired to prepare an acid addition salt of a compound of formula (I) the product of the above procedure may be converted into a salt by treatment of the resulting free base with a suitable acid using conventional methods.

Physiologically acceptable acid addition salts of the compounds of formula (I) may be prepared by reacting a compound of formula (I) in the form of a free base with an appropriate acid optionally in the presence of a suitable solvent such as an ester (e.g. ethyl acetate) or an alcohol (e.g. methanol, ethanol or isopropanol).

Inorganic basic salts may be prepared by rating the free base of a compound of formula (I) using conventional methods.

Solvates (e.g. hydrates) of a compound of formula (I) may be formed during the work-up procedure of one of the aforementioned process steps.

The following Examples illustrate the invention but do not limit the invention in any way. All temperatures are in °C. Hereinafter the term DMSO means dimethylsulphoxide.

EXAMPLES

General

Where products were purified by column chromatography, 'silica' refers to silica gel for chromatography, 0.063 to 0.20 mm mesh (e.g. Merck Art 7735); 'flash silica' refers to silica gel for chromatography, 0.040 to 0.063 mm mesh (e.g. Merck Art 9385). In this latter case column elution was accelerated by an applied pressure of nitrogen at up to 5 p.s.i.

Where products were purified by preparative HPLC, this was carried out on a C18-reversed-phase column (1" Dynamax), eluting with a gradient of acetonitrile (containing 0.1% trifluoroacetic acid) in water (containing 0.1% trifluoroacetic acid) and the compounds isolated as their trifluoroacetate salts unless otherwise specified.

Preparation 1

2-Chloro-N-(2,2-diphenylethyl)-adenosine 2',3',5'-triacetate

A solution of 2,6-dichloro-9-(2,3,5-tri-O-acetyl-β-D-ribofuranosyl)-9H-purine[1] (6.68 g, 14.9 mmol) in 2-propanol (300 ml) was stirred and heated at reflux with 2,2-diphenylethylamine (4.3 g, 21.8 mmol) in the presence of diisopropylethylamine (3.8 ml) for 3.5 h. The cooled mixture was reduced in volume by evaporation in vacuo and the residue was diluted with ethyl acetate (200 ml). This mixture was washed with water (100 ml); 10% citric acid solution (2×100 ml) and water (100 ml) then dried (MgSO$_4$) and evaporated to give the title compound (9.01 g) as a pale yellow froth. A sample (500 mg) was purified by column chromatography on flash silica eluting with ethyl acetate-:cyclohexane (1:2). The product (0.34 g) was obtained as a white froth $[\alpha]_D$ −20° (CHCl$_3$ c=1%).

1. M. J. Robins and B. Uznanski, Canad. J. Chem., 1981, 59(17), 2608.

Preparation 2

2-Chloro-N-(2,2-diphenylethyl)-adenosine

2-Chloro-N-(2,2-diphenylethyl)-adenosine 2',3',5'-triacetate (2.0 g, 3.29 mmol) was dissolved in methanol (120 ml) and the solution was stirred at room temperature with 2M aqueous sodium carbonate solution (10 ml). After 2 h the mixture was diluted with water (350 ml) and extracted with ethyl acetate (2×100 ml). The extract was washed with water (100 ml) and dried (MgSO$_4$) then evaporated to leave a froth (1.42 g). A sample (0.42 g) was purified by column chromatography on flash silica eluting with ethyl acetate:cyclohexane (3:1). Evaporation of appropriate fractions gave an oil which was treated with ether (20 ml) to give a solid, which was collected by filtration, washed with ether and dried in vacuo to give the title compound (0.177 g) as a solid $[\alpha]_D$ −39° (CHCl$_3$ c=1%).

Preparation 3

2-Chloro-N-(2,2-diphenylethyl)-2,3-O-(1-methylethylidene)-adenosine toulene-4-sulphonate salt Toluene-4-sulphonic acid (7.0 g, 37 mmol) was added to a stirred solution of 2-chloro-N-(2,2-diphenylethyl)-adenosine (6.85 g, 14 mmol) in acetone (300 ml) and 2,2-dimethoxypropane (90 ml). After a few minutes a precipitate formed which dissolved within 0.5 h. The reaction was stirred for 3 days and the precipitate formed was collected by filtration and washed with acetone (50 ml) and dried to give the title compound (4.64 g) $[\alpha]_D$ −38° (1,4-dioxan c=1%). A second crop (2.7 g) was obtained from the mother liquors.

Preparation 4

1-[2-Chloro-6-[(2,2-diphenylethyl)amino]-9H-purin-9-yl]-1-deoxy-2,3-O-(1-methylethylidene)-β-D-ribofuranuronic acid A solution of 2-chloro-N-(2,2-diphenylethyl)-2,3-O-(1-methylethylidene)-adenosine toluene-4-sulphonate salt (6.94 g, 10 mmol) in 1,4-dioxan (200 ml) was added to a cold (4° C.) solution of potassium permanganate (8.85 g, 56.1 mmol) and potassium hydroxide (2.71 g, 48.4 mmol) in water (200 ml) keeping the temperature below 10° C. On complete addition the mixture was stirred for 3.5 h between 5° C. and room temperature. A 5% aqueous solution of sodium metabisulphite was added in portions until all colouration had been discharged. The pH was then adjusted to pH 3 with concentrated hydrochloric acid and the mixture was extracted with ethyl acetate (3×200 ml). The extract was washed with water (200 ml) and dried (MgSO$_4$) and evaporated to leave a waxy solid (5.45 g) which was dried in vacuo. The majority of this solid (4.1 g) was stirred with ether (100 ml) and 5% aqueous sodium bicarbonate solution (100 ml) until solution was obtained. The aqueous phase was washed with ether (2×100 ml) then brought to pH3 with 10% citric acid solution to give a precipitate which was collected by filtration, washed with water (100 ml) and dried. The resulting solid (6.1 g) was stirred with water (500 ml) for 2 h then collected by filtration, washed with water (50 ml) and dried in vacuo over phosphorus pentoxide to give the title compound (3.52 g) $[\alpha]_D$ +53° ($CHCl_3$ c=1%).

Preparation 5

1-[2-Chloro-6-[(2,2-diphenylethyl)amino]-9H-purin-9-yl]-1-deoxy-N-ethyl-2,3,-O-(1-methylethylidene)-β-D-ribofuranuronamide A solution of 1-[2-chloro-6-[(2,2-diphenylethyl)amino]-9H-purin-9-yl]-1-deoxy-2,3-O-(1-methylethylidene)-β-D-ribofuranuronic acid (3.3 g, 6.16 mmol) in thionyl chloride (10 ml) was heated at 70° C. for 1.5 h. The mixture was evaporated to leave a pale brown froth which was azeotroped with toluene twice. The resulting froth was dissolved in dichloromethane (50 ml) and the solution was cooled to 5° C. A solution of ethylamine (6 ml) in dichloromethane (20 ml) was added in portions and the mixture was left at 5° C. for 30 min then poured into water (100 ml). The aqueous phase was extracted with dichloromethane (3×50 ml), the extract was washed with water and dried ($MgSO_4$) then evaporated to leave a froth (3.37 g) which was purified by column chromatography on flash silica eluting with ethyl acetate:cyclohexane (1:1) to give the title compound (2.74 g) as a pale yellow froth $[\alpha]_D$ −18.9° ($CHCl_3$ c=0.9%).

Preparation 6

2-Chloro-N-(2,2-diphenylethyl)-adenosine 2',3',5'-tribenzoate

A mixture of 2,6-dichloro-9-(2,3,5-tri-O-benzyl-β-D-ribofuranosyl)-9H-purine[1] (67.69 g), 2,2-diphenylethylamine (27.67 g) and diisopropylethylamine (75.5 g) in 2-propanol (2200 ml) was heated under reflux for 2.5 h. The cooled mixture was evaporated, and the residual orange foam purified on flash silica (1.5 kg) eluting with ethyl acetate:cyclohexane (1:2)to yield the title compound (71.2 g) as a pale brown foam, nmr(δ,$CDCl_3$) 4.2 to 4.4 and 4.6 to 4.95(2 m,6H), 5.97 (br.s,1H), 6.14(q,2H), 6.43(d,1H), 7.15 to 7.65 (m, ca 19H), 7.79(s,1H), 7.9 to 8.15(m,6H).
1. K. Imai, et al., Chem. Pharm. Bull., 1966, 14, 1377.

Preparation 7

2-Chloro-N-(2,2-diphenylethyl)-adenosine

2-Chloro-N-(2,2-diphenylethyl)-adenosine 2',3',5'-tribenzoate (71.2 g) in methanol (980 ml) was treated with potassium carbonate (52.1 g). The suspension was stirred at 22° C. for 2 h. It was then acidified to pH 8 with concentrated hydrochloric acid, evaporated and purified on flash silica (2 kg) eluting with dichloromethane:ethanol:0.880 ammonia (90:10:1) to give the title compound (40.2 g) as a white solid, nmr(δ,DMSO-$d_6$) 3.58(m,1H), 3.65(m,1H), 3.84(br.s,1H), 4.0 to 4.2 and 4.4 to 4.65(2 m,5H), 5.04(t,1H), 5.22 (d,1H), 5.48 (d,1H), 5.82(m,1H), 7.1 to 7.4(m,10H), 8.33(s,1H), 8.42(t,1H).

Preparation 8

2-Chloro-N-(2,2-diphenylethyl)-2,3-O-methylethylidene)-adenosine

2-Chloro-N-(2,2-diphenylethyl)-adenosine (40 g) in acetone (970 ml) was treated with 2,2-dimethoxypropane (49 ml) and toluene-4-sulphonic acid (4.97 g). The mixture was stirred at ca 22° C. for 67 h, then the slurry was evaporated and chromatographed on flash silica eluting with dichloromethane:methanol (19:1) to give the title compound (39.6 g) as a white solid. A portion (1.5 g) was recrystallised from ethyl acetate to give an analytically pure sample, 1.27 g, m.p. 185° to 187°, $[\alpha]_D$ −86° (c,0.8%, $CHCl_3$).

Preparation 9

1-[2-Chloro-6-[(2,2-diphenylethyl)amino]-9H-purin-9-yl]-1-deoxy-N-ethyl-2,3-O-(1-methylethylidene)-β-D-ribofuranuronamide 1-(2,6-Dichloro-9H-purin-9-yl)-1-deoxy-N-ethyl-2,3-O-(1-methylethylidene)-β-D-ribofuranuronamide[1] (5.66 g, 14.07 mmol) was heated at reflux in 2-propanol (300 ml) with 2,2-diphenylethylamine (3.62 g, 18.3 mmol) in the presence of N,N-diisopropylethylamine (13.2 ml) for 6 h. The cooled solution was evaporated to a brown foam which was purified on silica eluting with ethyl acetate to give the title compound (7.31 g) as a pale yellow foam, nmr(δ, DMSO-d6) 0.62(t,3H), 1.34(s,3H), 1.53(s,3H), 2.82(m,2H), 4.05(m,1.5H), 4.54(m,2.5H), 5.40(m,2H). 6.18(s,1H), 7.1 to 7.4(m,10H), 7.50(t,1H), 8.22(s,1H), 8.40(m,1H).
1. R. R. Schmidt et al., Chem. Ber., 1980, 113, 2891.

Preparation 10

1-[2-Chloro-6-[(2,2-diphenylethyl)amino]-9H-purin-9-yl]-1-deoxy-N-ethyl-β-D-ribofuranuronamide 1-[2-Chloro-6-[(2,2-diphenylethyl)amino-9H-purin-9-yl]-1-deoxy-N-ethyl-2,3-O-(1-methylethylidene)-β-D-ribofuranuronamide (2.02 g) was treated with trifluoroacetic acid (10 ml) and water (1.1 ml), and the resulting solution was stirred at 20° C. for 2 h. The mixture was evaporated and the residue was treated with sodium hydrogen carbonate (3.75 g) and ethanol (30 ml) and stirred for 1 h. The mixture was filtered and the solid was washed with ethanol. The total filtrate and washings were evaporated and the residue was purified on flash silica eluting with ethyl acetate:methanol (19:1) to give the title compound (1.96 g) as a white solid, nmr(δ,DMSO-d6) 1.05(t,3H), 3.22(m,2H), 4.0 to 4.2(m, 2.5H), 4.30(m,1H), 4.45 to 4.65(m,2.5H), 5.58(d,1H), 5.72 (d,1H), 5.90(d,1H), 7.14 to 7.40(m, 10H), 8.36(t,1H), 8.43 (s,1H), 8.52(t,1H).

Preparation 11

[cis-(±)]-[3-[(Methylsulphonyl)oxy]cyclopentyl] carbamic acid phenylmethyl ester Methanesulphonyl chloride (0.163 ml, 2.1 mmol) was added to a stirred mixture of [cis-(±)]-(3-hydroxycyclopentyl)carbamic acid phenylmethyl ester[1] (0.47 g, 2 mmol) and triethylamine (0.293 ml, 2 mmol) in acetone (10 ml). After 2 h more reagents as above were added and the reaction was left for a further 1 h. Water (70 ml) and ethyl acetate (70 ml) were added and the organic phase was washed with water (20 ml), dried ($MgSO_4$) and evaporated to leave a solid (0.71 g) which was purified by column chromatography on flash silica eluting with 50% ethyl acetate in cyclohexane to give the title compound (0.532 g), m.p.84°–86° C. (from ether).
1. Published European Patent Application EP-A-322242.

Preparation 12

[trans-(±)]-[3-(N,N-Dimethylamino)cyclopentyl] carbamic acid phenylmethyl ester

A solution of [cis-(±)]-[3-[(methylsulphonyl)oxy] cyclopentyl]carbamic acid phenylmethyl ester (2 g, 6.38 mmol) in 33% dimethylamine in ethanol (30 ml) was heated at reflux for 4 h. The cooled mixture was diluted with water (250 ml) and extracted into ethyl acetate (3×70 ml). The extract was dried (MgSO$_4$) and evaporated to leave an oil which crystallised from ether/cyclohexane to give the title compound (1.28 g) m.p. 85°–86° C.

Preparation 13

[trans-(±)]-3-(N,N-Dimethylamino) cyclopentylamine

A solution of [trans-(±)]-[3-(N,N-dimethylamino) cyclopentyl]carbamic acid phenylmethyl ester (1.4 g, 5.34 mmol) in tetrahydrofuran (100 ml) was hydrogenated over 10% palladium-on-carbon (0.17 g) for 3 days. The catalyst was removed by filtration, washed with tetrahydrofuran (20 ml) and the combined organic phases were evaporated with a stream of nitrogen to leave the title compound (0.412 g) as an oil, nmr(δ,CDCl$_3$) includes 1.25–1.65(m,3H), 1.7–1.85 (m,1H), 1.85–2.1(m, 2H), 2.25(s,6H), 2.65(m,1H), 3.48(m, 1H).

Preparation 14

[trans(±)]-(3-Azidocyclopentyl)carbamic acid phenylmethyl ester

A solution of sodium azide (0.5 g, 7.69 mmol) in water (2 ml) was added to a solution of [cis-(±)]-[3-[(methanesulphonyl)oxy]cyclopentyl]carbamic acid phenylmethyl ester (1.74 g, 5.55 mmol) in dimethylformamide (12 ml) and the mixture was heated at 100° C. for 0.5 h. The cooled reaction mixture was diluted with water (150 ml) and extracted into ethyl acetate (3×50 ml). The extract was washed with water (50 ml), dried (MgSO$_4$) and evaporated to leave the title compound (1.41 g) as an oil which solidified on drying, nmr(δ,CDCl$_3$) includes 1.4–1.55(m,1H), 1.6–1.85(m,2H), 1.95–2.3(m,3H), 4.05(m,1H), 4.17(m,1H), 4.72(bs,1H), 5.1(s,2H), 7.45(s,5H).

Preparation 15

[trans-(±)]-(3-Aminocyclopentyl)carbamic acid phenylmethyl ester

A solution of [trans-(±)]-(3-azidocyclopentyl)carbamic acid phenylmethyl ester (4.65 g, 0.179 mmol) in ethanol (230 ml) was hydrogenated over 10% palladium-on-carbon (0.5 g) by bubbling hydrogen through the stirred solution for 40 min. The mixture was filtered through celite and the pad was washed with ethanol (50 ml). The combined ethanolic solution was evaporated to leave an oil (4.2 g) which was partitioned between 2M hydrochloric acid (50 ml) and ethyl acetate (50 ml). The organic phase was extracted with 2M hydrochloric acid (2×20 ml) and the combined aqueous phase was brought to pH 8 with sodium carbonate solution and extracted with ethyl acetate (3×70 ml). The extract was dried (MgSO$_4$) and evaporated to leave the title compound (0.32 g) as a solid, nmr(δ,CDCl$_3$) includes 1.25–1.45(m, 4H), 1.75(t,2H), 1.9–2.1(m,1H), 2.1–2.3(m,1H), 3.47(m, 1H), 4.2(m,1H), 4.72(bs,1H), 5.1(s,2H), 7.47(s,5H).

Preparation 16

[trans-(±)]-[3-[(Methylsulphonyl)oxy]cyclopentyl] carbamic acid phenylmethyl ester Methanesulphonyl chloride (1.42 ml, 18.35 mmol) was added to a stirred solution of [trans-(±)]-3-hydroxycyclopentyl)carbamic acid phenylmethyl ester[1] (2.16 g, 9.19 mmol) and triethylamine (2.54 ml, 18.35 mmol) in acetone (100 ml). The mixture was stirred for 2 h then diluted with water (500 ml) and extracted into ethyl acetate (3×100 ml). The extract was washed with water (100 ml), dried (MgSO$_4$) and evaporated to leave the title compound (2.75 g) as a solid, nmr(δ,CDCl$_3$) includes 1.45–1.6 (m,1H), 1.77–1.9(m,1H), 1.9–2.1(m,1H), 2.1–2.3(m,2H), 2.3–2.45(m,1H), 3.0(s,3H), 4.25(m,1H), 4.73(bs,1H), 5.1(s, 2H), 5.2(m,1H), 7.35(s,5H).

1. Published European Patent Application EP-A-322242.

Preparation 17

[cis-(±)]-(3-Azidocyclopentyl)carbamic acid phenylmethyl ester

Sodium azide (0.74 g, 10.4 mmol) was dissolved in water (4 ml) and the solution was added to a solution of [trans-(±)]-[3-[(methylsulphonyl)oxy]cyclopentyl]carbamic acid phenylmethyl ester (2.35 g, 7.25 mmol) in dimethylformamide (15 ml). The mixture was heated at 100° C. for 2 h, cooled and partitioned between ethyl acetate (50 ml) and water (50 ml). The aqueous phase was extracted with ethyl acetate (2×50 ml) and the combined extract was washed with water (2×50 ml), dried (MgSO$_4$) and evaporated to leave the title compound (1.92 g) as an oil, nmr(δ,CDCl$_3$) includes 1.55–1.7(m,2H), 1.85(m,2H), 2.0–2.27(m,2H), 4.05(m,1H), 4.17(m,1H), 5.0(m,1H), 5.1(s,2H), 7.35(s,5H).

Preparation 18

[cis-(±)]-(3-Aminocyclopentyl)carbamic acid phenylmethyl ester

A solution of [cis-(±)]-(3-azidocyclopentyl)carbamic acid phenylmethyl ester (1.46 g, 5.61 mmol) in ethanol (60 ml) was hydrogenated over 10% palladium-on-carbon (0.2 g) by bubbling hydrogen through the solution for 30 min. The catalyst was removed by filtration, washed with ethanol (20 ml) and the combined organic solution was evaporated to leave an oil (1.41 g). A portion (1 g) was partitioned between 2M hydrochloric acid (5 ml) and ethyl acetate (10 ml). Water was added and the aqueous phase was washed with ethyl acetate (2×10 ml), brought to pH 9 with sodium carbonate solution and extracted with ethyl acetate (3×25 ml). The extract was washed with water (2×20 ml), dried (MgSO$_4$) and evaporated to leave the title compound (0.37 g) as an oil, nmr(δ,CDCl$_3$) includes 1.25–1.55(m,2H), 1.65–1.95(m, 2H), 1.95–2.1(m,2H), 3.52(m,1H), 4.15(m,1H), 5.1(s,2H), 5.33(m,1H), 7.35–7.45(m,5H).

Preparation 19

2,5-Dihydro-1H-pyrrole-1-carboxylic acid 1,1-dimethylethyl ester

Di-t-butyl pyrocarbonate (84.2 g, 0.386 mole) was added to an ice-cold solution of 70% pure 3-pyrroline (25 g, 0.253 mole) in 1,4-dioxan (150 ml). After 3 days the mixture was diluted with ethyl acetate (200 ml) and washed with water (5×200 ml). The aqueous phase was extracted with ethyl acetate (100 ml) and the combined organic solution was washed with water (100 ml), dried (MgSO$_4$) and evaporated to leave an oil which was purified by column chromatography on flash silica eluting with 30% ethyl acetate in cyclohexane to give the title compound (48.6 g) as an oil, nmr(δ,CDCl$_3$) includes 1.45(s,9H), 4.12(dd, 4H), 5.77(m, 2H).

Preparation 20

3-[(1,1-Dimethylethoxy)carbonyl]-6-oxa-3-azabicyclo[3.1.0]hexane

80% m-Chloroperbenzoic acid (3.9 g, 0.0226 mole) was added to a solution of 2,5-dihydro-1H-carboxylic acid 1,1-dimethylethyl ester (3.55 g) 0.021 mole) in dichloromethane (70 ml) and the mixture was stirred for 24 h when more peracid (0.27 g, 0.00156 mole) was added and the stirring continued for a further 4 h. Ethyl acetate was added and the mixture was washed with 10% sodium carbonate solution. The aqueous phase was extracted with ethyl acetate (50 ml) and the combined organic solution washed with water, dried (MgSO$_4$) and evaporated to leave an oil which was purified by column chromatography on flash silica eluting with 30% ethyl acetate in cyclohexane to give the title compound (1.52 g) as an oil, nmr($\delta$,CDCl$_3$) includes 1.45(s,9H), 3.42(dd, 2H), 3.67(s,2H), 3.78(dd,2H).

Preparation 21

[trans-($\pm$)]-3-Hydroxy-4-[(phenylmethyl)amino]-1-pyrrolidinecarboxylic acid 1,1-dimethylethyl ester A solution of 3-[(1,1-dimethylethoxy)carbonyl]-6-oxa-3-azabicyclo[3.1.0.]hexane (1.32 g, 7.13 mmol) and benzylamine (2 ml) in 1,4-dioxan (5 ml) and water (5 ml) was heated at 85° C. for 5 h. The reaction was allowed to cool over 18 h and the solid formed was collected by filtration and crystallised from ethyl acetate/cyclohexane to give the title compound (1.3 g) nmr($\delta$,DMSO-d$_6$) includes 1.4(s,9H), 2.32(bs,1H), 2.93(bs,1H), 3.1(bt,2H), 3.4(m,1H), 3.7(bs, 2H), 3.97(bs,1 h), 5.0(d,1H), 7.15–7.35(m,5H).

Preparation 22

[trans-($\pm$)]-3-Amino-4-hydroxy-1-pyrrolidinecarboxylic acid 1,1-dimethylethyl ester A solution of [trans-($\pm$)]-3-hydroxy-4-[(phenylmethyl)amino]-1-pyrrolidinecarboxylic acid 1,1-dimethylethyl ester (1.1 g, 3.76 mmol) in ethanol (150 ml) was hydrogenated over 10% palladium-on-carbon (0.05 g) for 3.5 h. The catalyst was removed by filtration, washed with ethanol (50 ml) and the combined ethanolic solution was evaporated to leave an oil which was taken up in ethyl acetate (75 ml). The solution was filtered and the filtrate evaporated to leave a solid which was crystallised from ethyl acetate/cyclohexane to give the title compound (0.643 g), nmr($\delta$,CDCl$_3$) 1.45(s, 9H), 1.6–2.2(bm, 3H), 3.1(m,1H), 3.3(m,2H), 3.68(m,2H), 3.98(m,1H).

Preparation 23

1-Amino-cyclopropanemethanol

A slurry of lithium borohydride (0.771 g, 35.4 mmol) in tetrahydrofuran (20 ml) was stirred during the addition of chlorotrimethylsilane (9 ml, 70.8 mmol) and the mixture was stirred for 5 min on complete addition. 1-amino-1-cyclopropanecarboxylic acid (1.95 g, 17.7 mmol) was then added in portions over 5 min and the mixture was stirred for 18 h at room temperature. Methanol (30 ml) was added dropwise over 10 min then the mixture was concentrated to leave a gum which was treated with 20% potassium hydroxide solution (50 ml) and extracted with dichlommethane (4×75 ml). The combined extract was dried (Na$_2$SO$_4$) and evaporated to give the title compound (0.286 g) as a solid, nmr($\delta$,CDCl$_3$) includes 0.5–0.6 and 0.6–0.7(m,4H), 1.8(s, 3H), 3.47(s,2H).

Preparation 24

($\pm$)-4-Trimethylsilyloxy-1H-pyrrolidin-2one ($\pm$)-4-Amino-3-hydroxybutyric acid (1.0 g, 8.39 mmol), xylene (110 ml), hexamethyldisilazane (12.4 ml, 58.7 mmol) and chlorotrimethylsilane (2 drops) were heated at reflux for 4 h then the cooled mixture was poured into ethanol (250 ml). The resulting solution was evaporated to leave a solid which was taken up in chloroform (150 ml) and filtered through celite. The filtrate was evaporated to dryness and the residue was purified by column chromatography on flash silica eluting with 5–25% methanol in chloroform to give the title compound (0.757 g) as a solid, nmr($\delta$,CDCl$_3$) 0.1–0.2(m,9H), 2.28 and 2.55(dd and dd,2H), 3.25 and 3.6(dd and dd,2H), 4.5–4.6(m,1H), 5.6–5.7(m,1H).

Preparation 25

($\pm$)-4-[(Methylsulphonyl)oxy]-1H-pyrrolidin-2-one ($\pm$)-4-Trimethylsilyloxy-1H-pyrrolidin-2-one (20 g, 11.5 mmol) in acetonitrile (30 ml) was treated with 4M HCl (2.9 ml, 11.5 mmol) and the mixture was stirred for 45 min before evaporating to leave a brown oil. This oil was azeotroped with toluene (2×10 ml) then taken up in acetone (40 ml) and stirred with methanesulphonyl chloride (1.8 ml, 23 mmol) and triethylamine (3.2 ml, 23 mmol) for 2.5 h. More methanesulphonyl chloride (0.9 ml, 11.5 mmol) and triethylamine (1.6 ml, 11.5 mmol) were added and the reaction was left for 16 h. More methanesulphonyl chloride (1.35 ml, 17.3 mmol) and triethylamine (2.4 ml, 17.3 mmol) were added and the mixture was stirred for another 2 h before evaporating to leave a solid which was purified by column chromatography on flash silica eluting with 5–10% methanol in chloroform to give the title compound (0.813 g) as a solid which can be crystallised from ethyl acetate/cyclohexane, nmr($\delta$,CDCl$_3$) includes 2.59 and 2.78(dd and dd,2H), 3.09(s,3H), 3.68 and 3.81(bd and dd,2H), 5.37–5.45 (m,1H), 5.5–5.7(m,1H).

Preparation 26

($\pm$)-4-Amino-1H-pyrrolidin-2-one hydrochloride

A solution of ($\pm$)-4-[(methylsulphonyl)oxy]-1H-pyrrolidin-2one (0.8 g, 4.9 mmol) and sodium azide (0.348 g, 5.39 mmol) in dimethylformamide (15 ml) was stirred at room temperature for 65 h then heated at 50° C. for 6 h. Water was added to the cooled reaction and the product was extracted into ethyl acetate (8×20 ml) and the combined extract was dried (Na$_2$SO$_4$) and concentrated to 15 ml. This solution was hydrogenated in ethanol (25 ml) over 10% palladium-on-carbon (0.165 g) by bubbling hydrogen through the solution for 1 h. The mixture was filtered through celite and the filtrate was concentrated to 10 ml and this was stirred with 4M hydrochloric acid (0.88 ml, 4.9 mmol). After 3 h the mixture was evaporated and dried to give a solid which was stirred in ethanol for 0.5 h and collected by filtration to give the title compound (0.402 g, 60%) nmr($\delta$,DMSO-d6) includes 2.2–2.58(2×dd,2H), 3.24 and 3.55(2×dd,2H), 3.85–3.96(m,1H), 7.82–7.87(bs,1H), 8.3–8.5(bs,3H).

Preparation 27

[cis-($\pm$)]-(2-Hydroxycyclopentyl)carbamic acid phenylmethyl ester

A solution of [cis-($\pm$)]-2-aminocyclopentanol[1] (6.0 g, 58.4 mmol) in 1,4-dioxan (100 ml) and water (50 ml) was treated with sodium carbonate (30.9 g, 292 mmol) and benzyl chloroformate (8.34 ml, 58.4 mmol). The resulting mixture was stirred at 21° C. overnight. It was then poured into 2N-hydrochloric acid (300 ml) and extracted with ethyl acetate (3×100 ml). The total organic solution was washed (brine, 200 ml), dried ($Na_2SO_4$) and evaporated to an oil (17.13 g) which was purified on silica, eluting with cyclohexane: ethyl acetate (2:1) to give the title compound (6.089 g) as a white solid, nmr(δ,$CDCl_3$) 1.4 to 2.1(m,7H), 3.88 (m,1H), 4.18(m,1H), 5.11(br.s,3H), 7.35(m,5H).

1. R. A. B. Bannard et al. *Canad. J. Chem.* 1971,49,2064.

Preparation 28

[cis-(±)]-2-[(Methylsulphonyl)oxy]cyclopentyl] carbamic acid phenylmethyl ester

Methanesulphonyl chloride (1.85 ml, 23.9 mmol) was added to a stirred mixture of [cis-(±)]-(2-hydroxycyclopentyl)carbamic acid phenylmethyl ester (2.50 g, 10.6 mmol) and triethylamine (3.35 ml, 23.9 mmol) in dichloromethane (125 ml) at 21° C. The resulting yellow solution was stirred at 21° C. overnight. It was then washed (water, 100 ml, then brine, 100 ml), dried ($Na_2SO_4$) and evaporated to a yellow oil (4.20 g). The oil was purified on silica, eluting with cyclohexane:ethyl acetate (3:2) to give the title compound (3.29 g) as a yellow oil which crystallised on standing, m.p. 74° to 76° C.

Preparation 29

[trans-(±)]-(2-Azidocyclopentyl)carbamic acid phenylmethyl ester

A solution of [cis-(±)]-[2-[(methylsulphonyl)oxy] cyclopentyl]carbamic acid phenylmethyl ester (3.23 g, 10.3 mmol) in N,N-dimethylformamide (50 ml) and water (10 ml) was stirred and treated with sodium azide (0.823 g, 12.66 mmol). The resulting solution was then stirred and heated in an oil-bath at 100° C. for 2.5 h, and was then left to cool to 21° C. The mixture was diluted with water (200 ml) and extracted with ethyl acetate (3×100 ml). The total organic solution was washed (water, 2×100 ml, then brine, 200 ml), dried ($Na_2SO_4$) and evaporated to a yellow oil (2.63 g) which was purified on silica, eluting with cyclohexane-:ethyl acetate (4:1) to give the title compound (2.00 g) as a pale yellow oil, nmr (δ,$CDCl_3$) 1.4 to 1.55(m,1H), 1.6 to 1.8(m,3H), 1.9 to 2.05(m,1H), 2.05 to 2.2(m,1H), 3.72(m, 1H), 3.90(m,1H), 4.70(br.s,1H), 5.12(s,2H), 7.35(m,5H); ir ($CHBr_3$) 2101 $cm^{-1}$ ($N_3$).

Preparation 30

[trans-(±)]-(2-Aminocyclopentyl)carbamic acid phenylmethyl ester

A solution of [trans-(±)]-(2-azidocyclopentyl)carbamic acid phenylmethyl ester (0.25 g) in ethanol (20 ml) was added slowly to a suspension of 10% palladium-on-carbon catalyst (0.025 g) in ethanol (2 ml) under nitrogen. Hydrogen was bubbled through the suspension for 20 min and the mixture was then immediately purged with nitrogen and filtered through elite. The filtrate was evaporated to an oil (0.17 g). The oil was dissolved in ethyl acetate (20 ml) and extracted with 2N-hydrochloric acid (2×25 ml). The total aqueous solution was covered with ethyl acetate (25 ml) and basified with solid sodium carbonate. The aqueous layer was extracted with more ethyl acetate (25 ml) and the total organic solution was washed (brine, 30 ml), dried ($Na_2SO_4$) and evaporated to give the title compound (0.104 g) as a yellow oil, nmr (δ,$CDCl_3$) includes 1.3 to 1.5(m,2H), 1.55 to 1.85(m,2H), 1.9 to 2.25(m,2H), 3.03(q,1H), 3.60(m,1H), 4.75(br.s,1H), 5.10(s,2H), 7.35(m,5H).

Preparation 31

[(3aα,4α, 6aα)-(±)]-N-Tetrahydro-2,2-dimethyl-4H-cyclopenta-1,3-dioxol-4-yl]-N-(phenylmethyl)amine and (1α,2β,3α)-2-(phenylmethyl)amino-1,3-cyclopentanediol A mixture of [(1α,2β,5α)-(±)]-6-oxabicyclo[3.1.0] hexane-2-ol[1] (2.5 g, 25 mmol), benzylamine (2.75 ml, 25.2 mmol) and water (15 ml) was stirred and heated at reflux for 5 h. The solution was evaporated to a brown oil which was dissolved in acetone (30 ml) and treated with 2,2-dimethoxypropane (14 ml) and 4-toluenesulphonic acid monohydrate (4.7 g). The mixture was stirred and heated under reflux overnight and was then left to cool. The mixture was partitioned between 5% sodium hydrogen carbonate solution (200 ml) and ethyl acetate (200 ml). The aqueous layer was extracted with more ethyl acetate (2×100 ml), and the aqueous and organic solutions were retained. The total organic solution was washed (brine, 50 ml), dried ($Na_2SO_4$) and evaporated to a brown oil which was purified on flash silica eluting with ethyl acetate:cyclohexane (3:1) to give [(3aα,4α,6aα)-(±)]-N-[tetrahydro-2,2-dimethyl-4H-cyclopenta-1,3-dioxol-4-yl]-N-(phenylmethyl)amine (3.41 g) as a pale brown oil; nmr(δ,$CDCl_3$) includes 1.30(s,3H), 1.42(s,3H), 1.5, 1.8, 2.0(ms,4H), 3.80(br.s,2H), 4.24(d,1H), 4.74(t,1H), 7.2 to 7.45(m,5H).

The combined aqueous layers were evaporated to a wet solid which was shaken with ethyl acetate (3×200 ml). The organic solution was filtered, dried ($Na_2SO_4$) and evaporated to a white solid which was purified on flash silica eluting with dichloromethane:ethanol:0.880 ammonia (50:8:1) to give (1α,2β,3α)-2-(phenylmethyl)amino-1,3-cyclopentanediol (0.410 g) as an off-white solid nmr(δ, DMSO-d6) includes 1.4 to 1.6, 1.65 to 1.85(ms,4H), 2.05 (br.s,1H), 2.61(t,1H), 3.6 to 3.75(m,2H), 3.81(s,2H), 4.67(d, 2H), 7.15 to 7.4(m,5H), 1. T. Itoh et al., *J. Am. Chem. Soc.*, 1979, 101, 159

Preparation 32

[(3aα,4α,6aα)-(±)]-Tetrahydro-2,2-dimethyl-4H-cyclopenta-1,3-dioxol-4-amine

[(3aα,4α,6aα)-(±)]-N-[Tetrahydro-2,2-dimethyl-4H-cyclopenta-1,3-dioxol-4-yl]-N-phenylmethyl)amine (3.2 g, 12.9 mmol) in ethanol (80 ml) was hydrogenated over 10% palladium-on-carbon catalyst (1.0 g) for 5.5 h. The catalyst was filtered off and the filtrate evaporated to give the title compound (2.02 g) as a pale grey liquid, nmr(δ,DMSO-d6) 1.18(s,3H), 1.30(s,3H), 1.5 to 1.6, 1.65 to 2.0(ms,4H), 3.19(d,1H), 4.12(d,1H), 4.61(t,1H).

Preparation 33

(1α,2β,3α)-2-Amino-1,3-cyclopentanediol (1α,2β,3α)-2-(phenylmethyl)amino-1,3-cyclopentanediol (0.380 g) in ethanol (20 ml) was hydrogenated over 10% palladium-on-carbon catalyst (0.125 g) for 7 h. The catalyst was filtered off and the filtrate was evaporated to give the title compound (0.220 g) as a pale-brown oil which solidified on storage at 4° C., nmr(δ, DMSO-d6) 1.45(m,2H), 1.75(m,2H), 3.2 to 3.55(m,3H), 4.7(m,2H).

Preparation 34

[1R-(exo,exo)]-5,6-Dihydroxy-2-azabicyclo[2.2.1]heptan-3-one

N-Methylmorpholine (12.67 g, 108 mmol) in water (39 ml) was stirred and treated with osmium tetroxide (2.5% solution in t-butanol) (4 ml) and t-butanol (16 ml). A slurry of [1R-(exo,exo)]-2-azabicyclo[2.2.1]hept-5-en-3-one[1] (10 g, 91.6 mmol) in t-butanol (50 ml) was added. The resulting brown-black solution was stirred at 70° C. for 30 min and then as it cooled to 55° C. over 25 min. Sodium hydrosulphite (0.900 g) was added, and the mixture was cooled to 30° C. and stirred at 30° C. for 30 min. Activated charcoal (4 g) was added and the mixture was stirred at 25° to 30° C. for 30 min. The mixture was filtered through celite, and the residue washed with methanol (3×20 ml). The total filtrate and washings were evaporated and azeotroped to dryness by evaporation from toluene (3×20 ml). The residue in methanol (100 ml) was heated to reflux, then filtered whilst hot and evaporated down to ca 35 ml and left at 4° C. overnight. The solid was filtered off, washed with cold methylated spirit (2×10 ml) and dried to give the title compound (7.69 g) as a brown solid, $[\alpha]_D$ −99° (H$_2$O, c=1.4%)

1. S. J. C. Taylor et al., *J. Chem. Soc., Chem. Commun.*, 1990,1120.

Preparation 35

[1S-(1α,2β,3β,4α)]-4-Amino-2,3-dihydroxycyclopentanecarboxylic acid, methyl ester, hydrochloride salt A solution of [1R-(exo,exo)]-5,6-dihydroxy-2-azabicyclo[2.2.1]heptan-3-one (11.815 g) in 3N-hydrochloric acid (85 ml) was stirred and heated at reflux for 1 h. The reaction mixture was evaporated in vacuo and was then evaporated from methanol (2×40 ml) and then from toluene (6×40 ml). The residue was treated with 1N methanolic HCl (70 ml) and then heated at reflux for 2 h. The cooled mixture was then concentrated by evaporation in vacuo and 2-propanol (100 ml) was added and the mixture was stirred for 1 h. The suspension was filtered and the residue dried to give the title compound (16.095 g) as a grey solid, nmr(δ,DMSO-6) 1.70(m,1H), 2.25(m,1H), 2.75(m,1H), 3.30(m,1H), 3.65(s,3H), 3.75(t,1H), 4.05(t,1H), 4.15(m,2H), 8.25(s,3H).

Preparation 36

[1S-(1α,2β,3β,4α)]-2,3-Dihydroxy-4-[[(phenylmethoxy)carbonyl]amino]-cyclopentanecarboxylic acid, methyl ester A solution of [1S-(1α,2β,3β,4α)]-4-amino-2,3-dihydroxycyclopentanecarboxylic acid, methyl ester, hydrochloride salt (2.054 g) in water (35 ml) was cooled to 0° C. and was treated with sodium carbonate (3.19 g). The mixture was stirred for 10 min. then a solution of benzyl chloroformate (1.52 ml) in 1,4-dioxan (60 ml) was added dropwise. The reaction was stirred at 0° to 5° C. for 30 min. then allowed to warm to 21° C. and stirred for 2.5 h. The suspension was diluted with ethyl acetate and washed with 2N-hydrochloric acid and the aqueous layer was extracted twice with fresh ethyl acetate. The combined organic layers were washed with brine, dried over sodium sulphate and evaporated to give the title compound (2.702 g) as a white solid. A small amount (0.7 g) was recrystallised from 2-propanol to give an analytical sample (0.058 g) as white needles. Analysis found C, 58.4, H, 6.25, N, 4.45%; C$_{15}$H$_{19}$NO$_6$ requires C, 58.25, H, 6.2, N, 4.5%.

Preparation 37

[3aR-(3aα,4α,6α,6aα)]-Tetrahydro-2,2-dimethyl-6-[[(phenylmethoxy)carbonyl]amino]-4-H-cyclopenta-1,3-dioxole-4-carboxylic acid, methyl ester A solution of [1S-(1α,2β,3β,4α)]-2,3-dihydroxy-4-[[(phenylmethoxy)carbonyl]amino]cyclopentanecarboxylic acid, methyl ester (21.385 g) in acetone (400 ml) was treated with 2,2-dimethoxypropane (75 ml) and toluene-4-sulphonic acid (1.58 g), and the solution was stirred at 21° C. overnight. The reaction mixture was evaporated and the residue was partitioned between ethyl acetate and 8% sodium hydrogen carbonate solution. The aqueous layer was separated and extracted twice with ethyl acetate. The combined organic layers were washed with brine, dried over sodium sulphate and evaporated to a fawn solid which was recrystallised from di-isopropyl ether to give the title compound (18.452 g) as white crystals, nmr(δ,CDCl$_3$) 1.30(s,3H), 1.45(s,3H), 1.95(d,1H), 2.45(m,1H), 3.00(d,1H), 3.70(s,3H), 4.15(t,1H), 4.50(d,1H), 4.80(d,1H), 5.10(t,2H), 5.70(m,1H), 7.35(m,5H).

Preparation 38

[3aR-(3aα,4α,6α,6aα)]-6-Amino-tetrahydro-2,2-dimethyl-4H-cyclopenta-1,3-dioxole-4-carboxylic acid, methyl ester A solution of [3aR-(3aα,4α,6α,6aα)]-tetrahydro-2,2-dimethyl-6-[[(phenylmethoxy)carbonyl]amino]-4H-cyclopenta-1,3-dioxole-4-carboxylic acid, methyl ester (18.4 g, 52.67 mmol) in ethanol (400 ml) was added to a suspension of 10% palladium-on-carbon catalyst (1.87 g) in ethanol (100 ml) under nitrogen The mixture was then hydrogenated for 6.5 h. The reaction mixture was filtered through celite and the filtrate evaporated to give the title compound (11.304 g) as a pale yellow oil, nmr(δ,CDCl$_3$) 1.30(s,3H), 1.35(s,2H), 1.45(s,3H), 1.95(dt,1H), 2.30(dt,1H), 2.90(m,1H), 3.45(m,1H), 3.70(s,3H), 4.25(d,1H), 5.10(d,1H).

Preparation 39

[3aR-(3aα,4α,6α,6aα)]-Tetrahydro-6-(formylamino)-2,2-dimethyl-4H-cyclopenta-1,3-dioxole-4-carboxylic acid, methyl ester Formic acetic anhydride (3.2 g, 36.37 mmol) was prepared from formic acid (1.37 ml) and acetic anhydride (3.46 ml) at 50° C. for 2 h. It was then added slowly in dry tetrahydrofuran (50 ml) to a stirred solution of [3aR-(3aα,4α,6α,6aα)]-6-aminotetrahydro-2,2-dimethyl-4H-cyclopenta-1,3-dioxole-4-carboxylic acid methyl ester (6.062 g, 28.16 mmol) in ether (100 ml). The mixture was stirred at 21° C. for 2 h and then evaporated to dryness. The residue was recrystallised from isopropyl ether to give the title compound (4.2434 g) as pale pink crystals, nmr(δ, CDCl$_3$) 1.30(s,3H), 1.45(s,3H), 1.95(d,1H), 2.50(m,1H), 3.10(m,1H), 3.75(s,3H), 4.50(m,2H), 4.80(d,1H), 6.80(m,1H), 8.15(s,1H).

The mother liquors were evaporated and the residue was purified on silica eluting with dichloromethane:methanol 25:1 to give a further 1.762 g of the title compound.

Preparation 40

[3aR-(3aα,4α,6aα)]-Tetrahydro-2,2-dimethyl-4H-cyclopenta-1,3-dioxole-4-carboxylic acid, methyl ester A solution of [3aR-(3aα,4α,6α,6aα)]-Tetrahydro-6-(forylamino)-2,2-dimethyl-4H-cyclopenta-1,3-dioxole-4carboxylic acid, methyl ester (6.014 g, 24.72 mmol) in dichloromethane (50 ml) at −40° C. was treated dropwise with triethylamine (8.27 ml, 59.33 mmol) and phosphoryl chloride (2.31 ml, 24.72 mmol). The reaction was stirred at 40° C. for 20 min., then allowed to warm to 21° C. and stirred for 5 h. The mixture was poured into ice/water (300 ml) containing sodium carbonate (25 g) and extracted with dichloromethane (2×100 ml). The combined organic phases were washed with brine (200 ml), dried ($Na_2SO_4$) and evaporated and azeotroped with toluene (2×50 ml). The residue was stored at 4° C. overnight. A solution of tri-n-butyltin hydride (9.31 ml, 34.61 mmol) in dry toluene (400 ml) was heated at 100° C. under nitrogen and treated dropwise over 20 min. with a solution of the above residue in dry toluene (150 ml), 2,2'-Azobis-(2-methylpropionitrile) (0.27 g) was added at the same time. The reaction was stirred at 110° C. for 2 h, then allowed to cool to 21° C. and evaporated in vacuo. The residue was purified on silica eluting with cyclohexane:ethyl acetate (2:1) to give the title compound (2.709 g) as a clear oil, nmr(δ,$CDCl_3$) 1.30(s, 3H), 1.45(s,3H), 1.70 to 1.95(m,3H), 2.10(m,1H), 2.90(d, 1H), 3.70(s3H), 4.70(t,1H), 4.85(d,1H).

Preparation 41

[3aR-(3aα,4α,6aα)]-Tetrahydro-2,2-dimethyl-4H-cyclopenta-1,3-dioxole-4-carboxylic acid

[3aR-(3aα,4α,6aα)]-Tetrahydro-2,2-dimethyl-4H-cyclopenta-1,3-dioxole-4-carboxylic acid, methyl ester (2.492 g, 12.45 mmol) in water (50 ml) and methanol (5 ml) was treated with potassium hydroxide (2.10 g, 37.35 mmol), and the mixture was stirred briskly at 21° C. for 25 h. The reaction mixture was then washed with ethyl acetate (50 ml), then cooled in ice and covered with ethyl acetate (50 ml). The mixture was acidified to pH 2 with 2N-hydrochloric acid and the aqueous layer was extracted with more ethyl acetate (2×25 ml). The combined organic layers were washed with brine (50 ml), dried ($Na_2SO_4$) and evaporated to give the title compound (2.318 g) as white crystals. A small amount was recrystallised from hexane to give an analytical sample (0.13 g), m.p.72° to 73° C. Analysis found C, 58.1, H, 7.7%; $C_9H_{14}O_4$ requires C, 58.05, H, 7.6%.

Preparation 42

[3aR-(3aα,4α,6aα)]-(Tetrahydro-2,2dimethyl-4H-cyclopenta-1,3-dioxol-4-yl)carbamic acid, phenylmethyl ester A solution of [3aR-(3aα,4α,6aα)]-tetrahydro-2,2-dimethyl-4H-cyclopenta-1,3-dioxole-4-carboxylic acid (4.27 g, 22.9 mmol) in dry 1,4-dioxan (100 ml) under nitrogen was treated with benzyl alcohol (4.75 ml, 45.88 mmol), triethylamine (3.20 ml, 22.94 mmol) and diphenylphosphoryl azide (4.94 ml, 22.94 mmol). The resulting solution was stirred and heated at 90° C. overnight, then allowed to cool to 21° C., concentrated in vacuo and the residue dissolved in ethyl acetate (100 ml) and washed with 1N-hydrochloric acid. The aqueous layer was extracted with ethyl acetate (100 ml) and the combined organic extracts were washed with brine, dried ($Na_2SO_4$), and evaporated to an oil. In order to remove excess benzyl alcohol as benzyl acetate, the oil was dissolved in dichloromethane (150 ml), cooled to 5° to 10° C. and treated with 4-dimethylaminopyridine (5.6 g, 45.9 mmol) and acetic anhydride (4.33 ml, 45.9 mmol). The resulting solution was stirred at 21° C. for 1.5 h, then washed with 2N-hydrochloric acid (100 ml). The aqueous layer was extracted with dichloromethane (2×100 ml) and the combined organic extracts were washed (brine, 200 ml), dried ($Na_2SO_4$) and evaporated to an oil which was purified on silica eluting with ether:cyclohexane 2:1 to give the title compound (4.588 g) as a white solid, nmr(δ,$CDCl_3$) 1.30(s,3H), 1.45(s,3H), 1.55(m,1H), 1.75(m,1H), 1.90(dd,1H), 2.10(m,1H), 3.95(t, 1H), 4.45(d,1H), 4.60(m,1H), 4.70(t,1H), 5.10(s,2H), 7.35 (s,5H).

Preparation 43

[3aR-(3aα,4α,6aα)]-Tetrahydro-2,2-dimethyl-4H-cyclopenta-1,3-dioxol-4-amine

A solution of [3aR-(3aα,4α,6aα)]-(tetrahydro-2,2-dimethyl-4H-cyclopenta-1,3-dioxol-4-yl)carbamic acid, phenylmethyl ester (2.0 g, 6.86 mmol) in ethanol (80 ml) was added dropwise to a stirred suspension of 10%-palladium-on-carbon catalyst (0.20 g) in ethanol under nitrogen. The suspension was hydrogenated at 21° C. for 4.5 h, then filtered through celite. The filtrate was evaporated to give the title compound (1.053 g) as a clear oil, nmr(δ, $CDCl_3$) 1.25 to 1.45(m,9H), 1.75 to 2.10(m,3H), 3.40(d,1H), 4.20(d,1H), 4.75(t,1H).

Preparation 44

(S)-3-[[(1,1-Dimethylethoxy)carbonyl]amino]-hexanedioic acid 1-methyl 6-(phenylmethyl) ester 4-Methylmorpholine (2 ml) was added to a solution of t-butoxycarbonyl-L-glutamic acid 5-benzyl ester (6.75 g, 20 mmol) in ethyl acetate (60 ml) at 0° C. i-Butyl chloroformate (2.61 ml, 20 mmol) was then added to give a precipitate and the mixture was stirred for 15 min at 0° C. before filtering through celite into a flask at 0° C. The pad was washed with precooled ethyl acetate. The combined filtrate and wash was treated with diazomethane in ether (30 mmol in 100 ml) over 5 min and the reaction left at 0° C. for 3 h before warming to room temperature. Excess diazomethane was removed by bubbling nitrogen through the solution which was then concentrated to give a yellow gum. The gum was dissolved in methanol (100 ml), treated with silver benzoate (1 g, 4.4 mmol) and triethylamine (10 ml, 70 mmol) then stirred for 2.5 h at room temperature. The black solution was concentrated under reduced pressure and the residue taken up in ethyl acetate (100 ml) then washed with saturated aqueous sodium bicarbonate solution (100 ml), water (100 ml), 1M aqueous potassium hydrogen sulphate solution (2×100 ml) and brine (100 ml). The dried ($MgSO_4$) organic phase was evaporated to leave a yellow oil which was purified by column chromatography on flash silica eluting with a gradient of 15–50% ethyl acetate in cyclohexane to give the title compound (1.972 g) as a white solid which crystallised from cyclohexane m.p.60°–61° C., $[\alpha]_D$ −21° ($CHCl_3$ c=1%).

Preparation 45

(S)-(3-Oxocyclopentyl)carbamic acid 1,1-dimethylethyl ester 2.5M n-Butyllithium in hexane (5.83 ml) was added dropwise to a stirred solution of 1,1,1,3,3,3- hexamethyldisilazane (3.16 ml, 15 mmol) in tetrahydrofuran (30 ml) at 4° C. After 20 min the solution was cooled to -60° C. and (S)-3-[[(1,1-dimethylethoxy)carbonyl]amino]-hexanedioic acid 1-methyl 6-(phenylmethyl) ester (1.522 g, 4.16 mmol) in tetrahydrofuran (10 ml) was added dropwise over 5 min. The solution was stirred for 10 min before the addition of pH7 buffer (5 ml) and the mixture was then diluted with dichloromethane (200 ml) and pH7 buffer (300 ml). The aqueous phase was adjusted to pH6.5 with 2M hydrochloric acid and then the organic phase was separated. The aqueous phase was extracted with dichloromethane (2×200 ml) and the combined organic phase was dried ($MgSO_4$) then evaporated to leave a solid. The solid was dissolved in ethanol (45 ml) and hydrogenated over 10% palladium-on-carbon (0.5 g) for 4 h. The hydrogen was replaced by nitrogen and the reaction was stirred for a further 18 h then filtered through celite and the pad was washed with ethanol. The filtrate and washings were combined and evaporated to leave a solid which was purified by column chromatography on flash silica eluting with 25–40% ethyl acetate in cyclohexane to give the title compound (0.437 g) as a white solid which crystallised from isopropyl ether, m.p. 97°–98° C., $[\alpha]_D$ -48° ($CHCl_3$ c=0.52%).

Preparation 46

(1S-trans)-(3-Hydroxycyclopentyl)carbamic acid 1,1-dimethylethyl ester

A 1M solution of lithium tris(1,2-dimethylpropyl)borohydride in tetrahydrofuran (1.99 ml) was diluted with tetrahydrofuran (3 ml), cooled to -78° C. and treated dropwise with a solution of (S-3-oxocyclopentyl)carbamic acid 1,1-dimethylethyl ester (0.38 g, 1.66 mmol) in dry tetrahydrofuran (2 ml) at 0° C. The reaction was stirred for 2 h at -78° C. then allowed to warm to room temperature over 1 h. Water (2 ml) was added dropwise then the mixture was diluted with water (20 ml) and ethyl acetate (30 ml). The organic phase was washed with water (20 ml), dried ($MgSO_4$) and evaporated to give impure product which was purified by chromatography on flash silica eluting initially with 15% ethyl acetate in cyclohexane and progressing to neat ethyl acetate. Early fractions gave (1S-cis)-(3-hydroxycyclopentyl)carbamic acid 1,1-dimethylethyl ester (0.16 g) as an oil, nmr (d,$CDCl_3$) 1.43(s,9H), 1.50–2.10(m, 6H), 3.97–4.10(m,1H), 4.32–4.40(m,1~H), 5.00–5.12(m, 1H).

Later fractions gave the title compound (0.124 g) as a solid which was crystallised from diisopropyl ether m.p. 83°–85° C., $[\alpha]_D$ +1.4° ($CHCl_3$ c=0.54%).

Preparation 47

(1S-trans)-[3-(Formyloxy)cyclopentyl]carbamic acid 1,1-dimethylethyl ester

Diethyl azodicarboxylate (0.164 ml, 1.23 mmol) was added dropwise to a stirred solution of (1S-cis)-(3-hydroxycyclopentyl)carbamic acid 1,1-dimethylethyl ester (0.124 g, 0.61 mmol), triphenylphosphine (0.323 g, 1.23 mmol) and formic acid (0.046 ml, 1.23 mmol) and the solution was stirred at room temperature for 2 h The solution was then concentrated and purified by column chromatography on flash silica eluting with 10–30% ethyl acetate in cyclohexane to give the title compound (0.07 g) as white needles from diisopropyl ether m p.84°–85° C., $[\alpha]_D$ -12.7° ($CHCl_3$ c=0.55%).

Preparation 48

(1S-trans)-(3-Hydroxycyclopentyl)carbamic acid 1,1-dimethylethyl ester

A solution of (1S-trans)-[3-(formyloxy)cyclopentyl]carbamic acid 1,1-dimethylethyl ester (0.081 g, 0.35 mmol) in methanol (3 ml) was treated with a slurry of potassium hydrogen carbonate (0.707 g, 7.06 mmol) in water (1.5 ml) and stirred at room temperature for 2 h. The mixture was then diluted with water (20 ml) and ethyl acetate (20 ml) and the aqueous phase was extracted with ethyl acetate (2×20 ml). The combined organic phase was dried ($MgSO_4$) and evaporated to leave a solid which was purified by column chromatography on flash silica eluting with 30–40% ethyl acetate in cyclohexane to give the title compound (0.037 g) from diisopropyl ether m.p. 83°–85° C., $[\alpha]_D$ 0.0° ($CHCl_3$ c=0.55%).

Preparation 49

(S)-[1-[[(Methylsulphonyl)oxy]methyl]-2-phenylethyl]carbamic acid phenylmethyl ester Methanesulphonyl chloride (6.45 ml) was added to a stirred solution of (S)-[1-(hydroxymethyl)-2-phenylethyl]carbamic acid phenylmethyl ester[1] (12.0 g, 0.042 mole) and triethylamine (11.7 ml) in acetone (190 ml). On complete addition the mixture was stirred for 0.5 h then diluted with water (700 ml) and ethyl acetate (600 ml). The aqueous phase was extracted with ethyl acetate (2×500 ml) and the combined organic solution was washed with water (2×500 ml), dried ($MgSO_4$) and evaporated to leave a solid which was purified by flash chromatography using 40–60% ethyl acetate in cyclohexane to give the title compound (13.95 g), $MH^+$=364.

1. A. Correa et al., *Synth.Commun.*, 1991, 21(1), 1.

Preparation 50

(S)-[1-(Azidomethyl)-2-phenylethyl]carbamic acid phenylmethyl ester

A solution of (S)-[1-[[(methylsulphonyl)oxy]methyl]-2-phenylethyl]carbamic acid phenylmethyl ester (2.0 g, 5.5 mmol) in dimethylformamide (35 ml) was heated with sodium azide (0.43 g, 6.6 mmol) at 80° C. for 4.5 h. The reaction was then cooled and poured into iced water (100 ml) and ethyl acetate (70 ml). The aqueous phase was extracted with ethyl acetate (2×70 ml) and the combined extract was washed with water (50 ml), dried ($MgSO_4$) and evaporated to leave an oil which was purified by flash chromatography eluting with 20% ethyl acetate in cyclohexane to give the title compound (1.51 g) as an oil, $MH^+$=312.

Preparation 51

(S)-[1-(Aminomethyl)-2-phenylethyl]carbamic acid phenylmethyl ester

A solution of (S)-[1-[(azidomethyl)-2-phenylethyl]carbamic acid phenylmethyl ester (0.104 g, 0.323 mmol) in ethanol (5 ml) was hydrogenated over 10% palladium-on-carbon (0.019 g) by bubbling hydrogen through for 20 min. The catalyst was removed by filtration and the filtrate was evaporated to leave an oil which was taken up in ethyl acetate (15 ml) and the solution was filtered. The filtrate was evaporated to give the title compound (0.102 g) as an oil which solidified on standing, $MH^+$=284.

Preparation 52

(S)-[1-[[[(1,1-Dimethylethoxy)carbonyl]amino]methyl]-2-phenylethyl]carbamic acid phenylmethyl ester Water (80 ml), sodium carbonate (3.91 g, 3.69 mmol) and di-t-butyl pyrocarbonate (8.05 g, 3.69 mmol) were added to a solution of (S)-[1-(aminomethyl)-2-phenylethyl]carbamic acid phenylmethyl ester (3.5 g, 12.3 mmol) in 1,4-dioxan (80 ml) and the mixture was stirred for 3.3 h. Ethyl acetate (500 ml) and water (500 ml) were added and the aqueous phase was extracted with ethyl acetate (2×500 ml). The combined organic phase was dried (MgSO$_4$) and evaporated to leave a solid which was purified by column chromatography on flash silica eluting with 10–27% ethyl acetate in cyclohexane to give the title compound (3.093 g) as a solid, nmr($\delta$,CDCl$_3$) includes 1.42(s,9H), 2.76 and 2.82–2.93(dd and m,2H), 3.1–3.3(m,2H), 3.87–4.0(m,1H), 5.08(s,2H), 7.1–7.4(m,10H).

Preparation 53

(S)-(2-Amino-3-phenylpropyl)carbamic acid 1,1-dimethylethyl ester

A mixture of (S)-[1-[[[(1,1-dimethylethoxy)carbonyl]amino]methyl]-2-phenylethyl]carbamic acid phenylmethyl ester (2.89 g, 7.51 mmol) and 10% Pd—C (0.171 g) in ethanol (70 ml) was stirred under hydrogen for 2 days. The reaction mixture was filtered through celite and the filtrate was evaporated to leave the title compound (2.18 g) as a solid, nmr($\delta$,CDCl$_3$) includes 1.43(s,9H), 2.5–2.62 and 2.83(m and dd,2H), 3.0 and 3.1–3.25(m,2H), 3.25–3.4(m, 1H), 5.0–5.15(m,1H), 7.15–7.35(m,5H).

Preparation 54

(S)-[1-(Hydroxymethyl)-2-(3-pyridinyl)ethyl] carbamic acid 1,1-dimethylethyl ester A mixture of (S)-[2-[[(1,1-dimethylethoxy)carbonyl]amino]-3-3-pyridinyl)]propionic acid (1.804 g, 6.77 mmol) in dry tetrahydrofuran (30 ml) was cooled to −10° C. and treated dropwise with 4-methylmorpholine (0.74 ml, 6.77 mmol) and after 5 min with ethyl chloroformate (0.65 ml, 6.77 mmol). The solution was stirred for 25 min then added in portions after filtration to a stirred solution of sodium borohydride (0.64 g, 16.1 mmol) in water (25 ml) at 0° C. The reaction was stirred for 25 min then allowed to warm to room temperature over 3 h. The pH of the solution was adjusted to pH3 with 2M hydrochloric acid and stirred for 0.7 h before bringing the pH to 7 with sodium hydrogen carbonate solution. The mixture was extracted with ethyl acetate (3×150 ml) and the extract was dried (MgSO$_4$) and evaporated to dryness. The residue was purified by column chromatography on flash silica eluting with dichloromethane:ethanol:0.880 ammonia (100:8:1). Impure fractions from this column were repurified and added to the pure fractions from the column to give the title compound (1.274 g) as a solid, nmr($\delta$,CDCl$_3$) includes 1.4(s,9H), 2.8–2.95(m, 2H), 3.61(m,2H), 3.8–3.9(m,1H), 4.8–4.9(m,1H), 7.2–7.3, 7.6 and 8.45–8.52(m,d,m,4H).

Preparation 55

(S)-$\beta$-Amino-3-pyridinepropanol dihydrochloride

To a solution of (S)-[1-(hydroxymethyl)-2-(3-pyridinyl) ethyl]carbamic acid 1,1-dimethylethyl ester (1.27 g, 5.03 mmol) in 1,4-dioxan (3 ml) was added 1,4-dioxan saturated with HCl gas (10 ml) followed by a further portion of 1,4-dioxan (10 ml). After 2 h at room temperature the precipitated solid was collected by filtration, washed with 1,4-dioxan (5 ml) and ether then dried in vacuo to give the title compound (0.928 g) as a solid, nmr($\delta$,DMSO-d6) includes 3.11(bd,2H), 3.4–3.7(m,3H), 7.86(dd,1H), 8.1–8.3 (bs,3H), 8.45(d,1H), 8.81(d,1H), 8.9(s,1H).

Preparation 56

(3a$\alpha$,5$\alpha$,6a$\alpha$)-(Tetrahydro-2,2-dimethyl-4H-cyclopenta-1,3-dioxol-5-yl)carbamic acid, phenylmethyl ester A solution of (3a$\alpha$,5$\alpha$,6a$\alpha$)-tetrahydro-2,2-dimethyl-4H-cyclopenta-1,3-dioxole-5-carboxylic acid[1] (2.00 g, 10.74 mmol) in dry 1,4-dioxan under nitrogen was treated with benzyl alcohol (2.22 ml, 21.5 mmol), triethylamine (1.50 ml, 10.74 mmol) and diphenylphosphoryl azide (2.31 ml, 10.74 mmol). The resulting solution was stirred in an oil bath at 90° C. overnight and was then allowed to cool to 21° C. The mixture was evaporated, and the residue was partitioned between ethyl acetate (80 ml) and 1N hydrochloric acid (80 ml). The aqueous layer was extracted with fresh ethyl acetate (50 ml) and the total organic solution was washed (brine, 100 ml), dried (Na$_2$SO$_4$) and evaporated to a pale yellow oil (7.24 g). The oil was purified on silica, eluting with diethyl ether:cyclohexane (2:1) to give the title compound (2.055 g) as a white solid, nmr($\delta$,CDCl$_3$) 1.25(s,3H), 1.3 to 1.5(m,2H), 1.45(s,3H), 2.25(dd,2H), 4.25(m,1H), 4.5 to 4.7(m,3H), 5.10(s,2H), 7.3 to 7.4(m,5H).

[1] W. H. Rastetter and D. P. Phillion, *J. Org. Chem.*, 1981, 46, 3204

Preparation 57

(3a$\alpha$,5$\alpha$,6a$\alpha$)-Tetrahydro-2,2-dimethyl-4H-cyclopenta-1,3-dioxol-5-amine A solution of (3a$\alpha$,5$\alpha$,6a$\alpha$)-(tetrahydro-2,2-dimethyl-4H-cyclopenta-1,3-dioxol-5-yl)carbamic acid, phenylmethyl ester (2.05 g, 7.06 mmol) in ethanol (50 ml) was added dropwise to a stirred suspension of 10% palladium-on-carbon (0.210 g) in ethanol under nitrogen. The mixture was then stirred and hydrogenated overnight. The mixture was filtered through celite and the filtrate was evaporated to give the title compound (1.24 g) as a pale yellow oil which solidified on standing at 4° C., m.p. 55° to 57° C., nmr($\delta$, CDCl$_3$) includes 1.25(s,3H), 1.2 to 1.5(m,2H), 1.45(s,3H), 2.10(dd,2H), 3.60(m,1H), 4.52(m,2H).

Preparation 58

(1$\alpha$,2$\alpha$,4$\beta$)-4-Amino-1,2-cyclopentanediol, hydrochloride

A solution of (3a$\alpha$,5$\alpha$,6a$\alpha$)-(tetrahydro-2,2-dimethyl-4H-cyclopenta-1,3-dioxol-5-yl)carbamic acid, phenylmethyl ester (Preparation 56) in ethanol (70 ml) was added dropwise to 10% palladium-on-carbon (0.190 g) under dry nitrogen. The mixture was hydrogenated at 21° C. overnight and then filtered through celite. The filtrate was treated with 2.5M hydrogen chloride in ethanol (20 ml) and water (2 ml), and the mixture was heated at 65° C. for 3.5 h The mixture was evaporated and the residue was treated with more 2.5M hydrogen chloride in ethanol (15 ml) and water (1 ml) The solution was heated at 65° C. for 2 h, then it was evaporated to a white solid (0.995 g). The solid was recrystallised from methanol/ethyl acetate to give the title compound (0.373 g) as white crystals, nmr($\delta$,DMSO-d6) 1.6 to 1.8(m,2H), 1.8 to 2.0(m,2H), 3.60(m,1H), 4.00(s,2H), 4.60(br.s,1H), 8.05(br.s, 3H).

Preparation 59

5-Amino-1H-tetrazoleethanamine

A mixture of 5-aminotetrazole (6.0 g, 58.2 mmol) and solid sodium hydroxide (8.36 g, 208 mmol) in acetonitrile (30 ml) was stirred for 0.5 h. 2-Chloroethylamine hydrochloride (7.26 g, 62.4 mmol) and tetrabutylammonium hydrogen sulphate (0.788 g, 2.32 mmol) were added and the reaction was heated at reflux for 18 h. The mixture was filtered and the filtrate was evaporated to leave an oil which was taken up in 48% aqueous HBr. The solution was diluted with ethanol (150 ml) and then evaporated to leave an oil which soon solidified. The solid was bleached with hot ethanol leaving a brown gum which was dissolved in water and the solution was evaporated to dryness to give a solid (1.62 g) after drying. The ethanol was reduced in volume and allowed to crystallise. The resulting solid (0.879 g) and the solid from the aqueous solution were combined and stirred in ethanol with a slight excess of sodium hydroxide until a clear solution was obtained. This solution was preabsorbed onto flash silica and purified by elution with dichloromethane:ethanol:0.88 ammonia (100:8:1) to (30:8:1). Fractions with product were evaporated to leave the title compound (0.217 g) as an oil. MH$^+$=129.

Preparation 60

(trans)-(4-Aminocyclohexyl)carbamic acid phenylmethyl ester

A solution of trans 1,4-cyclohexanediamine (22.8 g, 200 mmol) in dry dioxan (100 ml) was cooled to 5°–10° and treated dropwise with 1-[[(phenylmethoxy)carbonyl]oxy]-2,5-pyrrolidinedione (4.98 g, 20 mmol) in dioxan (50 ml) over 3 h. The mixture was warmed to 21° then stirred for a further 2 h and filtered. The filtrate was evaporated to give a solid which was purified on silica eluted with dichloromethane:ethanol:0.88 ammonia (30:8:1) to give the title compound (2.58 g) as a white solid. MH$^+$=249.

Preparation 61 trans-(4-N,N-Dimethylaminocyclohexyl)carbamic acid phenylmethyl ester

A solution of (trans)-(4-amino-cyclohexyl)carbamic acid phenylmethyl ester (0.2 g, 0.805 mmol) in formaldehyde (5 ml) and formic acid (0.1 ml) was heated at reflux for 1.5 h. More formaldehyde (2.5 ml) was added and the reaction continued for a further 2.5 h. The cooled mixture was poured into saturated sodium bicarbonate solution (50 ml) and extracted with ethyl acetate (3×30 ml). The combined organic extract was washed with water (2×30 ml), dried (MgSO4) and evaporated to give an oil which was purified on silica eluted with dichloromethane:ethanol:0.88 ammonia (30:8:1) to give the title compound as an oil. MH$^+$=279.

Preparation 62 trans-(4-N,N-Dimethylamino)cyclohexylamine

A solution of trans-(4-N,N-dimethylaminocyclohexyl)carbamic acid phenylmethyl ester (0.245 g, 0.887 mmol) in ethanol (10 ml) was hydrogenated over 10% palladium-on-carbon (0.03 g) for 50 h with two further changes of catalyst (0.05 g each). The reaction mixture was filtered and the catalyst was washed with ethanol. Evaporation of the filtrate and wash gave the title compound (0.97 g) as an oil, nmr($\delta$,CDCl$_3$) includes 1.0–1.05(m,2H), 1.1–1.4(m,2H), 1.4–1.8(m,2H), 1.8–2.05(m,4H), 2.05–2.25(m,1H), 2.27(s, 6H), 2.58–2.72(m,1H).

Preparation 63

(1S-cis)-[3-[(Methylsulphonyl)oxy]cyclopentyl] carbamic acid 1,1-dimethylethyl ester Methanesulphonyl chloride (0.98 ml, 12.6 mmol) was added to a stirred mixture of (1S-cis)-(3-hydroxycyclopentyl)carbamic acid 1,1-dimethylethyl ester (1.41 g, 7.01 mmol) and triethylamine (1.76 ml, 12.6 mmol) in acetone(55 ml) at 4° C. The resulting mixture, containing a white precipitate, was stirred at 4° C. for one hour, then at 21° C. for a further 2.25 h, after which it was diluted with water(150 ml) and extracted with ethyl acetate (3×100 ml). The total organic solution was washed with water (50 ml), dried (MgSO$_4$) and evaporated to a white solid. This was dissolved in hot diethyl ether (25 ml) and cooled to 4° C. for 2 h, after which time, cyclohexane (25 ml) was added which caused a precipitate to form immediately. The mixture was left to stand at 4° C. for a further 3 h, after which the solid was filtered off, washed with cold cyclohexane/diethyl ether (2:1), then dried to give the title compound (1.202 g) as a white solid, m.p. 88°–89° C., [$\alpha$]$_D$ −11.11° (CHCl$_3$ c=0.54%).

Preparation 64

(1S-trans)-[3-(N,N-Dimethylamino)cyclopentyl] carbamic acid 1,1-dimethylethyl ester (1S-cis)-[3-[(Methylsulphonyl)oxy]cyclopentyl]carbamic acid 1,1-dimethylethyl ester (1.452 g, 5.20 mmol) in a solution of dimethylamine (33% in ethanol, 25 ml) was heated at reflux for 3.75 h, then allowed to cool. The solution was diluted with water (100 ml) and extracted with ethyl acetate(3×100 ml). The total organic solution was dried (Na$_2$SO$_4$) and evaporated to a yellow gum. This was purified on silica, eluting with dichloromethane:ethanol:0.88 ammonia (100:8:1) changing to (30:8:1) to give a brown film (0.988 g, 83%). A portion of this was evaporated from a solution in isopropyl ether to give the title compound (0.139 g) as a brown solid, m.p. 65°–67° C., [$\alpha$]$_D$−40.35°(CHCl$_3$ c=0.57%).

Preparation 65

(1S-trans)-3-(N,N-Dimethylamino)cyclopentylamine dihydrochloride salt (1-S-trans)-[3-(N,N-Dimethylamino)cyclopentyl] carbamic acid 1,1-dimethylethyl ester (0.537 g, 2.35 mmol) in 1,4-dioxan (4 ml) was treated with a saturated solution of hydrogen chloride in 1,4-dioxan (15 ml) and additional 1,4-dioxan (8 ml). After 50 minutes at 21° C., another portion of a saturated solution of hydrogen chloride in 1,4-dioxan (5 ml) was added, and after a further 2.5 h, the opaque solution was concentrated by evaporation to give the title compound as a beige solid, which was used without characterisation.

Preparation 66

6-Amino-2-pyridinemethanamine

A solution of 6-acetylaminopyridine-2-carboxaldehyde[1] (0.65 g, 3.96 mmole) in ethanol (150 ml) was saturated with ammonia and hydrogenated over 10% Pd—C (0.32 g) for 24 h. The catalyst was removed by filtration through kieselguhr and the catalyst was washed with ethanol (2×50 ml). The filtrate and wash were evaporated to leave a solid which was taken up in 2M sodium hydroxide solution (20 ml) and heated at 60° for 2 h. The cooled mixture was evaporated to low bulk (~1.5 ml) and extracted with dichloromethane (5×20 ml). The extract was dried (MgSO$_4$) and evaporated to leave the crude title compound as an oil which was used without further purification.

1. Abarca, B., et al., *Tetrahedron*, 1989, 45(22), 7041.

Example 1

(1S-trans)-1-Deoxy-1-[6-[(2,2-diphenylethyl)amino]-2-[(3-hydroxycyclopentyl)amino]-9H-purin-9-yl]-N-ethyl-2,3-O-(1-methylethylidene)-β-D-ribofuranuronamide (1S-trans)-N-(3-Hydroxycyclopentyl)carbamic acid 1,1-dimethylethyl ester (0.138 g, 0.69 mmol) in 1,4-dioxan (2 ml) was treated with a saturated solution of hydrogen chloride in 1,4-dioxan (2 ml) for 0.5 h. The solution was evaporated to dryness, azeotroped with methanol (2×5 ml), then dissolved in methanol (4 ml) and added to a solution of sodium hydroxide (0.011 g, 0.65 mmol) in methanol (4 ml). The methanol was blown off with nitrogen and the resulting film was dissolved in dimethylsulphoxide (0.5 ml). This solution was added to 1-[2-chloro-6-[(2,2-diphenylethyl)amino]-9H-purin-9-yl-]-1-deoxy-N-ethyl-2,3-O-(1-methylethylidene)-β-D-ribofuranuronamide (0.127 g, 0.69 mmol) and the mixture was heated at 140° C. for 27 h. The cooled mixture was diluted with ethyl acetate (40 ml) and water (40 ml) and the organic phase was washed with water (30 ml), dried (MgSO$_4$) and evaporated to leave an oil which was purified by column chromatography on flash silica eluting initially with 60% ethyl acetate in cyclohexane and progressing to neat ethyl acetate to give the title compound (0.029 g) which crystallised from ethyl acetate/cyclohexane MH$^+$=628, [α]$_D$+1.9° (CHCl$_3$ c=0.53%).

Example 2

(1S-trans)-1-Deoxy-1-[6-[(2,2-diphenylethyl)amino]-2-[(3-hydroxycyclopentyl)amino]-9H-purin-9-yl]-N-ethyl-β-D-ribofuranuronamide hydrochloride salt A solution of (1S-trans)-1-deoxy-1-[6-[(2,2-diphenylethyl)amino]-2-[(3-hydroxycyclopentyl)amino]-9H-purin-9-yl]-N-ethyl-2,3-O-(1-methylethylidene)-β-D-ribofuranuronamide (0.01 g, 0.02 mmol) in 1,4-dioxan (1.5 ml) was treated with 6M-aqueous hydrochloric acid (3 ml) and the solution was left to stand for 4 days before evaporating to leave the title compound (0.029 g) as a glassy solid, MH$^+$=588, nmr((δ,CDCl$_3$) includes 1.02(t,3H), 1.4–1.6, 1.6–1.8, 1.85–2.05, 2.1–2.25(ms,6H), 3.1–3.2(m,2H), 4.35 (s,1H), 5.85–5.9(m,1H), 7.1–7.4(m,10H).

Example 3

[trans-(±)]-1-Deoxy-1-[6-[(2,2diphenylethyl)amino]-2-[(3-hydroxycyclopentyl)amino]-9H-purin-9-yl]-N-ethyl-2,3-O-(1-methylethylidene)-β-D-ribofuranuronamide A solution of 1-[2-chloro-6-[(2,2-diphenylethyl)amino]-9H-purin-9-yl]-1-deoxy-N-ethyl-2,3-O-(1-methylethylidene)-β-D-ribofuranuronamide (0.7 g, 1.24 mmol) and trans-(±)-3-aminocyclopentanol[1] (0.844 g, 7.23 mmol) in dimethylsulphoxide (3 ml) was heated at 140° C. for 24 h. The solution was diluted with ethyl acetate (90 ml), washed with water (3×100 ml) then dried (MgSO$_4$) and evaporated to leave a froth which was purified by column chromatography on flash silica initially eluting with 65% ethyl acetate in cyclohexane and progressing to neat ethyl acetate to give the title compound (0.498 g) as a froth MH$^+$=628, nmr(δ,CDCl$_3$) includes 0.705–0.715(ts,3H), 1.4 (s,3H) and 1.59(s,3H), 1.55–2.3(ms,6H), 2.9–3.05(m,2H), 4.15–4.55(ms,5H); 4.65(bd,1H), 5.5–5.6(m,1H), 5.6–5.7(m, 1H), 5.99(d,1H), 7.2–7.4(m,10H), 7.41(s,1H).
1. Published European Application EP-A-322242.

Example 4

[trans-(±)]-1-Deoxy-1-[6-[(2,2-diphenylethyl)amino]-2-[(3-hydroxycyclopentyl)amino]-9H-purin-9-yl]-N-ethyl-β-D-ribofuranuronamide A solution of [trans-(±)-1-deoxy-1-[6-[(2,2-diphenylethyl)amino]-2-[(3-hydroxycyclopentyl)amino]-9H-purin-9-yl]-N-ethyl-2,3-O-(1-methylethylidene)-β-D-ribofuranuronamide (0.137 g, 0.218 mmol) in 95:5 trifluoroacetic acid:water (5 ml) was kept at room temperature for 4 h then the solvent was removed by evaporation. The residue was purified by preparative HPLC (30–70% acetonitrile) to give the title compound (0.033 g), nmr(δ, DMSO-d6) includes 1.0(t,3H), 1.5(m,2H), 1.6–1.8(m,1H), 1.8(m,2H), 2.0–2.3(m,1H), 3.15(m,2H), 4.0–4.4(m,6H), 4.4–4.47(m,3H), 5.85(d,1H), 7.1–7.4(m,10H), 8.1–8.4(m, 2H).

Example 5

(1R-trans)-1-Deoxy-1-[6-[(2,2diphenylethyl)amino]-2-[(3-hydroxycyclopentyl)amino]-9H-purin-9-yl]-N-ethyl-β-D-ribofuranuronamide and (1S-trans)-1-deoxy-1-[6-[(2,2-diphenylethyl)amino]-2-[(3-hydroxycyclopentyl)amino]-9H-purin-9-yl]-N-ethyl-β-D-ribofuranuronamide A solution of [trans-(±)]-1-deoxy-1-[6-[(2,2-diphenylethyl)amino]-2-[(3-hydroxycyclopentyl)amino]-9H-purin-9-yl]-N-ethyl-2,3-O-(1-methylethylidene)-β-D-ribofuranuronamide (0.433 g, 0.69 mmol) in 1,4-dioxan (9 ml) was stirred with 2M hydrochloric acid (11 ml) for 25 h. More acid (4M,2 ml) was added and the mixture was kept at 3° for 65 h before evaporating to leave a solid which was purified by preparative HPLC (39% acetonitrile for 16 min then up to 42% over 5 min and up to 45% over 1 min) to give the (1R) isomer (0.142 g) as a solid from ether MH$^+$=588, nmr(d,$_1$DMSO-d6) includes 1.01(t,3H), 1.4–1.6, 1.6–1.8, 1.8–2.0, 2.1–2.25(ms,6H), 3.1–3.25(m,2H), 4.3(s,1H), 5.85 (bd,1H), 7.1–7.4(m,10H), 8.15(bs,1H), then the (1S) isomer (0.14 g) as a solid from ether MH$^+$=588, nmr(δ,DMSO-d6) includes 1.01(t,3H), 1.4–1.6, 1.6–1.8, 1.8–2.0, 2.1–2.25(ms, 6H), 3.1–3.25(m,2H), 4.3(s,1H), 5.84(bd,1H), 7.15–7.4(m, 10H), 8.03(bs,1H).

Example 6

[3aR-(3aα,4α,6aα)]-1-Deoxy-1-[6-[(2,2-diphenylethyl)amino]-2-tetrahydro-2,2-dimethyl-4H-cyclopenta-1,3-dioxol-4-amino)-9H-purin-9-yl]-N-ethyl-2,3-O-(1-methylethylidene)-β-D-ribofuranuronamide.

A mixture of 1-[2-chloro-6-[(2,2-diphenylethyl)amino]-9H-purin-9-yl]-1-deoxy-N-ethyl-2,3-O-(1-methylethylidene)-β-D-ribofuranuronamide (0.346 g, 0.614 mmol) and [3aR-(3aα,4α,6aα)]-tetrahydro-2,2-dimethyl-4H-cyclopenta-1,3-dioxol-4-amine (0.965 g, 6.14 mmol) was dissolved in dimethylsulphoxide (1.8 ml), and the solution was stirred and heated at 140° C. under nitrogen for 11 h. The mixture was allowed to cool to 21° C. and was then partitioned between ethyl acetate (50 ml) and water (50 ml). The organic layer was washed with water and the combined aqueous layers were extracted with ethyl acetate (2×30 ml). The combined organic extracts were washed (brine), dried (Na$_2$SO$_4$) and evaporated. The residue was purified on silica eluting with ethyl acetate:cyclohexane (9:1), and then repurified on silica eluting with ethyl acetate:cyclohexane (3:1) to give the title compound (0.302 g) as a cream foam, MH$^+$=684.

Similarly prepared was:

[(3aα,4α,6aα)-(±)]-1-deoxy-1-[6-[(2,2-diphenylethyl) amino]-2-(tetrahydro-2,2-dimethyl-4H-cyclopenta-1,3-dioxol-4-amino)-9H-purin-9-yl]-N-ethyl-2,3-O-(1-methylethylidene)-β-D-ribofuranuronamide from the 2-chloropurine (0.269 g) and [(3aα,4α,6aα)-(±)]-tetrahydro-2,2-dimethyl-4H-cyclopenta-1,3-dioxol-4-amine (0.75 g) in dimethylsulphoxide (1.5 ml) at 140° C. for 20 h. The product was purified on silica eluting with ethyl acetate-:cyclohexane 9:1, MH$^+$=684.

Example 7

[1S-(1α,2β,3β)]-1-Deoxy-1-[2-[(2,3-dihydroxycyclopentyl)amino]-6-[(2,2-diphenylethyl) amino]-9H-purin-9-yl]-N-ethyl-β-D-ribofuranuronamide

[3aR-(3aα,4α,6aα)]-1-Deoxy-1-[6-[(2,2-diphenylethyl) amino]-2-(tetrahydro-2,2-dimethyl-4H-cyclopenta-1,3-dioxol-4-amino)-9H-purin-9-yl]-N-ethyl-2,3-O-(1-methylethylidene)-β-D-ribofuranuronamide (0.13 g, 0.19 mmol) was treated with trifluoroacetic acid (1 ml) and water (0.25 ml), and the resulting solution was left to stand at 21° C. for 1.5 h. The reaction mixture was evaporated, and the residue was purified on silica eluting with dichloromethane:methanol (9:1) to give the title compound (0.080 g) as a cream foam, MH$^+$=604.(δ,DMSO-d6) 1.00(t,3H), 1.35(m,1H), 1.55(m,1H), 1.85(m,1H), 2.20(m,1H), 3.15(m,1H), 3.75(m,1H), 3.90 to 4.25(m,6H), 4.40(m,1H), 4.65(m,2H), 5.50(d,1H), 5.60(d,1H), 5.80(d,1H), 6.35(m,1H), 7.10 to 7.45(m,11H), 7.95(s,1H), 8.15(m,1H).

Example 8

[(1α,2β,3β)-(±)]-1-Deoxy-1-[2-[(2,3-dihydroxycyclopentyl)amino]-6-[(2,2-diphenylethyl) amino]-9H-purin-9-yl]-N-ethyl-β-D-ribofuranuronamide,

[1R-(1α,2β,3β)]-1-deoxy-1-[2-[(2,3-dihydroxycyclopentyl)amino]-6-[(2,2-diphenylethyl) amino]-9H-purin-9-yl]-N-ethyl-β-D-ribofuranuronamide, and

[1S-(1α,2β,3β)]-1-deoxy-1-[2-[(2,3-dihydroxycyclopentyl)amino]-6-[(2,2-diphenylethyl) amino]-9H-purin-9-yl]-N-ethyl-β-D-ribofuranuronamide

[(3aα,4α,6aα)-(±)]-1-Deoxy-1-[6-[(2,2-diphenylethyl) amino]-2-(tetrahydro-2,2-dimethyl-4H-cyclopenta-1,3-dioxol-4-amino)-9H-purin-9-yl]-N-ethyl-2,3-O-(1-methylethylidene)-β-D-ribofuranuronamide (0.222 g) was treated with trifluoroacetic acid (2.5 ml) and water (0.25 ml), and the resulting solution was left to stand at 20° C. for 3 h. The reaction mixture was evaporated, and the residue was stirred with sodium hydrogen carbonate (2.4 g) in ethanol (6 ml) at 20° C. for 1 h. The total filtrate and washings were evaporated and the residue was purified on flash silica eluting with dichloromethane:ethanol:0.880 ammonia (30:8:1) to give the first title compound (0.089 g) as a pale brown solid, MH$^+$=604, Analysis found: C, 59.05, H, 6.1, N, 15.5%; C$_{31}$H$_{37}$N$_7$O$_6$.1.5H$_2$O requires C, 59.05, H, 6.4, N, 15.55%.

A portion (0.060 g) of a product from a similar reaction was purified by preparative HPLC isocratically at 35% acetonitrile. The faster-running component gave the second (1R) title compound (0.015 g) as an off-white solid, MH$^+$=604, nmr(δ,DMSO-d6;400 MHz) includes 1:35(m,1H), 1.55 (m,1H), 1.90(m,1H), 2.25(m,1H), 4.30(s,1H), 4.60(br.s,1H), 4.65(m,1H), 5.85(d,1H).

The slower-moving component gave the third (1S) title compound (0.015 g) as an off-white solid, MH$^+$=604, nmr (δ,DMSO-d6;400 MHz) includes 1.35(m,1H), 1.55(m,1H), 1.90(m,1H), 2.25(m,1H), 4.30(s,1H), 4.60(br.s,1H), 4.65(m, 1H), 5.85(d,1H)., Example 9

[cis-(±)]-1-Deoxy-1-[6-[(2,2-diphenylethyl)amino]-2-[[3-[[(phenylmethoxy)carbonyl]amino] cyclopentyl]amino]-N-ethyl-2,3-O-(1-methylethylidene)-9H-purin-9-yl]-β-D-ribofuranuronamide A mixture of 1-[2-chloro-6-[2,2-(diphenylethyl)amino]-9H-purin-9-yl]-1-deoxy-N-ethyl-2,3-O-(1-methylethylidene)-β-D-ribofuranuronamide (0.3 g, 0.533 mmol) and [cis-(±)]-(3-aminocyclopentyl)carbamic acid phenylmethyl ester (0.41 g) was heated at 140° C. for 4 days. The cooled mixture was dissolved in dichloromethane and purified by column chromatography on flash silica with 50% ethyl acetate in cyclohexane to give the title compound (0.214 g) as a froth, nmr(δ,DMSO-d6) includes 0.55(m,3H), 0.8–1.1(m,2H), 1.1–1.35(m,2H), 1.45(s,3H), 1.5(s,3H), 1.45–1.75(m,2H), 1.75–2.0(m,1H), 2.6–2.95(m,2H), 3.8–4.0(m,1H), 3.95–4.15(m,2H), 4.1–4.3(m,1H), 4.45(s, 1H), 4.5–4.65(m,1H), 5.03(m,2H), 5.3–5.5(m,2H), 6.2(bs, 1H), 6.45(m,1H), 7.1–7.5(m,15H), 7.78(bs,1H).

Example 10

[cis-(±)]-1-[2-[(3-Aminocyclopentyl)amino]-6-[(2,2-diphenylethyl)amino]]-9H-purin-9-yl]-1-deoxy-N-ethyl-β-D-ribofuranuronamide A solution of [cis-(±)]-1-deoxy-1-[6-[(2,2-diphenylethyl) amino]-2-[[3-[[(phenylmethoxy)carbonyl]amino] cyclopentyl]amino]-N-ethyl-2,3-O-(1-methylethylidene)-9H-purin-9-yl]-β-D-ribofuranuronamide (0.15 g, 0.197 mmol) in ethanol (30 ml) was hydrogenated over 10% palladium-on-carbon for 8 h. The catalyst was removed by filtration and washed with ethanol (20 ml) and the combined ethanolic solution was evaporated to leave an oil. The oil was dissolved in ethyl acetate and the solution was filtered before evaporating to an oil. This oil was taken up in trifluoroacetic acid:water (9:1, 5 ml) and the solution was left for 3 h when the solution was evaporated to leave an oil which was purified by reverse phase HPLC (20–60% acetonitrile) to give the title compound (0.073 g) MH$^+$=587, nmr(δ,DMSO-d6) includes 1.02(t,2H), 1.4–1.65(m,1H), 1.6–1.85(m,2H), 1.85–2.1(m,2H), 3.05–3.25(m,2H), 3.4–3.6(m,1H), 4.0–4.15(m,2H), 4.15–4.22(m,1H), 4.28(s, 1H), 4.55–4.7(m,2H), 5.83(d,1H), 7.15–7.4(m,10H), 7.9(bs, 3H), 8.15(m,2H).

Example 11

[trans-(±)]-1-Deoxy-1-[6-[(2,2-diphenylethyl)amino] -2-[[2-[[(phenylmethoxy)carbonyl]amino] cyclopentyl]amino]-N-ethyl-2,3-O-(1-methylethylidene)-9H-purin-9-yl]-β-D-ribofuranuronamide, and separation of the diastereoisomers A mixture of 1-[2-chloro-6-[2,2-(diphenylethyl)amino]-9H-purin-9-yl]-1-deoxy-N-ethyl-2,3-O-(1- methylethylidene)-β-D-ribofuranuronamide (0.31 g, 0.55 mmol) and [trans-(±)]-(2-aminocyclopentyl)carbamic acid phenylmethyl ester (0.77 g, 3.28 mmol) was heated at 140° C. for 24 h. More amine (0.51 g, 2.18 mmol) was added and the heating continued for a further 17 h, then more amine (0.30 g, 1.28 mmol) was added and the heating (140° C.) continued for a further 24 h. The cooled mixture was purified by column chromatography on silica with 20% ethyl acetate in cyclohexane, and then by preparative HPLC (50 to 90% acetonitrile) to give the title compound (isomer 1) (0.067 g) as a grey foam, $MH^+$=761, and as the slower-running component, isomer 2 (0.062 g) as a grey foam, $MH^+$=761.

Example 12

(trans)-1-[2-[(2-Aminocyclopentyl)amino]-6-[(2,2-diphenylethyl)amino]]-9H-purin-9-yl]-1-deoxy-N-ethyl-β-D-ribofuranuronamide, isomer 1

A solution of [trans-(±)]-1-deoxy-1-[6-[(2,2-diphenylethyl)amino]-2-[[2-[[(phenylmethoxy)carbonyl]amino]cyclopentyl]amino]-N-ethyl-2,3-O-(1-methylethylidene)-9H-purin-9-yl]-β-D-ribofuranuronamide, isomer 1 (0.075 g, 0.098 mmol) in ethanol (10 ml) was hydrogenated over 10% palladium-on-carbon (10 mg) for 2 days. The catalyst was removed by filtration and washed with ethanol and the combined ethanolic solution was evaporated to leave a foam (62 mg). The foam (0.058 g) was treated with trifluoroacetic acid (0.75 ml) and water (0.25 ml) and the solution was left for 1.5 h. It was then evaporated to a yellow foam (0.076 g) which was purified by preparative HPLC (20–60% acetonitrile) to give the title compound (0.030 g), $MH^+$=587, nmr(δ,DMSO-d6) 1.00(t,3H), 1.65(m,4H), 2.15(m,2H), 3.15(m,2H), 3.45(m, 1H), 4.00 to 4.35(m,5H), 4.55(m,2H), 5.85(d,1H), 7.00(m, 1H), 7.15 to 7.40(m,10H), 7.90 to 8.25(m,5H).

Similarly prepared was:

(trans)-1-[2-[(2-aminocyclopentyl)amino]-6-[(2,2-diphenylethyl)amino]]-9H-purin-9-yl]-1-deoxy-N-ethyl-β-D-ribofuranuronamide, isomer 2, from the isomer 2 product of Example 11 (0.072 g), which gave 0.065 g of product from hydrogenolysis. 0.058 g of this was treated with aqueous trifluoroacetic acid as above to give 0.031 g of required product, $MH^+$=587, nmr(δ,DMSO-d6) 1.00(t,3H), 1.65(m,4H), 2.15(m,2H), 3.15(m,2H), 3.45(m,1H), 4.00 to 4.30(m,5H), 4.55(m,2H), 5.90(d,1H), 7.15 to 7.40(m,10H), 7.65(m,1H), 8.00(m,2H), 8.20(m,2H).

Example 13

[trans-(±)]-1-[2-[(3-Aminocyclopentyl)amino]-6-[(2,2-diphenylethyl)amino]]-9H-purin-9-yl]-1-deoxy-N-ethyl-β-D-ribofuranuronamide A mixture of 1-[2-chloro-6-[2,2-(diphenylethyl)amino]-9H-purin-9-yl]-1-deoxy-N-ethyl-2,3-O-(1-methylethylidene)-β-D-ribofuranuronamide (0.25 g, 0.44 mmol) and [trans-(±)]-(3-aminocyclopentyl)carbamic acid phenylmethyl ester (0.29 g) were heated for 2 days at 135° C. More amine (0.376 g) was then added and the heating was continued for a further 24 h. Dichloromethane was added to the cooled mixture which was then purified by column chromatography on flash silica eluting with dichloromethane:ethanol:0.880 ammonia (100:8:1) to give [trans-(±)]-1-deoxy-1-[6-[(2,2-diphenylethyl)amino]-2-[[3-[[(phenylmethoxy)carbonyl]amino]cyclopentyl]amino]-9H-purin-9-yl]-N-ethyl-2,3-O-(1-methylethylidene)-β-D-ribofuranuronamide (0.101 g). This compound (0.101 g, 0.133 mmol) in ethanol (10 ml) was hydrogenated over 10% palladium-on-carbon (0.05 g) for 6 h. The catalyst was removed by filtration, washed with ethanol (20 ml) and the combined ethanolic solution was evaporated to leave an oil (0.081 g) which was dissolved in trifluoroacetic acid:water (95:5, 5 ml) and the solution was left for 3 h before evaporating to an oil. The oil was purified by reverse phase HPLC (30–70% acetonitrile) to give the title compound (0.042 g) as a solid from ether $MH^+$=587, nmr(δ,DMSO-d6) includes 1.02(t,2H), 1.47–1.7(m,2H), 1.85–2.05(m,1H), 2.0–2.25(m,2H), 3.05–3.25(m,2H), 3.6–3.75(m,1H), 4.04–4.15(m,2H), 4.18(bs,2H), 4.25(s,1H), 5.85(d,1H), 7.15–7.4(m,12H), 7.82(m,3H), 8.15(m,2H).

Example 14

[1S-trans]-1-[2-[(3-Aminocyclopentyl)amino]-6-[(2,2-diphenylethyl)amino]]-9H-purin-9-yl]-1-deoxy-N-ethyl-β-D-ribofuranuronamide and

[1R-trans]-1-[2-[(3-aminocyclopentyl)amino]-6-[(2,2-diphenylethyl)amino]]-9H-purin-9-yl]-1-deoxy-N-ethyl-β-D-ribofuranuronamide A solution of [trans-(±)]-1-deoxy-1-[6-[(2,2-diphenylethyl)amino]-2-[[3-[[(phenylmethoxy)carbonyl]amino]cyclopentyl]amino]-9H-purin-9-yl]-N-ethyl-2,3-O-(1-methylethylidene)-β-D-ribofuranuronamide (0.601 g, 0.79 mmol) in methanol (50 ml) was stirred under nitrogen and heated at reflux with ammonium formate (0.25 g). After 3 h the cooled mixture was filtered and the filtrate was evaporated to leave [trans-(±)]-1-[2-[(3-aminocyclopentyl)amino]-6-[(2,2-diphenylethyl)amino]]-9H-purin-9-yl]-1-deoxy-N-ethyl-2,3-O-(1-methylethylidene)-β-D-ribofuranuronamide (0.511 g) as a solid.

A portion (0.31 g) was purified by reverse phase HPLC (38% acetonitrile) and the two products were collected and evaporated to leave Isomer I (0.1 g) and Isomer II (0.103 g). These were separately treated with trifluoroacetic acid/water 9/1 (5 ml) and left for 2.5 h. The resulting solutions were evaporated to dryness and the residues were purified by reverse phase HPLC (20–60% acetonitrile) to give the title compounds as solids from ether: Isomer I (0.065 g) $MH^+$=587, nmr(δ,DMSO-6) includes 1.02(t,3H), 1.45–1.7(m,2H), 1.85–2.25(m,3H), 3.05–3.25(m,2H), 4.15(m,1H), 4.27(s, 1H), 4.63(m,2H), 5.84(d,1H), 7.15–7.4(m,10H), 7.84(m, 2H), 8.05–8.2(m,2H). Isomer II (0.61 g) $MH^+$=587, nmr(δ, DMSO-d6) 1.02(t,3H), 1.5–1.7(m,2H), 1.85–2.25(m,3H), 3.05–3.25(m,2H), 4.17(bs,1H), 4.25(s,1H), 4.62(m,2H), 5.84(d,1H), 7.15–7.4(m,10H), 7.84(m,2H), 8.05–8.2(m,2H).

Example 15

[trans-(±)]-1-Deoxy-1-[6-[(2,2-diphenylethyl)amino]-2-[[3-[(trifluoroacetyl)amino]cyclopentyl]amino]-N-ethyl-9H-purin-9-yl]-β-D-ribofuranuronamide Trifluoroacetic anhydride (3×0.047 ml) was added in three portions over 2 h to a stirred mixture of [trans-(±)]-1-[2-[(3-aminocyclopentyl)amino]-6-[(2,2-diphenylethyl)amino]]-9H-purin-9-yl]-1-deoxy-N-ethyl-2,3-O-(1-methythylidene)-β-D-ribofuranuronamide (the initially formed product from Example 14) (0.2 g, 0.32 mmol) and triethylamine (0.15 ml) in dichlormethane (10 ml). After a further 0.5 h the reaction was diluted with ethyl acetate (50 ml) and washed with water (3×20 ml), dried ($MgSO_4$) and evaporated to leave an oil which was dissolved in trifluoroacetic acid water (9:1, 10 ml). The solution was left for 2.5 h then evaporated to leave an oil which was purified by reverse phase HPLC (30–70% acetonitrile) to give the title compound (0.04 g) MH$^+$=683, nmr($\delta$,DMSO-d6) includes 1.05(t,3H), 1.4–1.7(m,2H), 1.7–2.0(m,1H), 1.9–2.3(m,3H), 3.1–3.3(m,2H), 4.05–4.3(m,2H), 4.32(m,1H), 4.5–4.7(m, 2H), 5.87(d,1H), 7.15–7.4(m,10H), 7.95(s,1H).

Example 16

[(trans-(±)]-1-Deoxy-1-[2-[[3-(N,N-dimethylamino) cyclopentyl]]amino]-6-[(2,2-diphenylethyl)amino]-9H-purin-9-yl]-N-ethyl-2,3-O-(1-methylethylidene)-β-D-ribofuranuronamide A solution of 1-[2-chloro-6-[2,2-(diphenylethyl)amino]-9H-purin-9-yl]-1-deoxy-N-ethyl-2,3-O-(1-methylethylidene)-β-D-ribofuranuronamide (0.28 g, 0.05 mmol) and [trans-(±)]-3-(N,N-dimethylamino) cyclopentylamine (0.36 g, 2.81 mmol) in dimethylsulphoxide (2 ml) was heated at 130° C. using a reflux condenser. After 24 h the mixture was cooled and partitioned between ethyl acetate (50 ml) and water (50 ml). The aqueous phase was extracted with ethyl acetate (20 ml) and the combined organic solution was evaporated to leave an oil (0.592 g) which was purified by column chromatography on flash silica eluting with dichloromethane:ethanol:0.880 ammonia (100:8:1) to give the title compound (0.163 g) as a solid, nmr($\delta$,CDCl$_3$) includes 0.7(t,3H), 1.48(s,3H), 1.6(s,3H), 1.2–1.4(m,1H), 1.45–1.7(m,2H), 1.95(m,2H), 2.05(m,2H), 2.3(s,3H), 2.4(s,3H), 2.75–3.0(m,2H), 2.85–3.1(m,1H), 4.1–4.3(m,1H), 2.25–4.5(m,2H), 4.63(s,1H), 4.78(m,1H), 5.5(m,2H), 5,6(d,1H), 6.0(bs,2H), 7.15–7.35(m,10H), 7.4(s, 1H).

Example 17

[(trans)-(±)]-1-[2-[[3-(N,N-dimethylamino) cyclopentyl]amino]-6-[(2,2-diphenylethyl)amino]-9H-purin-9-yl]-N-ethyl-β-D-ribofuranuronamide A solution of [(trans)-(±)]-1-deoxy-1-[2-[[3-(N,N-dimethylamino)cyclopentyl]amino]-6-[(2,2-diphenylethyl) amino]-9H-purin-9-yl]-N-ethyl-2,3-O-(1-methylethylidene) -β-D-ribofuranuronamide (0.15 g, 0.23 mmol) in trifluoroacetic acid:water (9:1, 10 ml) was left at room temperature for 2.5 h then evaporated to leave an oil which was purified by reverse phase HPLC (30–70% acetonitrile) to give the title compound (0.12 g) as a solid from ether, MH$^+$=615, nmr($\delta$,DMSO-d6) includes 1.0(t,3H), 1.55–1.7 (m,2H), 1.95–2.25(m,4H), 2.78(s,6H), 3.12(m,2H), 3.7(m, 1H), 4.1(m,2H), 4.18(m,1H), 4.28(s,1H), 4.4(m,1H), 4.6(m, 2H), 5.85(d,1H), 7.15–7.4(m,10H), 7.72(m,1H), 8.15(bs, 2H), 9.62(m,1H).

Example 18

1-Deoxy-1-[6-[(2,2-diphenylethyl)amino]-2-[[2-(1H-imidazol-4-yl)ethyl]amino]-9H-purin-9-yl]-N-ethyl-2,3-O-(1-methylethylidene)-β-D-ribofuranuronamide A solution of 1-[2-chloro-6-[(2,2-diphenylethyl)amino]-9H-purin-9-yl]-1-deoxy-N-ethyl-2,3-O-(1-methylethylidene)-β-D-ribofuranuronamide (0.25 g, 0.444 mmol) and histamine (0.35 g, 3.15 mmol) in dimethylsulphoxide (2 ml) was heated at 130° C. for 18 h under nitrogen. The cooled mixture was diluted with ethyl acetate (50 ml) and washed with water (2×50 ml), dried (MgSO$_4$) and evaporated to leave a froth which was purified by column chromatography on flash silica eluting with dichloromethane:ethanol:0.880 ammonia (100:8:1) to give the title compound (0.176 g) as a solid from ether, nmr($\delta$,CDCl$_3$) includes 0.4(t,3H), 1.35(s,3H), 1.6(s,3H), 2.65–2.9(m,1H), 2.8–3.05(m,3H), 3.4–3.8(m,3H), 4.05–4.3(bs,2H), 4.32(t, 1H), 4.7(s,1H), 4.95(m,1H), 4.98(m,1H), 5.5(d,1H), 5.72 (dd,1H), 5.97(m,1H), 6.02(s,1H), 6.9(s,1H), 7.15–7.45(m, 10H), 7.43(s,1H), 7.62(s,1H).

Example 19

1-Deoxy-1-[6-[(2,2-diphenylethyl)amino]-2-[[2-(1H-imidazol-4-yl)ethyl]amino]-9H-purin-9-yl]-N-ethyl-β-D-ribofuranuronamide A solution of 1-deoxy-1-[6-[(2,2-diphenylethyl)amino]-2-[[2-(1H-imidazol-4-yl)ethyl]amino]-9H-purin -9-yl]-N-ethyl-2,3-O-(1-methylethylidene)-β-D-ribofuranuronamide (0.126 g, 0.198 mmol) in trifluoroacetic acid:water (9:1, 8 ml) was left for 3 h at room temperature before evaporating to dryness. The resulting oil was treated with ether (20 ml) to give the title compound (0.147 g) as a solid MH$^+$=598, nmr($\delta$,DMSO-6) includes 0.98(t,3H), 2.9–3.05(m,2H), 3.05–3.25(m,2H), 4.3(s,1H), 4.5–4.65(m,2H), 5.84(d,1H), 7.15–7.35(m,10H), 7.42(s,1H), 8.1(s,1H), 9.0(s,1H), 14.0–14.2(m,2H).

Example 20

(1S)-1-Deoxy-1-[6-[(2,2-diphenylethyl)amino]-2-[[1-(hydroxymethyl)-2-phenylethyl]amino]-9H-purin-9-yl]-N-ethyl-2,3-O-(1-methylethylidene)-β-D-ribofuranuronamide (S)-Phenylalaninol (0.403 g, 2.67 mmol) and 1-[2-chloro-6-[(2,2-diphenylethyl)amino]-9H-purin-9-yl]-1-deoxy-N-ethyl-2,3-O-(1-methylethylidene)-β-D-ribofuranuronamide (0.25 g, 0.44 mmol) were heated together for 40 h at 130° C. The cooled mixture was purified by column chromatograph on flash silica eluting with 10–85% ethyl acetate in cyclohexane to give the title compound (0.136 g) as a froth, nmr($\delta$,CDCl$_3$)includes 0.6(t,3H), 1.4(s,3H) and 1.58(s,3H), 2.7–2.85(m,2H), 2.85–3.0(m,2H), 3.47(dd,1H), 3.81(dd, 1H), 4.1–4.5(m,3H), 4.62(s,1H), 5.3(d,1H), 5.69(d,1H), 5.94(s,1H), 7.1–7.4(m,16H).

Similarly prepared were:

1) [cis-(±)]-1-deoxy-1-[6-[(2,2-diphenylethyl)amino]-2-[(2-hydroxycyclopentyl)amino]-9H-purin-9-yl]-N-ethyl-2, 3-O-(1-methylethylidene)-β-D-ribofuranuronamide, using [cis-(±)]-2-aminocyclopentanol[1] as the nucleophile as in entry 1 in Table 1 below. The product was purified on silica eluting with ethyl acetate:cyclohexane (19:1). MH$^+$=628.
1. R. A. B. Bannard et al., Canad. J. Chem., 1971, 49, 2064

2) [trans-(±)]-2-[[6-[(2,2-Diphenylethyl)amino]-9-[N-ethyl-2,3-O-(1-methylethylidene)-β-D-ribofuranuronamidosyl]-9H-purin-2-yl]amino]cyclopentanecarboxylic acid 2,2-dimethylethyl ester, using (±)-trans-2-aminocyclopentanecarboxylic acid 1,1-dimethylethyl ester[1] as the nucleophile as in entry 2 in Table 1 below. The product was purified on silica eluting with ethyl acetate:cyclohexane (4:1).
1. J. Xie, et al., Int. J. Pept. Protein Res., 1989, 34, 246

3) (trans)-1-deoxy-1-[6-[(2,2-diphenylethyl)amino]-2-[(4-hydroxycyclohexyl)amino]-9H-purin-9-yl]-N-ethyl-2,3-O-methylethylidene)-β-D-ribofuranuronamide, using trans-4-aminocyclohexanol (prepared by basification of the hydrochloride salt) as the nucleophile as in entry 3 in Table 1 below. The product was purified on silica eluting with ethyl acetate:methanol 25:1. MH$^+$=642.

4) (cis)-1-deoxy-1-[6-[(2,2-diphenylethyl)amino-]2-[(4-hydroxycyclohexyl)amino]-9H-purin-9-yl]-N-ethyl-2,3-O-

(1-methylethylidene)-β-D-ribofuranuronamide, using cis-4-aminocyclohexanol[1] (prepared by basification of the hydrochloride salt) as the nucleophile as in entry 4 in Table 1 below. The product was purified on silica eluting with ethyl acetate. MH$^+$=642.

1. A. G. Renwick and R. T. Williams, *Biochem. J.,* 1972, 129, 857

5) 1-deoxy-N-ethyl-1-[2-[(3-hydroxypropyl)amino]-6-[(2,2-diphenylethyl)-9H-purin-9-yl]-2,3-O-(1-methylethylidene)-β-D-ribofuranuronamide, using 3-aminopropanol as the nucleophile as in entry 5 in Table 1 below. The product was purified on silica eluting with dichloromethane:methanol (19:1). MH$^+$=642.

6) 1-[2-[(4-aminophenyl)amino]-6-[(2,2-diphenylethyl)amino]]-9H-purin-9-yl]-1-deoxy-N-ethyl-2,3-O-(1-methylethylidene)-β-D-ribofuranuronamide, using 1,4-phenylenediamine as the nucleophile as in entry 6 in Table 1 below. The product was purified (twice) on flash silica eluting with ethyl acetate:ethanol (24:1) and then with dichloromethane:methanol (24:1) to give a still impure product. nmr(δ,CDCl$_3$) includes 6.60(d,2H), 6.70(br.s,2H).

7) 1-deoxy-1-[2-[[4-(dimethylamino)phenyl]amino]-6-[(2,2-diphenylethyl)amino]]-9-H-purin-9-yl]-N-ethyl-2,3-O-(1-methylethylidene)-β-D-ribofuranuronamide, using 4-amino-N,N-dimethylaniline as the nucleophile as in entry 7 in Table 1 below. The product was purified on flash silica eluting with dichloromethane:methanol (24:1), nmr(δ, CDCl$_3$) includes 2.80(s), 2.90(s), 6.60 to 6.70(m).

8) (1α,2β,5β)-1-deoxy-1-[2-[[2,5-dihydroxycyclopentyl]amino]-6-[(2,2-diphenylethyl)amino]]-9H-purin-9-yl]-N-ethyl-2,3-O-(1-methylethylidene)-β-D-ribofuranuronamide, using [(1α,2β,3α)-(±)]-2-amino-1,3-cyclopentanediol (Preparation 33) as the nucleophile as in entry 8 in Table 1 below. The product was purified on flash silica eluting with dichloromethane:methanol (9:1), nmr(δ,DMSO-d6) includes 1.60(br.s), 1.85(br.s), 3.8 to 4.2(2 m).

9) (1R-trans)-1-[2-[(2-aminocyclohexyl)amino]-6-[(2,2-diphenylethyl)amino]]-9H-purin-9-yl]-1-deoxy-N-ethyl-2,3-O-(1-methylethylidene)-β-D-ribofuranuronamide, using (1R-trans)-1,2-diaminocyclohexane as the nucleophile as in entry 9 in Table 1 below. The product was purified on flash silica eluting with dichloromethane:methanol (9:1). MH$^+$=641.3.

10) (1S-trans)-1-[2-[(2-aminocyclohexyl)amino]-6-[(2,2-diphenylethyl)amino]]-9H-purin-9-yl]-1-deoxy-N-ethyl-2,3-O-(1-methylethylidene)-β-D-ribofuranuronamide, using (1S-trans)-1,2-diaminocyclohexane as the nucleophile as in entry 10 in Table 1 below. The product was purified on flash silica eluting with dichloromethane:methanol(9:1). MH$^+$=641.

11) [(trans-(±)]-1-deoxy-1-[6-[(2,2-diphenylethyl)amino]-2-[4-hydroxy-1-[(1,1-dimethylethoxy)carbonyl]pyrrolidin-3-yl]amino]-9H-purin-9-yl]-N-ethyl-2,3-O-(1-methylethylidene)-β-D-ribofuranuronamide, using [trans-(±)]-3-amino-4-hydroxy-1-pyrrolidinecarboxylic acid 1,1-dimethylethyl ester as the nucleophile as in entry 11 in Table 1 below. The product was purified on flash silica eluting with dichloromethane:ethanol:0.88 ammonia (100:8:1). nmr(δ, DMSO-d6) includes 0.55(t,3H), 1.35(s,3H), 1.42(s,9H), 1.5(s,3H), 2.75(m,2H), 3.2(m,1H), 3.4–3.7(m,3H), 3.9–4.3(4H) 4.45(s,1H), 4.6(m,1H), 5.1–5.6(m,4H), 6.15(m, 1H), 7.1–7.4(m,12H)7.8(bs,1H).

12) (±)-1-deoxy-1-[(2,2-diphenylethyl)amino]-2-[(N-ethylpiperidin-3-yl)amino]-9H-purin-9-yl]-N-ethyl-2,3-O-(1-methylethylidene)-β-D-ribofuranuronamide, using (±)-1-ethyl-3-piperidinamine as the nucleophile as in entry 12 in Table 1 below. The product was purified on flash silica eluting with dichloromethane:ethanol:0.88 ammonia (100:8:1). nmr(δ,CDCl$_3$) includes 0.75(m,3H), 1.05(m,3H), 2.2–2.6(m,6H), 2.75–3.2(m,3H), 4.0–4.25(m,1H), 4.2(m,2H), 4.35(m,1H), 4.63(s,1H), 5.5(m,3H), 5.95(m,1H), 7.15–7.4(m,10H), 7.4(s,1H).

13) 1-deoxy-1-[6-[(2,2-diphenylethyl)amino]-2-[[2-(1-piperidinyl)ethyl]amino]9H-purin-9-yl]-N-ethyl-2,3-O-(1-methylethylidene)-β-D-ribofuranuronamide, using 1-(2-aminoethyl)piperidine as the nucleophile as in entry 13 in Table 1 below. The product was purified on flash silica eluting with dichlommethane:ethanol:0.88 ammonia (100:8:1). nmr(δ,CDCl$_3$) includes 0.7(t,3H), 1.4(s,3H), 1.6(s,3H) 1.6–1.9(m,2H), 2.8–3.1(m,2H), 3.12(t,2H), 3.8(m, 2H), 4.22(m,2H), 4.85(t,1H), 4.65(s,1H), 5.38(m,1H), 5.0(m,1H), 5.1(m,1H), 5.97(s,1H), 7.1–7.35(m,12H), 7.4(s, 1H), 7.6(dt,1H), 8.58(d,1H).

14) 1-deoxy-1-[6-[(2,2-diphenylethyl)amino]-2-[[2-(4-morpholinyl)ethyl]amino]-9H-purin-9-yl]-N-ethyl-2,3-O-(1-methylethylidene)-β-D-ribofuranuronamide, using 4-(2-aminoethyl)morpholine as the nucleophile as in entry 14 in Table 1 below. The product was purified on flash silica eluting with 0–2% ethanol in ethyl acetate. nmr(δ,CDCl$_3$) includes 0.7(t3H), 1.4(s,3H), 1.6(s,3H), 2.5(m,4H), 2.6(t, 2H), 2.8–3.05(m,2H), 3.4–3.55(m,2H), 3.73(m,4H), 4.15–4.25(m,2H), 4.33(t,1H), 4.63(bs,1H), 5.27(m,1H), 5.48(m,1H), 5.6(m,1H), 5.98(s,1H), 7.15–7.35(m,10H), 7.4(s,1H).

15) 1-deoxy-1-[6-[(2,2-diphenylethyl)amino]-2-[[2-(2-pyridinyl)ethyl]amino]-9H-purin-9-yl]-N-ethyl-2,3-O-(1-methylethylidene)-β-D-ribofuranuronamide, using 2-(2-aminoethyl)pyridine as the nucleophile as in entry 15 in Table 1 below. The product was purified on flash silica eluting with ethyl acetate. nmr(δ,CDCl$_3$) includes 0.68(t, 3H), 1.37(s,3H), 1.6(s,3H), 1.6–1.9(m,2H), 2.75–3.1(m,2H), 3.13(t,2H), 3.7–3.95(m,2H), 4.0–4.4(m,2H), 4.38(t,1H), 4.65(s,1H), 5.28(m,1H), 5.5(m,2H), 5.6(m,1H), 5.98(s,1H), 6.12(m,1H), 7.1–7.4(m,12H), 7.4(s,1H), 7.6(dt,1H), 8.57(d, 1H).

16) 1-deoxy-1-[6-[(2,2-diphenylethyl)amino]-2-[[2-(pyrrolidin-1-yl)ethyl]amino]-9H-purin-9-yl]-N-ethyl-2,3-O-(1-methylethylidene)-β-D-ribofuranuronamide, using 1-(2-aminoethyl)pyrrolidine as the nucleophile as in entry 16 in Table 1 below. The product was purified on flash silica eluting with dichloromethane:ethanol:0.88 ammonia (100:8:1). nmr(δ,CDCl$_3$) includes 0.63(t,3H), 1.4(s,3H), 1.6(s,3H), 2.0(m,4H), 2.7–3.0(m,2H), 2.9–3.5(m,4H), 3.6–3.9(m,2H), 4.1–4.3(m,2H), 4.32(t,1H), 4.63(s,1H), 5.4–5.65(m,4H), 5.8–6.1(m,1H), 6.05(s,1H), 7.15–7.4(m, 10H), 7.45(s,1H).

17) 1-deoxy-1-[6-[(2,2-diphenylethyl)amino]-2-[[2-(pyridinyl)methyl]amino]-9H-purin-9-yl]-N-ethyl-2,3-O-(1-methylethylidene)-β-D-ribofuranuronamide, using 2-(aminomethyl)pyridine as the nucleophile as in entry 17 in Table 1 below. The product was purified on flash silica eluting with ethyl acetate. nmr(δ,DMSO-d6) includes 0.52(t,3H), 1.12(bs,3H), 1.45(s,3H), 2.6–2.9(m,2H), 3.8–4.1(m,2H), 4.3–4.6(m,3H), 4.42(s,1H), 4.75–4.9(m,1H), 5.12(m,1H), 5.88(m,1H), 6.15(s,1H), 7.0–7.5(m,12H), 7.6–7.9(m,3H), 8.5(d,1H).

18) 1-deoxy-1-[6-[(2,2-diphenylethyl)amino]-2-[[2-(4-pyridinyl)methyl]amino]-9H-purin-9-yl]-N-ethyl-2,3-O-(1-methylethylidene)-β-D-ribofuranuronamide, using 4-aminoethyl)pyridine as the nucleophile as in entry 18 in Table 1 below. The product was purified on flash silica eluting with ethyl acetate. nmr(δ,CDCl$_3$) includes 0.65(t,3H), 1.35(s, 3H), 1.52(s,3H), 1.8–2.1(m,2H), 2.75–3.05(m,2H), 4.0–4.25(m,2H), 4.38(t,1H), 4.35–4.5(dd,1H), 4.6(s,1H), 4.75–4.95(dd,1H), 5.17(d,1H), 5.3–5.5(m,2H), 5.55–5.7(m, 1H), 5.92(m,1H), 5.94(s,1H), 7.15–7.35(m,12H), 7.4(s,1H), 8.5(m,2H).

19) 1-deoxy-1-[6-[(2,2-diphenylethyl)amino]-2-[[(1H-imidazol-2yl)methyl]amino]-9H-purin-9-yl]-N-ethyl-2,3-O-(1-methylethylidene)-β-D-ribofuranuronamide, using 2-aminomethyl)imidazole[1] (prepared by basification of the hydrochloride salt) as the nucleophile as in entry 19 in Table 1 below. The product was purified on flash silica eluting with dichloromethane:ethanol:0.880 ammonia (200:8:2) to (150:8:1.5). nmr(δ,CDCl$_3$) includes 0.54(t,3H), 1.4(s,3H), 1.59(s,3H), 2.55–2.95(m,2H), 4.05–4.2(m,2H), 4.25–4.34(m,1H), 4.4–4.5(m,1H), 4.9–5.1(m,1H), 4.7(s, 1H), 5.61(d,1H), 5.78(dd,1H), 6.03(s,1H), 7.02(s,2H), 7.15–7.35(m, 10H), 7.45(s,1H).

1. L. A. M. Bastiaansen and E. F. Godefroi, *J. Org. Chem.*, 1978, 43(8), 1603

20) 4-[2-[[6-[(2,2-diphenylethyl)amino]-9-[N-ethyl-2,3-O-(1-methylethylidene)-β-D-ribofuranuronamidosyl]-9-H-purin-2-yl]-amino]ethyl]benzenepropanoic acid 1,1-dimethylethyl ester, using 3-[4-(2-aminoethyl)phenyl]propionic acid 1,1-dimethylethyl ester[1] as the nucleophile as in entry 20 in Table 1 below. The product was purified on flash silica eluting with 20–40% ethyl acetate in cyclohexane. nmr(δ, CDCl$_3$) includes 0.67(t,3H), 1.38(s,3H), 1.43(s,9H), 1.6(s, 3H), 2.52(t,2H), 2.75–3.05(m,6H), 3.5–3.8(m,2H), 4.1–4.3(m,2H), 4.35(t,1H), 4.63(s,1H), 4.9(m,1H), 5.48(m, 2H), 5.6(d,1H), 5.97(s,1H), 7.12(m,4H), 7.15–7.35(m,10H), 7.4(s,1H).

1. A. J. Hutchison et al., *J. Med. Chem* 1990, 33, 1919

21) (1S)-1-deoxy-1-[6-[(2,2-diphenylethyl)amino]-2-[[1-(hydroxymethyl)-2-(3-pyridinyl)ethyl]amino]-9H-purin-9-yl]-N-ethyl-2,3-O-(1-methylethylidene)-β-D-ribofuranuronamide, using (S)-β-amino-3-pyridinepropanol (prepared by basification of the dihydrochloride salt) as the nucleophile as in entry 21 in Table 1 below. The product was purified on flash silica eluting with dichloromethane:ethanol:0.88 ammonia (200:8:2). MH$^+$=679.

22) (1S)-1-deoxy-1-[6-[(2,2-diphenylethyl)amino]-2-[[1-(hydroxymethyl)-2-(methyl)propyl]amino]-9H-purin-9-yl]-N-ethyl-2,3-O-(1-methylethylidene)-β-D-ribofuranuronamide using (S)-(+)-2-amino-3-methyl-1-butanol as the nucleophile as in entry 22 in Table 1 below. The product was purified on flash silica eluting with 50% ethyl acetate in cyclohexane to neat ethyl acetate. MH$^+$=630.

23) [cis-(±)]-1-deoxy-1-[6-[(2,2-diphenylethyl)amino]-2-[(3-hydroxycyclopentyl)amino]-9H-purin-9-yl]-N-ethyl-2,3-O-(1-methylethylidene)-β-D-ribofuranuronamide using [cis-(±)]-3-aminocyclopentanol[1] as the nucleophile as in entry 23 in Table 1 below. The product was purified by column chromatography on flash silica eluting with dichloromethane:ethanol:0.880 ammonia (100:8:1). nmr(δ, CDCl$_3$) includes 0.68 and 0.7(t,3H), 1.38(s,3H), 1.6(s,3H), 1.65–1.85(m,4H), 1.8–2.0(m,2H), 1.9–2.3(m,2H), 2.7–2.95 and 2.9–3.1(m,2H), 4.1–4.35(m,2H), 4.3–4.5(m,3H), 4.6(m, 1H), 5.25 and 5.37(d,1H), 5.45–5.6(m,2H), 5.97(s,1H), 7.15–7.35(m,10H), 7.4(s,1H).

1. R. A. B. Bannard, et al., *Canad. J. Chem.*, 1971, 49, 2064

24) (1S)-1-deoxy-1-[2-[1-[[[(1,1-dimethylethoxy)carbonyl]amino]methyl]-2-phenylethyl]amino]-6-[(2,2-diphenylethyl)amino]-9H-purin-9-yl]-N-ethyl-2,3-O-(1-methylethylidene)-β-D-ribofuranuronamide using (S)-(2-amino-3-phenylpropyl)carbamic acid 1,1-dimethylethyl ester (Preparation 53) as the nucleophile as in entry 24 in Table 1 below. The product was purified on flash silica eluting with 40–45% ethyl acetate in toluene. MH$^+$=777.

25) 1-deoxy-1-[2-[[2-(N,N-dimethylamino)ethyl]amino]-6-[(2,2-diphenylethyl)amino]-9H-purin-9-yl]-N-ethyl-2,3-O-(1-methylethylidene)-β-D-ribofuranuronamide using 2-(N,N-dimethylamino)ethylamine as the nucleophile as in entry 25 in Table 1 below. The product was purified on flash silica eluting with dichloromethane:ethanol:0.88 ammonia (100:8:1). MH$^+$=615.

26) 1-deoxy-1-[2-[[3-(N,N-dimethylamino)propyl]amino]-6-[(2,2-diphenylethyl)amino]-9H-purin-9-yl]-N-ethyl-2,3-O-(1-methylethylidene)-β-D-ribofuranuronamide using 3-(N,N-dimethylamino)propylamine as the nucleophile as in entry 26 in Table 1 below. The product was purified on flash silica eluting with dichlormethane:ethanol:0.880 ammonia (100:8:1). MH$^+$=629.

27) (+1-)-1-deoxy-1-[6-[(2,2-diphenylethyl)amino]-2-[(5-oxo-3-pyrrolidinyl)amino]-9H-purin-9-yl]-N-ethyl-2,3-O-(1-methylethylidene)-β-D-ribofuranuronamide using (±)-4-amino-1H-pyrrolidin-2-one (prepared by basification of the hydrochloride salt) (Preparation 26) as the nucleophile as in entry 27 in Table 1 below. The product was purified on flash silica eluting with dichloromethane:ethanol:0.880 ammonia (200:8:1) to (100:8:1). nmr(δ,CDCl$_3$) includes 0.6–0.7(m,3H), 1.4(s,6H), 2.8–3.0(m,2H), 3.3–3.4 and 3.75–3.9(m,22H), 4.0–4.35(m,3H), 4.65(s,1H), 4.7–4.8(m, 1H), 5.4–5.7(m,2H), 6.01(d,1H), 7.2–7.4(m,10H), 7.45–7.5(bs,1H).

28) 1-deoxy-1-[6-[(2,2-diphenylethyl)amino]-2-[[1-hydroxymethyl)cyclopropyl]amino]-9H-purin-9-yl]-N-ethyl-2,3-O-(1-methylethylidene)-β-D-ribofuranuronamide using 1-amino-cyclopropanemethanol (Preparation 23) as the nucleophile as in entry 28 in Table 1 below. The product was purified on flash silica eluting with 50% ethyl acetate in cyclohexane to neat ethyl acetate. MH$^+$=614.

29) 1-deoxy-1-[6-[(2,2-diphenylethyl)amino]-2-[[2-(1-piperazinyl)ethyl]amino]-9H-purin-9-yl]-N-ethyl-2,3-O-(1-methylethylidene)-β-D-ribofuranuronamide using 1-(2-aminoethyl)piperazine as the nucleophile as in entry 29 in Table 1 below. The product was purified on flash silica eluting with dichloromethane:ethanol:0.88 ammonia (100:8:1). nmr(δ, CDCl$_3$) includes 0.7(t,3H), 1.35(s,3H), 1.6(s,3H), 2.4–2.7(m,6H), 2.87(t,2H), 2.8–3.1(m,2H), 3.25–3.6(m, 2H), 3.65–3.9(m,4H), 4.1–4.3(m,2H), 4.35(m,1H), 4.62(s, 1H), 5.4–5.7(m,1H), 5.55(s,2H), 5.85–6.05(m,1H), 6.0(s, 1H), 7.15–7.35(m,10H), 7.4(s,1H).

30) [trans-(±)]-1-deoxy-1-[6-[(2,2-diphenylethyl)amino]-2-[(2-hydroxycyclohexyl)amino]-9H-purin-9-yl]-N-ethyl-2,3-O-(1-methylethylidene)-β-D-ribofuranuronamide, using [trans-(±)]2-aminocyclohexanol (prepared by basification of the hydrochloride salt) as the nucleophile as in entry 30 in Table 1 below. The product was purified on silica eluting with ethyl acetate:cyclohexane (2:1). MH$^+$=642.

31) (1α,3β,4β)-1-deoxy-1-[2-[(3,4-dihydroxycyclopentyl)amino]-6-[(2,2-diphenylethyl)amino]]-9H-purin-9-yl]-N-ethyl-2,3-O-(1-methylethylidene)-β-D-ribofuranuronamide, using (1α,2α,4β)4-amino-1,2-cyclopentanediol (prepared by basification of the hydrochloride salt) as the nucleophile as in entry 31 in Table 1 below. The product was purified on silica eluting with ethyl acetate:methanol (24:1). nmr(δ, DMSO-d6) includes 1.60(br.s,2H), 1.82(br.s,2H), 4.0(br.s).

32) 1-[2-[(2-cyclohexylethyl)amino]-6-[(2,2-diphenylethyl)-9H-purin-9-yl]-1-deoxy-N-ethyl-2,3-O-(1-methylethylidene)-β-D-ribofuranuronamide, using 2-cyclohexylethylamine as the nucleophile as in entry 32 in Table 1 below. The product was purified on silica eluting with ethyl acetate:cyclohexane (1:1). nmr(δ,CDCl$_3$) includes 0.7(t, 3H), 0.8–1.1(m,2H), 1.1–1.5(m,4H), 1.4(s,3H), 1.45–1.55(m,1H), 1.6(s,3H), 1.5–1.8(m,6H), 2.8–3.1(m, 2H), 3.2–3.45(m,1H), 3.35–3.6(m,1H), 4.1–4.3(m,2H), 4.35(t,1H), 4.63(s,1H), 4.8(m,1H), 5.5(m,1H), 5.6(d,1H), 5.97(s,1H), 6.05(m,1H), 7.15–7.35(m,10H), 7.4(s,1H).

33) (1R)-1-deoxy-1[-6-[(2,2-diphenylethyl)amino]-2-[[1-(hydroxymethyl)-2-phenylethyl]amino]-9H-purin-9-yl]-N- ethyl-2,3-O-(1-methylethylidene)-β-D-ribofuranuronamide, using (R)-2-amino-3-phenyl-1-propanol as the nucleophile as in entry 33 in Table 1 below. The product was purified on silica eluting with 50% ethyl acetate in cyclohexane to neat ethyl acetate. MH$^+$=678.

34) (1S)-1-deoxy-1-[6-[(2,2-diphenylethyl)amino]-2-[[1-(methoxymethyl)-2-phenylethyl]amino]-9-H-purin-9-yl]-N-ethyl-2,3-O-(1methylethylidene)-β-D-ribofuranuronamide, using (S)-2-amino-1-methoxy-3-phenylpropane (prepared by basification of the hydrochloride salt) as the nucleophile as in entry 34 in Table 1 below. The product was purified on silica eluting with 50–70% ethyl acetate in cyclohexane. MH$^+$=692.

35) 1-deoxy-1-[6-[(2,2-diphenylethyl)amino]-2-[[2-(2-methyl-1H-imidazol-1-yl)ethyl]amino]-9H-purin-9-yl]-N-ethyl-2,3-O-(1-methylethylidene)β-D-ribofuranuronamide, using 2-(2-methyl-1H-imidazol-1-yl)ethylamine (prepared by basification of the hydrochloride salt[1]) as the nucleophile as in entry 35 in Table 1 below. The product was purified on silica with gradient elution of 1–8% methanol in dichloromethane and addition of ether to the resulting oil gave a solid. nmr(δ,CDCl$_3$) includes 0.65(t,3H), 1.4(s,3H), 1.6(s, 3H), 2.35(s,3H), 2.7–3.05(m,2H), 3.6–3.8(m,2H), 4.05–4.25(m,3H), 4.3(t,1H), 4.67(s,1H), 4.85–5.0(m,1H), 5.43(d,1H), 5.45–5.15(m,1H), 5.63(dd,1H), 5.9–6.0(m,1H), 6.03(s,1H), 6.86(bs,1H), 7.15–7.4(m,10H), 7.45(s,1H).

1. Shikoku Kaken Kogyo K. K., Japanese Patent 62,198,668.

36) [(1S)-trans]-1-deoxy-1-[6-[(2,2-diphenylethyl)amino]-2-[(3-N,N-dimethylamino)cyclopentylamino]-9H-purin-9-yl]-N-ethyl-2,3-O-(1-methylethylidene)-β-D-ribofuranuronamide, using (S)-3-(N,N-dimethylaminocyclopentyl)amine (prepared by basification of the hydrochloride salt) as the nucleophile as in entry 36 in Table 1 below. The product was purified on silica eluting with dichloromethane:ethanol:0.88 ammonia (100:8:1) to (50:8:1) and preparative HPLC (30–90% acetonitrile). MH$^+$=655.

37) 1-[2-[[(6-Amino-2-pyridinyl)methyl]amino]-6-[(2,2-diphenylethyl)amino]-9H-purin-9-yl]-1-deoxy-N-ethyl-2,3-O-(1-methylethylidene)-β-D-ribofuranuronamide using 6-amino-2-pyridinemethanamine as the nucleophile as in entry 37 in Table 1 below. The product was purified on silica eluted with ethyl acetate and the addition of ether to the resulting oil gave a solid. nmr (δ, CDCl$_3$) includes 0.7(t,3H), 1.35(s,3H), 1.58(s,3H), 2.85–3.15(m,2H), 4.1–4.3(m,2H), 4.3–4.4(t,1H), 4.45(bs,2H), 4.45–4.46(m,2H), 4.65(d,1H), 5.4(d,1H), 5.56(d,1H) 5.95(s,1H), 6.36(d,1H), 6.7(d,1H), 7.15–7.35(m,10H), 7.35(t,1H), 7.42 (s,1H).

TABLE 1

| Entry | 2-chloropurine g. | nucleophile g. | DMSO ml | temp. °C. | reaction time |
|---|---|---|---|---|---|
| 1 | 0.239 | 0.43 | nil | 140 | 18 h |
| 2 | 0.061 | 0.10 | 0.40 | 140 | 48 h |
| 3 | 0.371 | 1.0(HCl salt) | nil | 140 | 8 h |
| 4 | 0.180 | 0.48(HCl salt) | 0.5 | 140 | 7 h |
| 5 | 0.30 | 0.398 | 1.5 | 140 | 1.5 h |
| 6 | 0.2275 | 0.510 | nil | 140 | 48 h |
| 7 | 0.200 | 0.440 | 0.8 | 140 | 24 h |
| 8 | 0.185 | 0.185 | nil | 140 | 48 h |
| 9 | 0.105 | 0.226 | nil | 140 | 3 h |
| 10 | 0.104 | 0.213 | nil | 140 | 4.5 h |
| 11 | 0.32 | 0.4 | 1.5 | 135 | 48 h |
| 12 | 0.26 | 0.577 | nil | 120 | 18 h |
| 13 | 0.261 | 0.577 | nil | 120 | 18 h |
| 14 | 0.286 | 1.03 | nil | 120 | 4.5 h |
| 15 | 0.257 | 0.42 | 2.0 | 130 | 18 h |
| 16 | 0.284 | 0.82 | nil | 120 | 4.5 h |
| 17 | 0.2 | 0.2 | nil | 130 | 18 h |
| 18 | 0.202 | 0.192 | nil | 120 | 26 h |
| 19 | 0.321 | 0.58(HCl salt) | nil | 130 | 48 h |
| 20 | 0.252 | 0.623 | 2.0 | 130 | 18 h |
| 21 | 0.25 | 0.3(HCl salt) | 1.0 | 140 | 312 h |
| 22 | 0.322 | 0.354 | 1.0 | 120 | 77 h |
| 23 | 0.250 | 0.13 | nil | 135 | 72 h |
| 24 | 0.3 | 0.8 | 1.0 | 125 | 156 h |
| 25 | 0.304 | 0.286 | 1.0 | 130 | 4 h |
| 26 | 0.304 | 0.331 | 1.0 | 130 | 4 h |
| 27 | 0.3 | 0.36(HCl salt) | 1.0 | 140 | 192 h |
| 28 | 0.3 | 0.232 | 1.0 | 140 | 207 h |
| 29 | 0.27 | 1.0 | 2.0 | 130 | 18 h |
| 30 | 0.249 | 1.31(HCl salt) | nil | 140 | 44 h |
| 31 | 0.083 | 0.113 | nil | 120 | 18 h |
| 32 | 0.252 | 0.340 | 2.0 | 130 | 48 h |
| 33 | 0.250 | 0.403 | nil | 130 | 73 h |
| 34 | 0.325 | 0.75(HCl salt) | 1.0 | 130 | 96 h |
| 35 | 0.320 | 0.88(HCl salt) | 2.5 | 130 | 41 h |
| 36 | 1.306 | 0.47(HCl saIt) | 4.0 | 130 | 47 h |
| 37 | 0.260 | 0.32 | 2.0 | 110 | 60 h |

Example 21

(1S)-1-Deoxy-1-[6-[(2,2-diphenylethyl)amino]-2-[[1-(hydroxymethyl)-2-phenylethyl]amino]-9H-purin-9-yl]-N-ethyl-β-D-ribofuranuronamide A solution of (1S)-1-deoxy-1-[6-[(2,2-diphenylethyl)amino]-2-[[1-(hydroxymethyl)-2-phenylethyl]amino]-9H-purin-9-yl]-N-ethyl-2,3-O-(1-methylethylidene)-β-D-ribofuranuronamide (0.104 g, 0.16 mmol) in trifluoracetic acid (4.7 ml) and water (0.3 ml) was stirred for 3.5 h then evaporated to dryness. The residue was dissolved in ethanol (10 ml) and the solution was stirred with sodium carbonate (1 g) for 0.7 h. The mixture was filtered and the filtrate was evaporated to leave a froth which was dissolved in ethyl acetate (50 ml) and washed with water (40 ml), dried (MgSO$_4$) and evaporated to give the title compound (0.082 g) as a solid MH$^+$=638, nmr(δ,DMSO-d6) includes 0.98(t, 3H), 2.88(m,2H), 3.05–3.25(m,2H), 3.4–3.5(m,2H), 4.23(s, 1H), 5.48(d,1H), 5.6(d,1H), 5.8(d,1H), 7.1–7.4(m,15H).

Similarly prepared were:

1) [cis-(±)]-1-deoxy-1-[6-[(2,2-diphenylethyl)amino]-2-[(2,-hydroxycyclopentyl)amino]-9H-purin-9-yl]-N-ethyl-β-D-ribofuranuronamide, from the product as in entry 1 in Example 20 and in Table 1 above, under conditions as in entry 1 in Table 2 below. The product was purified on silica eluting with ethyl acetate:methanol (19:1). The product had MH$^+$=588, nmr(δ,DMSO-d6) 1.05(t,3H), 1.35 to 1.90(m, 6H), 3.15(m,2H), 4.05(m,4H), 4.25(s,1H), 4.65(m,2H), 4.85 (d,1H), 5.50(d,1H), 5.65(t,2H), 5.80(d,1H), 7.10 to 7.40(m, 11H), 7.50(m,1H), 7.90(s,1H), 8.55(m,1H).

2) [trans-(±)]-2-[[6-[(2,2-diphenylethyl)amino]-9-(N-ethyl-β-D-ribofuranuronamidosyl)-9H-purin-2-yl]-amino] cyclopentanecarboxylic acid, from the product as in entry 2 in Example 20 and in Table 1 above, under conditions as in entry 2 in Table 2 below. The product was purified by preparative HPLC (30 to 70% acetonitrile). The product had MH$^+$=616, nmr(δ,DMSO-d6) 1.00(t,3H), 1.70(m,4H), 2.05 (m,2H), 2.80(m,1H), 3.15(m,2H), 4.10(m,3H), 4.30(s,1H), 4.60(m,4H), 5.85(d,1H), 7.15 to 7.40(m,10H), 8.25(m,2H).

3) (trans)-1-deoxy-1-[6-[(2,2-diphenylethyl)amino]-2-[(4-hydroxycyclohexyl)amino]-9H-purin-9-yl]-N-ethyl-β-D-ribofuranuronamide, from the product as in entry 3 in Example 20 and in Table 1 above, under conditions as in entry 3 in Table 2 below. The product was purified by preparative HPLC (30 to 70% acetonitrile). The product had MH$^+$=602. Analysis found C, 52.7, H, 5.15, N, 11.8, F, 11.8%; $C_{32}H_{39}N_7O_5.1.75CF_3CO_2H.0.4H_2O$ requires C, 52.7, H, 5.2, N, 12.1, F, 12.3%.

4) (cis)-1-deoxy-1-[6-[(2,2-diphenylethyl)amino]-2-[(4-hydroxycyclohexyl)amino]-9H-purin-9-yl]-N-ethyl-β-D-ribofuranuronamide, from the product as in entry 4 in Example 20 and in Table 1 above, under conditions as in entry 4 in Table 2 below. The product was purified by preparative HPLC (30 to 70% acetonitrile). The product had MH$^+$=602. Analysis found C, 53.35, H, 5.65, N, 11.8, F, 9.9%; $C_{32}H_{39}N_7O_5.1.4CF_3CO_2H.0.9H_2O$ requires C, 53.75, H, 5.5, N, 11.6, F, 10.25%

5) 1-deoxy-N-ethyl-1-[2-[(3-hydroxypropyl)amino]-6-[(2,2-diphenylethyl)amino]-9-H-purin-9-yl]-β-D-ribofuranuronamide, from the product as in entry 5 in Example 20 and in Table 1 above, under conditions as in entry 5 in Table 2 below. The product was purified by preparative HPLC (30 to 70% acetonitrile). The product had MH$^+$=562. Found C, 52.75, H, 5.1, N, 13.65, F, 9.9%. $C_{29}H_{35}N_7O_5.1.25CF_3CO_2H.0.6H_2O$ requires C, 52.95, H, 5.3, N, 10.0%.

6) 1-[2-[(4-aminophenyl)amino]-6-[(2,2-diphenylethyl)amino]]-9H-purin-9-yl]-1-deoxy-N-ethyl-β-D-ribofuranuronamide, from the product as in entry 6 in Example 20 and in Table 1 above, under conditions as in entry 6 in Table 2 below. The product was purified on flash silica (twice) eluting with dichloromethane:methanol (9:1). The product had MH$^+$=594, nmr(δ,DMSO-d6) includes 6.50 (d,2H), 7.28 to 7.48(m,12H)

7) 1-deoxy-1-[2-[[4-(dimethylamino)phenyl]amino]-6-[(2,2-diphenylethyl)amino]]-9H-purin-9-yl]-N-ethyl-β-D-ribofuranuronamide, from the product as in entry 7 in Example 20 and in Table 1 above, under conditions as in entry 7 in Table 2 below. The product was purified twice by preparative HPLC (30 to 70% acetonitrile). The product had MH$^+$=623, nmr(δ,DMSO-D-6) includes 2.95 to 3.2(br.s, 6H), 7.15 to 7.25(m,2H), 7.75 to 7.9(m,2H).

8) (1α,2β,5β)-1-deoxy-1-[2-[[2,5-dihydroxycyclopentyl]amino]-6-[(2,2-diphenylmethyl)amino]]-9H-purin-9-yl]-N-ethyl-β-D-ribofuranuronamide, from the product as in entry 8 in Example 20 and in Table 1 above, under conditions as in entry 8 in Table 2 below. The product was purified on flash silica eluting with dichloromethane:ethanol:0.880 ammonia (30:8:1) and then on flash silica eluting with ethyl acetate: methanol (19:1). The product had MH$^+$=604, nmr(δ,DMSO-d6) includes 1.67(br.s,2H), 1.90(br.s,2H), 4.0(br.s,2H).

9) (1R-trans)-1-[2-[[2-aminocyclohexyl]amino]-6-[(2,2-diphenylethyl)amino]]-9H-purin-9-yl]-1-deoxy-N-ethyl-β-D-ribofuranuronamide, from the product as in entry 9 in Example 20 and in Table 1 above, under conditions as in entry 9 in Table 2 below. The product was purified on flash silica eluting with dichloromethane:ethanol:0.880 ammonia (30:8:1). The product had MH$^+$=601, nmr(δ,DMSO-d6) includes 1.23(br.s,6H), 1.68(br.s,2H), 2.92(br.s,1H).

10) (1S-trans)-1-[2-[[2-aminocyclohexyl]-amino]-6-[(2,2-diphenylethyl)amino]]-9H-purin-9-yl]-1-deoxy-N-ethyl-β-D-ribofuranuronamide, from the product as in entry 10 in Example 20 and in Table 1 above, under conditions as in entry 10 in Table 2 below. The product was purified on flash silica eluting with dichloromethane:ethanol:0.880 ammonia (30:8:1). The product had MH$^+$=601, nmr(δ,DMSO-d6) includes 1.24(br.s,6H), 1.64(br.s,2H), 2.66(br.s,1H).

11) [trans-(±)]-1-deoxy-1-[6-[(2,2-diphenylethyl)amino]-2-(4-hydroxy-3-pyrrolidinyl)amino]-9H-purin-9-yl]-N-ethyl-β-D-ribofuranuronamide, from the product as in entry 11 in Example 20 and in Table 1 above, under conditions as in entry 11 in Table 2 below. The product was purified by preparative HPLC (20 to 60% acetonitrile). The product had MH$^+$=589, nmr(δ,DMSO-d6) includes 1.0(t,3H), 3.0–3.25 (m,3H), 3.25–3.6(m,3H), 4.1(m,2H), 4.15(m,1H), 4.25(s, 1H), 4.25–4.5(m,2H), 4.6(m,2H), 5.85(d,1H), 7.1–7.4(10H), 8.14(m,2H).

12) (±)-1-deoxy-1-[6-[(2,2-diphenylethyl)amino]-2-[(N-ethylpiperidin-3-yl)amino]-9H-purin-9-yl]-N-ethyl-β-D-ribofuranuronamide, from the product as in entry 12 in Example 20 and in Table 1 above, under conditions as in entry 12 in Table 2 below. The product was purified by preparative HPLC (30 to 70% acetonitrile). The product had MH$^+$=615, nmr(δ,DMSO-d6) includes 1.0(t,3H)1.2(m,3H), 1.5–2.2(m,4H), 2.4–2.9(m,2H), 3.05–3.25(m,4H), 4.15(m, 1H), 4.25(bs,1H), 4.5–4.7(m,2H), 5.87(m,1H), 7.15–7.4(m, 10H), 8.12(m,2H).

13) 1-deoxy-1-[6-[(2,2-diphenylethyl)amino]-2-[[2-(1-piperidinyl)ethyl]amino]9H-purin-9-yl]-N-ethyl-β-D-ribofuranuronamide, from the product as in entry 13 in Example 20 and in Table 1 above, under conditions as in entry 13 in Table 2 below. The product was isolated by evaporation of the reaction mixture and the addition of ether to give a solid. The product had MH$^+$=615, nmr(δ,DMSO-d6) includes 1.02(t,3H), 1.25–1.5(m,1H), 1.5–1.85(m,4H), 2.9(m,1H), 3.14(m,1H), 3.22(m,1H), 3.5(m,1H), 3.65(m, 1H), 4.07(m,2H), 4.2(m,1H), 4.28(s,1H), 4.6(m,2H), 5.85 (d,1H), 7.15–7.4(m,10H), 8.15(m,2H).

14) 1-deoxy-1-[6-[(2,2-diphenylethyl)amino]-2-[[2(4-morpholinyl)ethyl]amino]-9H-purin-9-yl]-N-ethyl-β-D-ribofuranuronamide, from the product as in entry 14 in Example 20 and in Table 1 above, under conditions as in entry 14 in Table 2 below. The product was isolated by evaporation of the reaction mixture and the addition of ether to give a solid. The product had MH$^+$=617, nmr(δ,DMSO-d6) includes 1.02(t,3H), 3.14(m,4H), 3.45(m,4H), 4.25(s, 1H), 4.55(m,2H), 5.85(d,1H), 7.15–7.4(m,10H), 8.15(bs, 2H).

15) 1-deoxy-1-[6-[(2,2-diphenylethyl)amino]-2-[[2-(2-pyridinyl)ethyl]amino]-9H-purin-9-yl]-N-ethyl-β-D-ribofuranuronamide from the product as in entry 15 in Example 20 and in Table 1 above, under conditions as in entry 15 in Table 2 below. The product was isolated by evaporation of the reaction mixture and the addition of ether to give a solid. The product had MH$^+$=609, nmr(δ,DMSO-d6) includes 1.02(t,3H), 3.05–3.25(m,2H), 3.15–3.35(m, 2H), 3.7–3.9(m,2H), 4.1(m,1H), 4.2(m,1H), 4.35(s,1H), 4.5–4.7(m,2H), 5.87(d,1H), 7.15–7.4(m,10H), 7.6–7.8(m, 2H), 8.1–8.4(m,3H), 8.72(m,1H).

16) 1-deoxy-1-[6-[(2,2-diphenylethyl)amino]-2-[[2-(pyrrolidin-1-yl)ethyl]amino]-9H-purin-9-yl]-N-ethyl-β-D-ribofuranuronamide, from the product as in entry 16 in Example 20 and in Table 1 above, under conditions as in entry 16 in Table 2 below. The product was purified by preparative HPLC (30 to 70% acetonitrile). The product had MH$^+$=601, nmr(δ,DMSO-d6) includes 1.02(t,3H); 1.7–2.1 (m,4H) 2.9–3.25(m,4H), 3.35(m,2H), 3.6(m,4H), 4.78(s, 1H), 4.55(m,3H), 5.85(d,1H), 7.1–7.4(m,10H), 8.15(bs,2H).

17) 1-deoxy-1-[6-[(2,2-diphenylethyl)amino]-2-[[2(2-pyridinyl)methyl]amino]9H-purin-9-yl]-N-ethyl-β-D-ribofuranuronamide, from the product as in entry 17 in Example 20 and in Table 1 above, under conditions as in entry 17 in Table 2 below. The product was purified on flash silica eluting with dichloromethane:ethanol:0.880 ammonia (30:8:1). The product had MH$^+$=601, nmr(δ,DMSO-d6)

includes 1.02(t,3H), 3.1–3.3(m,2H), 3.7–4.0(m,2H), 4.15 (bs,1H), 4.32(s,1H), 4.4–4.6(m,3H), 4.8(s,1H), 5.85(d,1H), 7.1–7.4(m,10H), 7.65(t,1H), 7.72(d,1H), 8.0–8.5(m,2H), 8.2 (s,1H), 8.67(d,1H).

18) 1-deoxy-1-[6-[(2,2-diphenylethyl)amino]-2-[[2-(4-pyridinyl)methyl]amino]9H-purin-9-yl]-N-ethyl-β-D-ribofuranuronamide, from the product as in entry 18 in Example 20 and in Table 1 above, under conditions as in entry 18 in Table 2 below. The product was purified by preparative HPLC (20 to 60% acetonitrile). The product had MH⁺=601, nmr(δ,DMSO-d6) includes 1.02(t,3H), 3.05–3.3 (m,2H), 3.75–4.0(m,2H), 4.14(m,1H), 4.25(s,1H), 4.45(m, 2H), 4.55(m,1H), 5.82(d,1H), 7.05–7.4(m,10H), 7.85(d,2H), 8.12(s,1H), 8.78(d,2H).

19) 1-deoxy-1-[6-[(2,2-diphenylethyl)amino]-2-[[(1H-imidazol-2-yl)methyl]amino]-9H-purin-9-yl]-N-ethyl-β-D-ribofuranuronamide, from the product as in entry 19 in Example 20 and in Table 1 above, under conditions as in entry 19 in Table 2 below. The product was purified by preparative HPLC (30 to 90% acetonitrile). The product had MH⁺=584, nmr(δ,DMSO-d6) includes 1.01(t,3H), 3.08–3.2 (m,2H), 3.8–4.3(m,4H), 4.4–4.52(m,2H), 4.72–4.82(m,1H), 5.82(d,1H), 7.15–7.4(m,10H), 7.55(bs,2H), 7.55–7.65(m, 1H), 8.1–8.2(m,2H).

20) 4-[2-[[6-[(2,2-diphenylethyl)amino]-9-[N-ethyl-β-D-ribofuranuronamidosyl]-9H-purin-2-yl]-amino]-ethyl] benzenepropanoic acid, from the product as in entry 20 in Example 20 and in Table 1 above, under conditions as in entry 20 in Table 2 below. The product was isolated by evaporation of the reaction mixture and the addition of ethyl acetate to give a solid. The product had MH⁺=680, nmr(δ, DMSO-d6) includes 1.02(t,3H), 2.7–2.95(m,4H), 3.05–3.3 (m,2H), 3.4–3.7(m,2H), 4.0–4.25(m,3H), 4.35(s,1H), 4.45–4.7(m,2H), 5.88(d,1H), 7.13(s,4H), 7.15–7.4(m,10H), 8.16(bs,1H).

21) (1S)-1-deoxy-1-[6-[(2,2-diphenylethyl)amino]-2-[[1-(hydroxymethyl)-2-(3-pyridinyl)ethyl]amino]-9H-purin-9-yl]-N-ethyl-β-D-ribofuranuronamide, from the product as in entry 21 in Example 20 and in Table 1 above, under conditions as in entry 21 in Table 2 below but using 4M-aqueous hydrogen chloride in 1,4-dioxan for the deprotection. The product was purified by preparative HPLC (20–40% acetonitrile). MH⁺=639, nmr(δ,DMSO-d6) includes 1.0(t,3H), 2.9–3.2(m,4H), 4.3(s,1H), 4.5–4.6(m, 2H), 5.82(d,1H), 7.15–7.4(m,11H), 7.65–7.75(m,1H), 8.6–8.75(m,2H).

22) (1S)-1-deoxy-1-[6-[(2,2-diphenylethyl)amino]-2-[[1-hydroxymethyl)-2-(methyl)propyl]amino]-9H-purin-9-yl]-N-ethyl-β-D-ribofuranuronamide, from the product as in entry 22 in Example 20 and in Table 1 above, under conditions as in entry 22 in Table 2 below but using 4M-aqueous hydrogen chloride in 1.4-dioxan for the deprotection. The product was purified by preparative HPLC (30–60% acetonitrile) had MH⁺=590, nmr(δ,DMSO-d6) includes 0.9–1.0(m,6H), 1.01(t,3H), 3.1–3.3(m,2H), 3.5–3.6 (m,2H), 3.9–4.2(4H), 4.5–4.7(m,2H), 4.23(s,1H), 5.49(d, 1H), 5.61(d,1H), 5.75–5.85(m,1H), 7.1–7.4(m,10H), 7.91(s, 1H).

23) [cis-(±)]-1-deoxy-1-[6-[(2,2-diphenylethyl)amino]-2-[(3-hydroxycyclopentyl)amino]-9H-purin-9-yl]-N-ethyl-β-D-ribofuranuronamide from the product as in entry 23 in Example 20 and in Table 1 above, under conditions as in entry 23 in Table 2 below. The product was purified by preparative HPLC (40–80% acetonitrile) and had MH⁺=588, nmr(δ,DMSO-d6) includes 1.02(t,3H), 1.4–1.85(m,4H), 1.9–2.3(m,2H), 3.1–3.3(m,2H), 4.0–4.15(m,1H), 4.1–4.3(m, 2H), 4.33(s,1H), 4.5–4.7(m,2H), 5.54(d,1H), 7.1–7.4(m, 10H), 8.14(bs,1H).

24) (1S)-1-[2-[[1-(aminomethyl)-2-phenylethyl]amino]-6-[(2,2-diphenylethyl)amino]-9H-purin-9-yl]-1-deoxy-N-ethyl-β-D-ribofuranuronamide from the product as in entry 24 in Example 20 and in Table 1 above, under conditions as in entry 24 in Table 2 below. The product was purified by preparative HPLC (32 to 40% acetonitrile). The product had MH⁺=637, nmr(δ,DMSO-d6) includes 1.0(t,3H), 2.7–2.8(m, 2H), 2.9–3.2(m,4H), 4.5–4.65(m,1H), 5.85–5.95(m,1H), 6.55–6.65(m,1H), 7.15–7.4(m,15H), 8.1–8.2(m,2H).

25) 1-deoxy-1-[2-[[2-(N,N-dimethylamino)ethyl]amino]-6-[(2,2-diphenylethyl)amino]-9H-purin-9-yl]-N-ethyl-β-D-ribofuranuronamide from the product as in entry 25 in Example 20 and in Table 1 above, under conditions as in entry 25 in Table 2 below. The product was purified by preparative HPLC (27 to 60% acetonitrile). The product had MH⁺=575, nmr(δ,DMSO-d6) includes 1.0(t,3H), 2.82(s, 3H), 2.83(s,3H), 3.1–3.2(m,2H), 3.2–3.35(m,2H), 3.55–3.7 (m,2H), 4.5–4.6(d,1H), 5.85(d,1H), 6.75–6.9(m,1H), 7.15–7.4(m,10H), 8.1–8.2(m,2H).

26) 1-deoxy-1-[2-[[3-(N,N-dimethylamino)propyl] amino]-6-[(2,2-diphenylethyl)amino]-9H-purin-9-yl]-N-ethyl-β-D-ribofuranuronamide from the product as in entry 26 in Example 20 and in Table 1 above, under conditions as in entry 26 in Table 2 below. The product was purified by preparative HPLC (27 to 54% acetonitrile). The product had MH⁺=589, nmr(δ,DMSO-d6) includes 1.01(t,3H), 1.85–2.0 (m,2H), 2.75(s,3H), 2.76(s,3H), 3.05–3.2(m,4H), 3.3–3.45 (m,2H), 4.5–4.6(m,1H), 5.86(d,1H), 7.15–7.4(m,10H), 8.1–8.25(m,2H).

27) (±)1-deoxy-1-[6-[(2,2-diphenylethyl)amino]-2-[(5-oxo-3-pyrrolidinyl)amino]-9H-purin-9-yl]-N-ethyl-β-D-ribofuranuronamide, from the product as in entry 27 in Example 20 and in Table 1 above, under conditions as in entry 27 in Table 2 below. The product was purified by preparative HPLC (30 to 70% acetonitrile). The product had MH⁺=587, nmr(δ,DMSO-d6) includes 1.01 (t,3H), 2.2–2.3 (m,1H), 2.76–2.8(m,1H), 3.1–3.25(m,3H), 3.58–3.68(m, 1H), 5.86(d,1H), 7.3–7.4(m, 10H), 7.66(d,1H), 8.15–8.25 (bs,1H).

28) 1-deoxy-1-[6-[(2,2-diphenylethyl)amino]-2-[[1-(hydroxymethyl)cyclopropyl]amino]-9H-purin-9-yl]-N-ethyl-β-D-ribofuranuronamide, from the product as in entry 28 in Example 20 and in Table 1 above, under conditions as in entry 28 in Table 2 below but using 4M aqueous hydrogen chloride in 1,4-dioxan for the deprotection. The product was purified by preparative HPLC (30–53% acetonitrile) and had MH⁺=574, nmr(δ,DMSO-d6) includes 0.7–0.9(m,4H), 1.01 (t,3H), 3.1–3.25(m,2H), 4.0–4.1 and 4.13–4.2(ms,3H), 4.25–4.3(bs,1H), 4.5–4.7(m,2H), 5.82(d,1H), 7.2–7.4(m, 10H), 8.12(bs,1H).

29) 1-deoxy-1-[6-[(2,2-diphenylethyl)amino]-2-[[2-(1-piperazinyl)ethyl]amino]-9H-purin-9-yl]-N-ethyl-β-D-ribofuranuronamide, from the product as in entry 29 in Example 20 and in Table 1 above, under conditions as in entry 29 in Table 2 below. The product was purified by preparative HPLC (30 to 70% acetonitrile). The product had MH⁺=616, nmr(δ,DMSO-d6) includes 1.02(t,3H), 3.0–3.25 (m,2H), 3.1–3.45(m,4H), 4.25(s,1H), 4.5–4.7(m,3H), 5.88 (d,1H), 7.15–7.4(m,10H), 8.15(s,1H).

30) [trans-(±)]-1-deoxy-1-[6-[(2,2-diphenylethyl)amino]-2-[(2-hydroxycyclohexyl)amino]-9H-purin-9-yl]-N-ethyl-β-D-ribofuranuronamide, from the product as in entry 30 in Example 20 and in Table 1 above, under conditions as in entry 30 in Table 2 below. The product was purified on flash silica eluting with dichloromethane:methanol:0.880 ammonia (90:10:1). The product had MH$^+$=602, nmr(δ,DMSO-d6) includes 1.20(br.s), 1.60(br.s), 1.92(br.s), 2.20(br.s).

31) (1α,3β,4β)-1-deoxy-1-[2-[(3,4-dihydroxycyclopentyl)amino]-6-[(2,2-diphenylethyl)amino]]-9H-purin-9-yl]-N-ethyl-β-D-ribofuranuronamide, from the product as in entry 31 in Example 20 and in Table 1 above, under conditions as in entry 31 in Table 2 below (as the sum of 2 similar experiments whose products were combined). The product was purified by preparative HPLC (30 to 70% acetonitrile). The product had MH$^+$=604, nmr(δ,DMSO-d6) includes 1.69(br.s,2H), 1.90(br.s,2H), 4.0(br.s,2H).

32) 1-[2-[(2-cyclohexylethyl)amino]-6-[(2,2-diphenylethyl)amino]-9H-purin-9-yl]-1-deoxy-N-ethyl-β-D-ribofuranuronamide, from the product as in entry 32 in Example 20 and in Table 1 above, under conditions as in entry 32 in Table 2 below. The product was purified by preparative HPLC (30 to 70% acetonitrile). The product had MH$^+$=614, nmr(δ,DMSO-d6) includes 0.8–1.0(m,2H), 1.05 (t,3H), 1.1–1.4(m,5H), 1.4–1.8(6H), 3.1–3.3(m,2H), 3.3–3.6 (m,2H), 4.35(s,1H), 4.45–4.7(m,2H), 5.87(d,1H), 7.15–7.4 (10H), 8.2(bs,1H).

33) (1R)-1-deoxy-1-[6-[(2,2-diphenylethyl)amino]-2-[[1-(hydroxymethyl)-2-phenylethyl]amino]-9H-purin-9-yl]-N-ethyl-β-D-ribofuranuronamide from the product as in entry 33 in Example 20 and in Table 1 above, under conditions as in entry 33 in Table 2 below. The product had MH$^+$=638, nmr(δ,DMSO-d6) 1.0(t,3H), 2.9(bd,2H), 3.1–3.25(m,2H), 3.4–3.5(m,2H), 4.0–4.2(m,3H), 4.3(bs,2H), 4.5–4.65(m, 2H), 4.75–4.82(m,1H), 5.48(d,1H), 5.59(d,1H), 5.82(bd, 1H), 5.95–6.05(m,1H), 7.1–7.4(m,15H), 7.97(bs,1H), 34) (1S)-1-deoxy-1-[6-[(2,2-diphenylethyl)amino]-2-[[1-(methoxymethyl)-2-phenylethyl]amino]-9H-purin-9-yl]-N-ethyl-β-D-ribofuranuronamide, from the product as in entry 34 in Example 20 and in Table 1 above, under conditions as in entry 34 in Table 2 below. The product was purified by preparative thin layer chromatography eluting with dichloromethane:ethanol:0.88 ammonia (150:8:1) (4 passes). The product had MH$^+$=652, nmr(δ,DMSO-d6) includes 0.97(t, 3H), 2.8–2.9(m,2H), 3.0–3.2(m,3H), 3.27(s,3H), 3.4–3.45 (m,2H), 4.0–4.1 and 4.1–4.2(m,2H), 4.23(bs,1H), 4.6–4.7 (m,2H), 5.8(bd,1H), 7.1–7.4(m,15H), 7.95(bs,1H).

35) 1-deoxy-1-[6-[(2,2-diphenylethyl)amino]-2-[[(2-methyl-1H-imidazol-1-yl)ethyl]amino]-9H-purin-9-yl]-N-ethyl-β-D-ribofuranuronamide, from the product as in entry 35 in Example 20 and in Table 1 above under conditions as in entry 35 in Table 2 below. The product was isolated by the evaporation of the reaction mixture and the addition of ether to give a solid. MH$^+$=612, nmr(δ,DMSO-d6) includes 1.0 (t,3H), 2.47(s,3H), 3.0–3.25(m,2H), 3.55–3.8(m,2H), 3.95–4.15(m,2H), 4.2(m,2H), 4.25–4.35(m,2H), 4.5–4.65 (m,2H), 5.85(d,1H), 7.15–7.4(m, 10H), 7.52(s,1H), 7.58(s, 1H), 8.12(bs,2H).

36) (1S)-trans]-1-deoxy-1-[2-[(3-N,N-dimethylamino) cyclopentylamino]-6-[(2,2-diphenylethyl)amino]-9H-purin-9-yl]-N-ethyl-β-D-ribofuranuronamide from the product as in entry 36 in Example 20 and in Table 1 above under conditions as in entry 36 in Table 2 below. The product was purified by preparative HPLC (20–60% acetonitrile). The product had MH$^+$=615, nmr(δ,DMSO-d6) includes 1.01(t, 3H), 1.6–1.8(m,2H), 2.05–2.3(m,4H), 2.75–2.81(m,6H), 3.1–3.2(m,2H), 4.0 4.15 m,1H), 4.15–4.22(m,1H), 4.3–4.5 (m,1H), 4.25(bs,1H), 4.55–4.67(m,2H), 5.82(d,1H), 7.15–7.4(m,10H), 9.45–9.6(m,1H).

37) 1-[2-[[(6-Amino-2-pyridinyl)methyl]amino]-6-[(2,2-diphenylethyl)amino]-9H-purin-9-yl]-1-deoxy-N-ethyl-β-D-ribofuranuronamide from the product as in entry 37 in Example 20 and in Table 1 above under conditions as in entry 37 in Table 2 below. The product was isolated by evaporation of the reaction mixture and the addition of ether to give a solid. The product had MH$^+$=610, nmr(δ,DMSO-d6) includes 1.02(t,3H), 3.05–3.15(m,2H), 4.15(m,1H), 4.28 (d,1H), 4.4–4.65(m,4H), 5.84(d,1H), 6.75(d,1H), 6.82(d, 1H), 7.1–7.35(10H), 7.83(t,1H), 7.15(s,1H).

TABLE 2

| Entry | starting material g. | trifluoroacetic acid, ml | water ml | reaction time |
|---|---|---|---|---|
| 1 | 0.114 | 1.0 | 0.5 | 3 h |
| 2 | 0.042 | 0.5 | 0.1 | 3 h |
| 3 | 0.161 | 2.0 | 0.5 | 1 h |
| 4 | 0.081 | 1.0 | 0.3 | 1.5 h |
| 5 | 0.197 | 2.0 | 0.5 | 2 h |
| 6 | 0.081 | 0.9 | 0.1 | 2 h |
| 7 | 0.210 | 2.7 | 0.3 | 1 h |
| 8 | 0.154 | 1.8 | 0.2 | 3 h |
| 9 | 0.069 | 1.0 | 0.1 | 2.75 h |
| 10 | 0.033 | 1.0 | 0.1 | 4.75 h |
| 11 | 0.150 | 9.0 | 1.0 | 3.5 h |
| 12 | 0.085 | 9.0 | 1.0 | 3.0 h |
| 13 | 0.120 | 9.0 | 1.0 | 3.0 h |
| 14 | 0.145 | 9.0 | 1.0 | 3.0 h |
| 15 | 0.149 | 9.0 | 1.0 | 3.0 h |
| 16 | 0.160 | 9.0 | 1.0 | 3.0 h |
| 17 | 0.121 | 11.4 | 0.6 | 3.5 h |
| 18 | 0.190 | 11.4 | 0.6 | 5.0 h |
| 19 | 0.117 | 4.5 | 0.5 | 2.0 h |
| 20 | 0.210 | 9.0 | 1.0 | 2.5 h |
| 21 | 0.026 | 5.0(HCl) | 1.0(dioxan) | 22 h |
| 22 | 0.111 | 7.0(HCl) | 15(dioxan) | 96 h |
| 23 | 0.152 | 4.5 | 0.5 | 3.3 h |
| 24 | 0.126 | 5.0 | 0.5 | 1.0 h |
| 25 | 0.200 | 9.0 | 1.0 | 3.0 h |
| 26 | 0.200 | 9.0 | 1.0 | 3.0 h |
| 27 | 0.054 | 2.5 | 0.5 | 1.0 h |
| 28 | 0.023 | 5.0(HCl) | 3.0(dioxan) | 46 h |
| 29 | 0.082 | 9.0 | 1.0 | 3.0 h |
| 30 | 0.042 | 1.0 | 0.1 | 5.75 h |
| 31 | 0.052 | 0.7 | 0.35 | 3.5 h |
| 32 | 0.140 | 9.0 | 1.0 | 2.5 h |
| 33 | 0.122 | 4.75 | 0.25 | 2.5 h |
| 34 | 0.153 | 5.0 | 0.5 | 2.0 h |
| 35 | 0.221 | 4.5 | 0.5 | 3.5 h |
| 36 | 0.038 | 2.0 | 0.4 | 2.0 h |
| 37 | 0.150 | 8.0 | 2.0 | 0.6 h |

Example 22

1-Deoxy-1-[6-[[(2,2-diphenylethyl)amino]-2-[(4-oxocyclohexyl)amino]-9H-purin-9-yl]-N-ethyl-2,3-O-(1-methylethylidene)-β-D-ribofuranuronamide A solution of (trans)-1-deoxy-1-[6-[(2,2-diphenylethyl) amino]-2-[(4-hydroxycyclohexyl)amino]-9H-purin-9-yl]-N-ethyl-2,3-O-(1-methylethylidene)-β-D-ribofuranuronamide (Example 20 and Table 1, entry no.3) (0.158 g, 0.246 mmol) in acetone (15 ml) was treated dropwise with Jones' reagent (ca 0.5 ml) until the red-brown colour persisted, and the reaction was stirred for a further 30 min. at 21° C. 2-Propanol (0.5 ml) was then added dropwise to disperse the colour. The mixture was basified to pH 9 with 2N-sodium hydroxide solution, and it was then diluted with water (10 ml) and extracted with ethyl acetate (4×15 ml). The combined organic layers were washed (brine), dried (Na$_2$SO$_4$) and evaporated to a foam which was purified on silica eluting with ethyl acetate:cyclohexane (9:1) to give the title compound (102 mg) as a white foam, MH$^+$=640.

Example 23

1-Deoxy-1-[6-[(2,2-diphenylethyl)amino]-2-[(4-oxocyclohexyl)amino]-9H-purin-9-yl]-N-ethyl-β-D-ribofuranuronamide 1-Deoxy-1-[6-[(2,2-diphenylethyl)amino]-2-[(4-oxocyclohexyl)amino]-9H-purin-9-yl]-N-ethyl-2,3-O-(1-methylethylidene)-β-D-ribofuranuronamide (0.133 g, 0.128 mmol) was treated with trifluoroacetic acid (1.95 ml) and water (0.5 ml). The mixture was swirled until a solution had formed, and it was then left to stand at 21° C. for 1.5 h. The solution was evaporated and the residue was purified by preparative HPLC (30 to 70% acetonitrile) to give the title compound (0.088 g) as a white foam, $MH^+$=600, nmr(δ, DMSO-d6) 1.00(t,3H), 1.80(m,2H), 2.20(m,2H), 2.35(m, 4H), 3.15(m,2H), 4.60(m,4H), 5.90(d,1H), 7.15 to 7.40(m, 10H), 8.25(m,3H).

Example 24

(3S)-1-Deoxy-1-[6-[(2,2-diphenylethyl)amino]-2-[[1-(phenylmethyl)-3-pyrrolidinyl]amino]-9H-purin-9-yl]-N-ethyl-2,3-O-(1-methylethylidene)-β-D-ribofuranuronamide A mixture of 1-[2-chloro-6-[(2,2-diphenylethyl)amino]-9H-purin-9-yl]-1-deoxy-N-ethyl-2,3-O-(1-methylethylidene)-β-D-ribofuranuronamide (0.4 g) and (3S)-(+)-1-benzyl-3-aminopyrrolidine (1.23 ml) was dissolved in dimethylsulphoxide (2 ml) and heated and stirred at 140° C. under nitrogen for 8 h. The reaction was allowed to cool to 20°, then partitioned between ethyl acetate and water. The organic layer was washed with water; and the combined aqueous layers extracted with ethyl acetate. The combined organic layers were washed with brine, dried over sodium sulphate and evaporated to a residue which was purified on a column of silica eluting with ethyl acetate:methanol (50:1) to give the title compound (0.336 g) as a white foam, nmr(δ,DMSO-d6) 0.55(m,3H), 1.35(s,3H), 1.50(s,3H), 1.70 (m,1H), 2.20(m,1H), 2.55 to 2.95(m,4H), 3.60(s,2H), 4.00 (m,2H), 4.40(m,2H), 4.55(m,1H), 5.40(m,2H), 6.15(s,1H), 6.45(m,1H), 7.10 to 7.35(m,17H), 7.75(s,1H).

Similarly prepared were:

(±)-1-deoxy-1-[6-[(2,2-diphenylethyl)amino]-2-[[1-(phenylmethyl)-3-pyrrolidinyl]amino]-9H-purin-9-yl]-N-ethyl-2,3-O-(1-methylethylidene)-β-D-ribofuranuronamide from the 2-chloropurine (0.200 g) and (±)-1-benzyl-3-aminopyrrolidine (0.614 ml) in DMSO (1 ml) at 140° C. for 24 h. The product was purified on silica eluting with ethyl acetate:methanol 50:1, $MH^+$=703.

1-deoxy-1-[6-[(2,2-diphenylethyl)amino]-2-[[1-(phenylmethyl)-4-piperidinyl]amino]-9H-purin-9-yl]-N-ethyl-2,3-O-(1-methylethylidene)-β-D-ribofuranuronamide from the 2-chloropurine (0.4 g) and 1-benzyl-4-aminopiperidine (1.5 g) at 135° for 24 h The product was purified on flash silica eluting with 1% methanol in ethyl acetate and dichloromethane:ethanol:0.880 ammonia (100:8:1), nmr(δ,CDCl₃) 0.7(t,3H), 1.35(s,3H), 1.4–1.65(m, 2H), 1.6(s,3H), 1.95–2.3(m,4H), 2.8–3.1(m,4H), 3.5(s,2H), 3.7–3.95(m,1H), 4.1–4.3(m,2H), 4.34(t,1H), 4.65(s,1H), 4.77(d,1H), 5.4–5.6(m,3H), 5.97(s,2H), 7.1–7.35(m, 15H), 7.4(s,1H).

Example 25

3R)-1-Deoxy-1-[6-[(2,2-diphenylethyl)amino]-2-[[1-(phenylmethyl)-3-pyrrolidinyl]amino]-9H-purin-9-yl]-N-ethyl-2,3-O-(1-methylethylidene)-β-D-ribofuranuronamide A mixture of 1-[2-chloro-6[(2,2-diphenylethyl)amino]-9H-purin-9-yl]-1-deoxy-N-ethyl-2,3-O-(1-methylethylidene)-β-D-ribofuranuronamide (0.4 g) and (3R)-(−)-1-benzyl-3aminopyrrolidine (1.23 ml) was dissolved in dimethylsulphoxide (2 ml) and heated and stirred at 140° C. under nitrogen for 5 h. The reaction was allowed to cool to 20°, then partitioned between ethyl acetate and water. The organic layer was washed with water, and the combined aqueous layers extracted twice with ethyl acetate. The combined organic layers were washed with brine, dried over sodium sulphate and evaporated to a residue which was purified on a column of silica eluting with ethyl acetate-:methanol (50:1) to give the title compound (0.335 g) as a white foam, nmr(δ,DMSO-d₆) 0.5(m,3H), 1.30(s,3H), 1.50 (s,3H), 1.75 to 2.25(m,2H), 2.75(m,4H), 3.57(s,2H), 3.85 to 4.65(m,6H), 5.35(m,1H), 5.50(m,1H), 6.20(s,1H), 6.50(m, 1H), 7.05 to 7.40(m,18H), 7.75(s,1H).

Example 26

(3S)-1-Deoxy-1-[6-[(2,2-diphenylethyl)amino]-2-[(3-pyrrolidinyl)amino]-9H-purin-9-yl]-N-ethyl-2,3-O-(1-methylethylidene)-β-D-ribofuranuronamide A solution of (3S)-1-deoxy-1-[(2,2-diphenylethyl)amino]-2-[[1-3-pyrrolidinyl]amino]-9H-purin-9-yl]-N-ethyl-2,3-O-(1-methylethylidene)-β-D-ribofuranuronamide (0.18 g) in methanol (20 ml) was added dropwise to a stirred suspension of 10% Palladium-on-carbon catalyst (0.027 g) in methanol (10 ml) under nitrogen. The mixture was treated with ammonium formate (0.08 g) and the reaction mixture was stirred and heated at reflux for 2.5 h. The cooled mixture was then filtered through Celite and the filtrate was evaporated to give a white foam which was purified by preparative HPLC (30 to 70% acetonitrile) to give the title compound as a white foam (0.166 g), $MH^+$=613.

Similarly prepared were:

(±)-1-deoxy-1-[6-[(2,2-diphenylethyl)amino]-2-[(3-pyrrolidinyl)amino]-9H-purin-9-yl]-N-ethyl-2,3-O-(1-methylethylidene)-β-D-ribofuranuronamide from (±)-1-deoxy-1-[6-[(2,2-diphenylethyl)amino]-2-[[1-(phenylmethyl)-3-pyrrolidinyl]amino]-9H-purin-9-yl]-N-ethyl-2,3-O-(1-methylethylidene)-β-D-ribofuranuronamide under identical conditions. The filtered reaction mixture was evaporated to give the product directly, $MH^+$=613.

(3R)-1-deoxy-1-[6-[(2,2-diphenylethyl)amino]-2-[(3-pyrrolidinyl)amino]-9H-purin-9-yl]-N-ethyl-2,3-O-(1-methylethylidene)-β-D-ribofuranuronamide from (3R)-1-deoxy-1-[6-[(2,2-diphenylethyl)amino]-2-[[1-(phenylmethyl)-3-pyrrolidinyl]amino]-9H-purin-9-yl]-N-ethyl-2,3-O-(1-methylethylidene)-β-D-ribofuranuronamide under identical conditions, except that 0.070 g of catalyst was used and the reaction time was 2 h. The filtered reaction mixture was evaporated, and the residue purified by preparative HPLC (30 to 70% acetonitrile) to give the product, $MH^+$=613.

Example 27

(3S)-1-Deoxy-1-[6-[(2,2-diphenylethyl)]amino]-2-[(3-pyrrolidinyl)amino]-9H-purin-9-yl]-N-ethyl-β-D-ribofuranuronamide (3S)-1-Deoxy-1-[6-[(2,2-diphenylethyl)amino]-2-[(3-pyrrolidinyl)amino]-9H-purin-9-yl]-N-ethyl-2,3-O-(1-methylethylidene)-β-D-ribofuranuronamide (0.19 g) was treated with trifluoroacetic acid (1.5 ml) and water (0.4 ml). The mixture was swirled until a solution had formed and it was then left to stand at 21° C. for 1.5 h. The reaction mixture was evaporated to a residue which was purified by preparative HPLC (20 to 60% acetonitrile) to give the title compound as a white foam (0.116 g). Analysis found, C, 47.4, H, 4.5, F, 17.1, N, 12.15, $H_2O$, 1.95%; $C_{30}H_{36}N_8O_4.2C_2F_3HO_2.H_2O$ requires C, 47.0, H, 4.5, F, 17.5, N, 12.3 $H_2O$,2.0%. nmr($\delta$,DMSO-d6) 1.00(t,3H), 1.95 to 2.30(m,2H), 3.05 to 3.50(m,6H), 4.05(m,2H), 4.20(m, 1H), 4.25(s,1H), 4.60(m,4H), 5.85(d,1H), 6.95(m,1H), 7.15 to 7.40(m,10H), 7.65(m,1H), 8.15(m,2H), 8.80(m,2H).

Similarly prepared were:

(±)-1-deoxy-1-[6-[(2,2-diphenylethyl)amino]-2-[(3-pyrrolidinyl)amino]-9H-purin-9-yl]-N-ethyl-β-D-ribofuranuronamide from (±)-1-deoxy-N-ethyl-2,3-O-(1-methylethylidene)-1-[6-[(2,2-diphenylethyl)amino]-2-[(3-pyrrolidinyl)amino]-9H-purin-9-yl]-β-D-ribofuranuronamide (0.186 g), trifluoracetic acid (2.6 ml) and water (0.65 ml) at 21° C. for 1 h. Purification by preparative HPLC (30 to 70% acetonitrile) gave the product, $MH^+$=573. nmr($\delta$,DMSO-d6) 1.00(t,3H), 2.10(m,2H), 3.25 (m,6H), 4.00 to 4.20(m,3H), 4.25(s,1H), 4.55(m,3H), 5.85 (d,1H), 6.95(m,1H), 7.15 to 7.40(m,10H), 7.65(m,1H), 8.10 (m,1H), 8.20(s,1H), 8.80(m,2H).

(3R)-1-deoxy-1-[6-[[(2,2-diphenylethyl)amino]-2-[(3-pyrrolidinyl)amino]-9H-purin-9-yl]-N-ethyl-β-D-ribofuranuronamide from (3S)-1-deoxy-1-[6-[(2,2-diphenylethyl)amino]-2-[(3-pyrrolidinyl)amino]-9H-purin-9-yl]-N-ethyl-2,3-O-(1-methylethylidene)-β-D-ribofuranuronamide (0.112 g), trifluoracetic acid (1.5 ml) and water (0.4 ml) at 21° C. for 1.25 h. Purification by preparative HPLC (20 to 60% acetonitrile) gave the product, $MH^+$=573. Analysis found, C, 46.9, H, 4.3, F, 17.1. N, 12.2; $C_{30}H_{36}N_8O_4.2C_2F_3HO_2.0.8H_2O$ requires C, 47.3, H, 4.5, F, 17.4, N, 12.45

1-deoxy-N-ethyl-1-[6-[(2,2-diphenylethyl)amino]-2-[(4-piperidinyl)amino]-9H-purin-9-yl]-β-D-ribofuranuronamide from 1-deoxy-1-[6-[(2,2-diphenylethyl)amino]-2-[[1-(phenylmethyl)-4-piperidinyl] amino]-9H-purin-9-yl]-N-ethyl-2,3-O-(1-methylethylidene)-β-D-ribofuranuronamide (0.15 g) by hydrogenation in ethyl acetate over 10% palladium-on-carbon for 14 days then deprotection with trifluoroacetic acid (9 ml) and water (1 ml) at 21° C. for 2.5 h. Purification by preparative HPLC (20–60% acetonitrile) gave the product, $MH^+$=587, nmr($\delta$, DMSO-d6) includes 1.02(t,3H), 1.55–1.8(m,2H), 1.95–2.2 (m,2H), 2.8–3.1(m,2H), 3.0–3.3(m,2H), 3.9–4.15(m,3H), 4.15–4.3(m,1H), 4.25(s,1H), 4.55(t,1H), 4.63(m,1H), 5.53 (bm,1H), 5.83(d,1H), 7.1–7.4(m,10H), 8.05(s,1H), 8.0–82 (m,1H), 8.2–8.4(m,1H), 8.4–8.6(m,1H).

Example 28

(3R)-1-Deoxy-1-[6-[(2,2-diphenylethyl)amino]-2-[[1-(phenylmethyl)-3-pyrrolidinyl]amino]-9H-purin-9-yl]-N-ethyl-2,3-O-(1-methylethylidene)-β-D-ribofuranuronamide A mixture of 1-[2-chloro-6-[(2,2-diphenylethyl)amino]-9H-purin-9-yl]-1-deoxy-N-ethyl-2,3-O-(1-methylethylidene)-β-D-ribofuranuronamide (0.4 g) and (3R)-(−)-1-benzyl-3aminopyrrolidine (1.23 ml) was dissolved in dimethylsulphoxide (2 ml) and heated and stirred at 140° C. under nitrogen for 5 h. The reaction was allowed to cool to 20°, then partitioned between ethyl acetate and water. The organic layer was washed with water, and the combined aqueous layers extracted twice with ethyl acetate. The combined organic layers were washed with brine, dried over sodium sulphate and evaporated to a residue which was purified on a column of silica eluting with ethyl acetate-:methanol (50:1) to give the title compound (0.335 g) as a white foam, nmr($\delta$,DMSO-d$_6$) 0.5(m,3H), 1.30(s,3H), 1.50 (s,3H), 1.75 to 2.25(m,2H), 2.75(m,4H), 3.57(s,2H), 3.85 to 4.65(m,6H), 5.35(m,1H), 5.50(m,1H), 6.20(s,1H), 6.50(m, 1H), 7.05 to 7.40(m,1H), 7.75(s,1H).

Example 29

(3R)-1-Deoxy-1-[6-[(2,2-diphenylethyl)amino]-2-[[1-(phenylmethyl)-3-pyrrolidinyl]amino]-9H-purin-9-yl]-N-ethyl-β-D-ribofuranuronamide (3R)-1-Deoxy-1-[6-[(2,2-diphenylethyl)amino]-2-[[1-(phenylmethyl)-3-pyrrolidinyl]amino]-9H-purin-9-yl]-N-ethyl-2,3-O-(1-methylethylidene)-β-D-ribofuranuronamide (0.125 g) was treated with trifluoroacetic acid (1.5 ml) and water (0.4 ml). The mixture was swirled until a solution had formed then it was left to stand at 21° C. for 1 h. The reaction mixture was evaporated to give a residue which was purified by column chromatography on silica eluting with dichloromethane:methanol (9:1) to give the title compound (0.173 g) as a white foam, MH+663; nmr($\delta$,DMSO-d6) 1.00(t,3H), 1.80 to 2.20(m,2H), 3.15(m,2H), 3.60(m,2H), 4.00(m,2H), 4.15(m,1H), 4.25(s,1H), 4.45(m,1H), 4.60(m,2H), 5.50(d, 1H), 5.60(d,1H), 5.80(d,, 1H), 6.45(m,1H), 7.10 to 7.40(m, 15H), 7.95(s,1H), 8.15(m,1H).

Similarly prepared were:

(±)-1-deoxy-1-[6-[(2,2-diphenylethyl)amino]-2-[[1-(phenylmethyl)-3-pyrrolidinyl]amino]-9H-purin-9-yl]-N-ethyl-β-D-ribofuranuronamide from (±)-1-deoxy-1-[6-[(2, 2-diphenylethyl)amino]-2-[[1-(phenylmethyl)-3-pyrrolidinyl]amino]-9H-purin-9-yl]-N-ethyl-2,3-O-(1-methylethylidene)-β-D-ribofuranuronamide (0.071 g) with trifluoroacetic acid (0.5 ml) and water (0.1 ml) for 25 h. The product was purified by preparative HPLC (30 to 70% acetonitrile),$MH^+$=663. Analysis found C, 52.8, H, 4.8, N, 11.35, F, 14.5%; $C_{37}H_{42}N_8O_4.2.5CF_3CO_2H.0.9H_2O$ requires C, 52.4, H, 4.85, N, 11.6, F, 14.8%.

(3S)-1-deoxy-1-[6-[(2,2-diphenylethyl)amino]-2-[[1-(phenylmethyl)-3-pyrrolidinyl]amino]-9H-purin-9-yl]-N-ethyl-β-D-ribofuranuronamide from (3S)-1-deoxy-1-[6-[(2, 2-diphenylethyl)amino]-2-[[1-(phenylmethyl)-3-pyrrolidinyl]amino]-9H-purin-9-yl]-N-ethyl-2,3-O-(1-methylethylidene)-β-D-ribofuranuronamide (0.125 g) with trifluoroacetic acid (1.5 ml) and water (0.4 ml) for 1.5 h. The product was purified by preparative HPLC (30 to 70% acetonitrile) to give 0.172 g, MH+663. nmr($\delta$,DMSO-d6) 1.00(t,3H), 1.75(m,1H), 2.25(m,1H), 2.60 to 3.00(m,2H), 3.15(m,2H), 3.60(m,2H), 3.90 to 4.70(m,7H), 5.50(d,1H), 5.60(d,1H), 5.80(d,1H), 6.45(m,1H), 7.10 to 7.40(m,15H), 7.95(s,1H), 8.15(m,1H).

1-deoxy-1-[6-[(2,2-diphenylethyl)amino]-2-[[1-(phenylmethyl)-4-piperidinyl]amino]-9H-purin-9-yl]-N-ethyl-β-D-ribofuranuronamide from 1-deoxy-1-[6-[(2,2-diphenylethyl)amino]-2-[[1-(phenylmethyl)-4-piperidinyl] amino]-9H-purin-9-yl]-N-ethyl-2,3-O-(1-methylethylidene)-β-D-ribofuranuronamide (0.07 g) in trifluoroacetic acid (9.5 ml) and water (0.5 ml) for 3 h. The mixture was evaporated to dryness and the residue purified by reverse phase HPLC (20–60% acetonitrile). $MH^+$=677, nmr($\delta$, DMSO-d6) includes 1.0(t,3H), 1.55–1.8(m,2H), 1.85–2.15 (m,1H), 2.05–2.3(m,2H), 2.8–3.15(m,1H), 3.05–3.3(m,3H), 3.35–3.55(m,2H), 4.0–4.15(m,2H), 4.2(m,1H), 4.28(m,3H), 4.5(t,1H), 4.5(t,1H), 4.6(m,1H), 5.83(m; 1H), 7.1–7.4(m, 10H), 7.5(s,5H), 8.12(bs,2H).

Example 30

(±)-1-Deoxy-1-[6-[(2,2-diphenylethyl)amino]-2-[(1-ethyl-3-pyrrolidinyl)amino]-9H-purin-9-yl]-N-ethyl-2,3-O-(1-methylethylidene)-β-D-ribofuranuronamide A solution of (±)-1-deoxy-1-[6-[(2,2-diphenylethyl) amino]-2-[[1-(phenylmethyl)-3-pyrrolidinyl]amino]9H- purin-9-yl]-N-ethyl-2,3-O-(1-methylethylidene)-β-D-ribofuranuronamide (0.123 g, 0.175 mmol) in ethanol (analytical reagent grade) (10 ml) was added slowly to a stirred suspension of 10% palladium-on-carbon catalyst (45 mg) in ethanol (2 ml). The mixture was then hydrogenated over 2.5 days. The filtered solution was then evaporated and the residue was again hydrogenated in ethanol (12 ml) over 10% palladium-on-carbon (40 mg) for 2 weeks, but there was still no apparent reaction (tlc). The filtered mixture was evaporated and the residue was again hydrogenated over 10% palladium-on-carbon in ethanol at 250 p.s.i. pressure for 5 days. The filtered mixture was evaporated and the residue was purified by preparative HPLC (30 to 70% acetonitrile) to give the title compound (0.068 g) as a white foam, $MH^+=641$.

Example 31

(±)-1-Deoxy-1-[6-[(2,2-diphenylethyl)amino]-2-[(1-ethyl-3-pyrrolidinyl)amino]-9H-purin-9-yl]-N-ethyl-β-D-ribofuranuronamide (±)-1-Deoxy-1-[6-[(2,2-diphenylethyl)amino]-2-[(1-ethyl-3-pyrrolidinyl)amino]-9H-purin-9-yl]-N-ethyl-2,3-O-(1-methylethylidene)-β-D-ribofuranuronamide (0.060 g) was treated with trifluoroacetic acid (0.5 ml) and water (0.1 ml), and the resulting solution was left to stand at 21° C. for 1 h. The solution was evaporated and the residue was purified by preparative HPLC (30 to 70% acetonitrile) to give the title compound (0.053 g) as a white foam, $MH^+$= 601, nmr(δ,DMSO-d6) 1.00(t,3H), 1.20(m,3H), 2.10(m, 2H), 3.15(m,5H), 4.05(m,1H), 4.25(m,2H), 4.55(m,4H), 5.85(d,1H), 7.15 to 7.40(m,10H), 8.15(m,2H), 9.70(m,1H).

Prepared by a similar method to Examples 30 and 31 was:

1-deoxy-1-[6-[(2,2-diphenylethyl)amino]2-[(1-ethyl-4piperidinyl)amino]-9H-purin-9-yl]-N-ethyl-β-D-ribofuranuronamide from 1-deoxy-1-[6-[(2,2-diphenylethyl)amino]-2-[[1-(phenylmethyl)-4-piperidinyl]amino]-9H-purin-9-yl]-N-ethyl-2,3-O-(1-methylethylidene)-β-D-ribofuranuronamide (0.14 g) by hydrogenation in ethanol and deprotection with trifluoroacetic acid:water. The product was purified on reversed phase HPLC (20–60% acetonitrile). $MH^+=587$, nmr(δ,CDCl₃) includes 1.0(t,3H), 123(t,3H), 1.5–1.7(m,1H), 1.85–22(m,1H), 2.1–2.3(m,1H), 2.75–3.05(m,1H), 3.0–3.25(m,4H), 3.52(bd,1H), 4.25(s, 1H), 4.53(t,1H), 4.6(m,1H), 5.85(d,1H), 7.15–7.4(m,10H), 8.13(bs,2H).

Example 32

(trans)-1-[2-[(4-Aminocyclohexyl)amino]6-[(2,2-diphenylethyl)amino]-9H-purin-9-yl]-1-deoxy-N-ethyl-2,3-O-(1-methylethylidene)-β-D-ribofuranuronamide A mixture of 1-[2-chloro-6-[(2,2-diphenylethyl)amino]-9H-purin-9-yl]-1-deoxy-N-ethyl-2,3-O-(1-methylethylidene)-β-D-ribofuranuronamide (0.4 g) and trans-1,4-diaminocyclohexane (0.811 g) was dissolved in dimethylsulphoxide (2.0 ml) and heated and stirred at 140° C. under nitrogen for 4 h. The reaction mixture was allowed to cool to 21° and was then partitioned between (1:1) ethyl acetate and water (40 ml). The organic layer was separated and washed with water. The combined aqueous layers were extracted twice with ethyl acetate, and the total organic solution was washed with brine, dried over sodium sulphate and evaporated in vacuo to a residue which was purified by preparative HPLC (30 to 70% acetonitrile) to give the title compound (0.342 g) as a white foam $MH^+=641$.

Similarly prepared were:

1) 1-[2-[(3-aminopropyl)amino]-6-[(2,2diphenylethyl)amino]-9H-purin-9-yl]-1-deoxy-N-ethyl-2,3-O-(1-methylethylidene)-β-D-ribofuranuronamide, using 1,3-diaminopropane as the nucleophile as in entry 1 in Table 3 below. The product had $MH^+=601$.

2) 1-deoxy[2-[(2,2-dimethyl-3-aminopropyl)amino]-[6-[(2,2-diphenylethyl)amino]-9H-purin-9-yl]-N-ethyl-2,3-O-(1-methylethylidene)-β-D-ribofuranuronamide, using 2,2-dimethyl-1,3-propanediamine as the nucleophile as in entry 2 in Table 3 below. The product had $MH^+=629$.

3) [(1α,2β,3β)-(±)]-1-[2-[(3-acetylamino-2-hydroxycyclopentyl)amino]-6[(2,2-diphenylethyl)amino]-9H-purin-9-yl]-1-deoxy-N-ethyl-2,3-O-(1-methylethylidene)-β-D-ribofuranuronamide, using [(1α,2β, 3β)-(±)]-3-acetylamino-2-hydroxycyclopentylamine[1] as the nucleophile as in entry 3 in Table 3 below, $MH^+=685$.

1. R. Vince and S. Daluge, *J. Med. Chem.*, 1974, 17, 578

TABLE 3

| Entry | 2-chloropurine g. | nucleophile g. | DMSO ml | temp. °C. | reaction time |
|---|---|---|---|---|---|
| 1 | 0.30 | 0.395 | 1.5 | 140 | 1.5 h |
| 2 | 0.30 | 0.54 | 1.5 | 140 | 1.5 h |
| 3 | 0.20 | 0.25 | 0.8 | 140 | 18 h |

Example 33

(trans)-1-[2-[(4-Aminocyclohexyl)amino]-6-[(2,2-diphenylethyl)amino]-9H-purin-9-yl]-1-deoxy-N-ethyl-β-D-ribofuranuronamide (trans)-1-[2-[(4-Aminocyclohexyl)amino]-6-[(2,2-diphenylethyl)amino]-9H-purin-9-yl]-1-deoxy-N-ethyl-2,3-O-(1-methylethylidene)-β-D-ribofuranuronamide (0.277 g) was treated with trifluoroacetic acid (2.0 ml) and water (0.5 ml). The mixture was swirled until a solution had formed, then it was left to stand at 21° C. for 2 h. The reaction mixture was evaporated in vacuo to a residue which was purified by preparative HPLC (30 to 70% acetonitrile) to give the title compound (0.24 g) as a white foam, $MH^+=601$; nmr(δ,DMSO-d6) 1.00(t,3H), 1.40(m,4H), 2.00(m,4H), 3.10(m,3H), 3.70(m,1H), 4.15(m,3H), 4.30(s,1H), 4.55(m, 5H), 5.80(d,1H), 7.15 to 7.40(m,10H), 7.80(m,3H), 8.15(m, 2H).

Similarly prepared were:

1) 1-[2-[(3-Aminopropyl)amino]-6-[(2,2-diphenylethyl)amino]-9H-purin-9-yl]-1-deoxy-N-ethyl-β-D-ribofuranuronamide, from the product from entry 1 in Table 3 above, as in entry 1 in Table 4 below. The product had $MH^+=561$, nmr(δ,DMSO-d6) includes 1.90(m,2H), 2.85(m, 2H), 3.15(m,2H).

2) 1-deoxy-[2-[(2,2-dimethyl-3-aminopropyl)amino]-6-[(2,2-diphenylethyl)amino]-9H-purin-9-yl]-N-ethyl-β-D-ribofuranuronamide, from the product from entry 2 in Table 3 above, as in entry 2 in Table 4 below. The product had $MH^+=589$, nmr(δ,DMSO-d6) includes 0.95(m,9H), 2.70(m, 2H), 3.05 to 3.45(m,4H).

3) [(1α,2β,3β)-(±)]-1-[2-[(3-Acetylamino-2-hydroxycyclopentyl)amino]-6-[(2,2-diphenylethyl)amino]-9H-purin-9-yl]-1-deoxy-N-ethyl-β-D-ribofuranuronamide from the product from entry 3 in Table 3 above, as in entry 3 in Table 4 below, $MH^+=645$; nmr(δ,DMSO-d6) includes 1.32 to 1.62(m,2H), 1.78 to 1.98(m,1H), 1.82(s,3H), 2.07 to 2.28(m,1H), 3.89(br.s,1H), 4.1(m,1H), 4.65(br.s,1H), 4.92

(br.s,1H), 6.51(br.s,1H), 7.57(d,1H), the last tree signals being exchangeable with $D_2O$.

TABLE 4

| Entry | starting material g. | trifluoroacetic acid, ml | water ml | reaction time |
|---|---|---|---|---|
| 1 | 0.2275 | 2.0 | 0.5 | 1.5 h |
| 2 | 0.2644 | 2.0 | 0.5 | 1.5 h |
| 3 | 0.098 | 1.0 | 0.1 | 2 h |

Example 34

1-[(2-(Cyclopentylamino)-6-[(2,2-diphenylethyl) amino]-9H-purin-9-yl]-1-deoxy-N-ethyl-β-D-ribofuranuronamide A mixture of 1-[2-chloro-6-[(2,2-diphenylethyl)amino]-9H-purin-9-yl]-1-deoxy-N-ethyl-β-D-ribofuranuronamide (0.407 g, 0.78 mmol) and cyclopentylamine (6 ml) was stirred and refluxed under nitrogen for 26 h. Sodium hydrogen carbonate (0.600 g) was added and the mixture was stirred at 21° C. for 0.5 h. The mixture was evaporated and purified on flash silica eluting with dichloromethane:ethanol:0.880 ammonia (75:8:1) to give an impure product which was purified on flash silica eluting with 2 to 5% methanol in ethyl acetate to give a product which was triturated with ether to give the title compound (0.205 g) as a white solid, m.p. 122° to 128° C. Found C, 64.8, H, 6.7, N, 17.0% $C_{51}H_{37}N_7O_4$ requires C, 65.1, H, 6.5, N, 17.15%.

Similarly prepared was:

(1R-trans)-1-deoxy-1-[6-[(2,2-diphenylethyl)amino]-2-[ (2-hydroxycyclopentyl)amino]-9H-purin-9-yl]-N-ethyl-β-D-ribofuranuronamide, from the 2-chloropurine (0.35 g) and (R)-(trans)-2aminocyclopentanol[1] (1.0 g) at 130° C. for 10 h. The product was purified on silica eluting with ethyl acetate:methanol 19:1 and then on silica eluting with dichloromethane:methanol:0.880 ammonia (100:8:1). The product had m.p. 122° to 130° C. Analysis found C, 62.6, H, 6.2, N, 16.2%; $C_{31}H_{37}N_7O_5.0.4H_2O$ requires C, 62.6, H, 6.4, N, 16.5%.

1. L. E. Overman and S. Sugai, *J. Org. Chem.*, 1985, 50, 4154

Example 35

1-Deoxy-1-[6-[(2,2-diphenylethyl)amino]-2-[(2-hydroxyphenyl)amino]-9H-purin-9-yl]-N-ethyl-β-D-ribofuranuronamide A mixture of 1-[2-chloro-6-[(2,2-diphenylethyl)amino]-9H-purin-9-yl]-1-deoxy-N-ethyl-β-D-ribofuranuronamide (0.20 g, 0.038 mmol), 2-aminophenol (0.20 g 1.83 mmol), 1,8-diazabicyclo[5.4.0]undec-7-ene (0.052 ml, DBU) and dimethylsulphoxide (1 ml) was stirred and heated at 140° C. under nitrogen for 6 h, and then left at 21° C. overnight. The mixture was partitioned between ethyl acetate (200 ml) and water (40 ml). The aqueous layer was extracted with more ethyl acetate (50 ml) and the total organic solution was washed (water, 20 ml), dried ($Na_2SO_4$) and evaporated. The residue was purified on flash silica eluting with dichloromethane:methanol (19:1), and then by preparative TLC (20×20 cm plate with 2 mm layer of Kieselgel 60 $F_{254}$; Art 5717) in dichloromethane:ethyl acetate:ethanol 9:9:2, and then by preparative HPLC (30 to 70% acetonitrile) to give the title compound (0.018 g) as a cream foam, $MH^+$=596. Analysis found: C, 52.2, H, 4.3, N, 11.8; $C_{32}H_{33}N_7O_5.2CF_3CO_2H$ requires C, 52.5, H, 4.3, N, 11.9%

Similarly prepared was:

1-deoxy-1-[6-[(2,2-diphenylethyl)amino]-2-[(4-hydroxyphenyl)amino]-9H-purin-9-yl]-N-ethyl-β-D-ribofuranuronamide from the 2-chloropurine (0.135 g), 4-aminophenol (0.135 g), DBU (0.035 ml) and DMSO (0.6 ml) at 140° C. for 10 h. The product was extracted into dichloromethane, and purification was by preparative TLC and preparative HPLC (same system as above). The product had $MH^+$=596 and nmr(δ,DMSO-d6) including 7.09(d,2H) and 7.27(d,2H).

Example 36

1-Deoxy-1-[6-[(2,2-diphenylethyl)amino]-2-[[2-(1H-imidazol-4-yl)ethyl]amino]-9H-purin-9-yl]-N-ethyl-β-D-ribofuranuronamide hydrochloride salt A solution of 1-[2-chloro-6-[(2,2-diphenylethyl)amino]-9H-purin-9-yl]-1-deoxy-N-ethyl-β-D-ribofuranuronamide (0.155 g, 0.296 mmol) and histamine (0.22 g) in dimethylsulphoxide (1.5 ml) was heated at 120° C. for 16 h. The mixture was cooled and diluted with ethyl acetate (50 ml) then washed with water (50 ml). The aqueous phase was extracted with ethyl acetate (50 ml) and the combined organic phase was washed with water (50 ml), dried ($MgSO_4$) and evaporated to leave a solid which was treated with 2N hydrochloric acid (2 ml) in methanol (30 ml) and the solution was evaporated to leave the title compound (0.15 g, 80%) as a solid. $MH^+$=598, nmr(δ,DMSO-d6) includes 1.02(t,3H), 3.0(m,2H), 3.13(m,2H), 3.7(m,2H), 4.2 (m,2H), 4.85(s,1H), 4.55(m,3H), 5.9(d,1H), 7.1–7.6(m, 12H), 8.45(s,1H), 9.05(s,1H), 14.3(m,1H).

Example 37

N-[6-[(2,2-Diphenylethyl)amino]-9-N-ethyl-2,3-O-(1-methylethylidene)-β-D-ribofuranuronamidosyl]-9H-purin-2-yl]-L-phenylalanine, 1,1-dimethylethyl ester and N-[6-[(2,2-diphenylethyl)amino]-9-N-ethyl-2,3-O-(1-methylethylidene)-β-D-ribofuranuronamidosyl]-9H-purin-2-yl]-D-phenylalanine, 1,1-dimethylethyl ester A mixture of 1-[2-chloro-6-[(2,2-diphenylethyl)amino]-9H-purin-9-yl]-1-deoxy-N-ethyl-2,3-O-(1-methylethylidene)-β-D-ribofuranuronamide (0.402 g, 0.714 mmol) and L-phenylalanine 1,1-dimethylethyl ester (0.3 g) was heated at 130° C. for 17 h when more amine (0.4 g) was added. Heating was continued for a further 29 h then more amine (0.37 g then 0.4 g after 3 h) was added and the reaction left for a further 74 h at 130° C. The cooled residue was purified by flash chromatography using 70% ethyl acetate in cyclohexane and preparative HPLC (70–100% acetonitrile) and the resultant solution brought to pH 8 with sodium hydrogen carbonate. The mixture was reduced in volume and the product was extracted with ethyl acetate(3× 75 ml) in the presence of salt solution. The extract was dried and evaporated to give the mixture of title compounds (0.2 g) as a solid, $MH^+$=748.

Example 38

N-[6-[(2,2-Diphenylethyl)amino]-9-(N-ethyl-β-D-ribofuranuronamidosyl)-9H-purin-2-yl]-L-phenylalanine and N-[6-[(2,2-diphenylethyl)amino]-9-(N-ethyl-β-D-ribofuranuronamidosyl)-9H-purin-2-yl]-D-phenylalanine A solution of N-[6-[(2,2-diphenylethyl)amino]-9-N-ethyl-2,3-O-(1-methylethylidene)-β-D- ribofuranuronamidosyl]-9H-purin-2-yl]-L-phenylalanine, 1,1-dimethylethyl ester and N-[6-[(2,2-diphenylethyl)amino]-9-[-N-ethyl-2,3-O-(1-methylethylidene)-β-D-ribofuranuronamidosyl]-9H-purin-2-yl]-D-phenylalanine 1,1-dimethylethyl ester (0.152 g, 0.203 mmol) in 9:1 trifluoroacetic acid:water 5 ml) was kept at room temperature for 3.5 h then evaporated to give a solid which was purified by preparative HPLC (48% acetonitrile isocratic).

Isomer 1 (0.019 g, 14%) had MH$^+$=652, nmr(δ,DMSO-d6) includes 0.98(t,3H), 3.0–3.2(m,4H), 4.0–4.15(m,3H), 4.27(bs,1H), 4.5–4.65(m,2H), 4.7–4.8(m,1H), 5.81(bd,1H), 7.1–7.4(m,15H), 8.05–8.15(bs,1H).

Isomer 2 (0.0466 g, 35%) had MH$^+$=652, nmr(δ,DMSO-d6) includes 0.8–0.95(m,3H), 3.0–3.2(m,4H), 4.0–4.15(m, 3H), 4.25(bs,1H), 4.55–4.7(m,2H), 4.7–4.8(m,1H), 5.8(bd, 1H), 7.1–7.4(m,15H), 8.05–8.15(bs,1H).

Example 39

(trans)-1-[2-[(4-Aminocyclohexyl)amino]-6-[(2,2-diphenylethyl)amino]-9H-purin-9-yl]-1-deoxy-N-ethyl-β-D-ribofuranuronamide A solution of 1-[2-chloro-6-[(2,2-diphenylethyl)amino]-9H-purin-9-yl]-1-deoxy-N-ethyl-β-D-ribofuranuronamide (18.0 g, 0.0344 mole) in dimethylsulphoxide (100 ml) was heated at 120° under nitrogen with trans-cyclohexane-1,4-diamine (29.5 g, 0.258 mole) for 48 h. The cooled mixture was diluted with ethyl acetate (1 l) and water (500 ml). The aqueous phase, which contained a considerable amount of oil, was separated from the ethyl acetate. The water was decanted from the oil and then extracted with ethyl acetate (100 ml) and the ethyl acetate solutions were combined, dried (MgSO4) and evaporated to leave a froth (9.2 g). The oil was dissolved in ethanol (500 ml) and the solution was evaporated to leave a solid which was dried in vacuo. The solid was bleached with ethanol (3×200 ml) and the filtered solution was evaporated in vacuo to leave a froth (11.1 g). The two product fractions were combined and purified by column chromatography on flash silica eluted with dichloromethane:ethanol:0.88 ammonia (30:8:1) to give the title compound (17.11 g). The product had nmr(δ,CDCl$_3$) including 1.1(t3H), 1.1–1.35(m,4H), 1.75–1.95(m,2H), 1.95–2.2 (m,2H), 3.05–3.25(m,1H), 3.2–3.5(m,1H), 4.5–4.8(m,1H), 4.1–4.3(m,2H), 4.35(t,1H), 4.5(d,1H), 4.67(d,1H), 4.8(m, 2H), 5.7–5.9(m,1H), 5.8(d,1H), 7.1–7.4(m,10H), 7.47(s, 1H).

Example 40

(trans)-1-[2-[(4-Aminocyclohexyl)amino]-6-[(2,2-diphenylethyl)amino]-9H-purin-9-yl]-1-deoxy-N-ethyl-β-D-ribofuranuronamide hydrochloride A solution of (trans)-1-[2-[(4-Aminocyclohexyl)amino]-6-[(2,2-diphenylethyl)amino]-9H-purin-9-yl]-1-deoxy-N-ethyl-β-D-ribofuranuronamide (11.05 g, 0.0184 mole) in ethanol (120 ml) was stirred during the addition of 1M hydrogen chloride in ether (18.4 ml, 0.0184 mole). An initial precipitate redissolved on complete addition and the mixture was stirred for 15 min before ether (400 ml) was added. The resulting precipitate was stirred for a further 15 min then collected by filtration under nitrogen and dried in vacuo at 60° over phosphorus pentoxide. The solid (10.1 g) was crystallised from isopropanol (120 ml) to give the title compound (7.95 g). The product had MH$^+$=601, nmr(δ, DMSO-d6) includes 1.0(t,3H), 1.2–1.5(m,4H), 1.9–2.1(m, 4H), 2.9–3.1(m,1H), 3.0–3.3(m,2H), 3.6–3.8(m,1H), 3.9–4.2(m,2H), 4.1–4.2(m,1H), 4.25(s,1H), 4.5–4.6(m,1H), 4.6–4.7(m,1H), 5.4–5.7(m,2H), 5.8(d,1H), 6.2–6.4(m,1H), 7.1–7.4(m,10H), 7.95(bs,1H), 7.8–8.2(m,3H).

Example 41

1-Deoxy-1-[6-[(2,2-diphenylethyl)amino]-2-[[2-methyl-1H-imidazol-4-yl)ethyl]amino]-N-ethyl-9H-purin-9-yl]-β-D-ribofuranuronamide A solution of sodium hydroxide (242 mg, 6.05 mmol) in methanol (20 ml) was added to a suspension of 1-methylhistamine dihydrochloride (600 mg, 3.029 mmol) in methanol (10 ml). The mixture was stirred for 0.5 h to give a fine precipitate. The mixture was blown dry with nitrogen. A solution of 1-[2-chloro-6-[(2,2-diphenylethyl)amino]-9H-purin-9-yl]-1-deoxy-N-ethyl-β-D-ribofuranuronamide (253 mg, 0.484 mmol) in dimethylsulphoxide (2 ml) was added and the mixture was heated at 125° for 24 h under nitrogen. The cooled mixture was partitioned between ethyl acetate (50 ml) and water (20 ml). The aqueous phase was extracted with ethyl acetate (20 ml) and the combined organic phase was washed with water (50 ml), dried (MgSO4) and evaporated to leave a solid which was purified by preparative HPLC (30–70% acetonitrile) to give the title compound (251 mg). The product had MH$^+$=612, nmr(δ,DMSO-d6) includes 1.0(t,3H), 2.95–3.05(m, 2H), 3.05–3.25(m,2H), 3.5–3.85(m,2H), 3.8(s,3H), 4.38(s, 1H), 4.5–4.65(m,2H), 5.85(d,1H), 7.15–7.4(m,10H) 7.45(s, 1H), 8.13(s,1H), 8.1–8.3(m,1H), 8.95(s,1H).

Similarly prepared were:

1) 1-deoxy-1-[6-[(2,2-diphenylethyl)amino]-2-[[2-[(3-methyl-3H-imidazol-4-yl)ethyl]amino]-9H-purin-9-yl]-N-ethyl-β-D-ribofuranuronamide using 3-methylhistamine (prepared by basification of the dihydrochloride) as the nucleophile as in entry 1 in Table 5 below. The product was purified by preparative HPLC (30 to 70% acetonitrile). The product had MH$^+$=612, nmr(δ,DMSO-d6) includes 1.0(t, 3H), 2.85–3.05(m,2H), 3.05–3.25(m,2H), 3.55–3.85(m,2H), 3.78(s,3H), 3.95–4.15(m,2H), 4.18 and 4.3(bs,3H), 4.45–4.65(m,2H), 5.85(d,1H), 7.15–7.4(m,10H), 7.48(s, 1H), 8.1–8.3(m,2H), 9.0(s,1H).

2) 1-deoxy-1-[6-[(2,2-diphenylethyl)amino]-2-[[2-(1H-imidazol-2-yl)ethyl]-amino]-9H-purin-9-yl]-N-ethyl-β-D-ribofuranuronamide using 2-(1H-imidazol-2 -yl)ethylamine[1] (prepared by basification of the dihydrochloride) as the nucleophile as in entry 2 in Table 5 below. The product was purified by preparative HPLC (25 to 56% acetonitrile over 14 min. then to 90% at 16 min.). The product had MH$^+$=598, nmr(δ,DMSO-6) includes 0.91(t, 3H), 3.90–4.05(m,2H), 4.10–4.16(m,1H), 4.45–4.55(m,2H), 5.77(d,1H), 7.10–7.30(m,12H), 7.40–7.50(m,2H), 8.00–8.10(m,2H).

1. Durant, G. J. et al, *Chem. Comm.*, 1968, (2), 108–110.

3) 1-deoxy-1-[6-[(2,2-diphenylethyl)amino]-2-[[2-(1H-imidazol-2-yl)methyl]-amino]-9H-purin-9-yl]-N-ethyl-β-D-ribofuranuronamide using (1H-imidazol-4-yl)methylamine[1] (prepared by basification of the dihydrochloride) as the nucleophile as in entry 3 in Table 5 below. The product was purified by preparative HPLC (25 to 56% acetonitrile over 14 min. then to 90% at 16 min.). The product had MH$^+$=584, nmr(δ,DMSO-d6) includes 1.07(t,3H), 3.10–3.30(m,2H), 4.00–4.10(m,2H), 4.22–4.27(m,1H), 4.34(bs,1H), 4.50–4.70(m,4H), 5.92(d,1H), 7.20–7.40(m,14H), 7.51(s, 1H), 8.20(bs,1H), 9.05(bs,1H).

1. Turner, R. A., Huebner, C. F. and Scholz C. R., *J. Am. Chem. Soc.*, 1949, 71, 2801–2803.

4) 1-deoxy-1-[6-[(2,2-diphenylethyl)amino]-2-[[3-(1H- imidazol-4-yl)propyl]amino]-9H-purin-9-yl]-N-ethyl-β-D-ribofuranuronamide using 3-(1H-imidazol-4-yl)propylamine[1] (prepared by basification of the dihydrochloride) as the nucleophile as in entry 4 in Table 5 below. The product was purified by preparative HPLC (25 to 56% acetonitrile over 14 min. then to 90% at 16 min.). The product had MH$^+$=612, nmr(δ,DMSO-d6) includes 1.01(t,3H), 1.90–2.00(m,2H), 2.70(bt,4H), 3.10–3.25(m,2H), 4.00–4.10(m,2H), 4.15–4.24(m,1H), 4.30(s,1H), 4.55–4.65(m,4H), 5.84(d,1H), 7.15–7.35(m,10H), 7.42(s,1H), 8.12(s,1H), 8.15–8.25(m,1H), 8.98(s,1H).

1. Adger, B. M. and Surtees, J., Synth. Comm., 1987, 17(2), 223–227.

5) 1-deoxy-1-[6-[(2,2-diphenylethyl)amino]-2-[[(1H-imidazol-1-yl)ethyl]amino]-9H-purin-9-yl]-N-ethyl-β-D-ribofuranuronamide using 2-(1H-imidazol-1-yl)ethylamine[1] (prepared by basification of the dihydrobromide) as the nucleophile as in entry 5 in Table 5 below. The product was purified by preparative HPLC (27 to 54% acetonitrile over 14.5 min.). The product had MH$^+$=598, nmr(δ,DMSO-d6) includes 0.98(t,3H), 3.05–3.20(m,2H), 4.00–4.10(2H), 4.15–4.25(m,1H), 4.27(bs,1H), 4.38–4.48(m,2H), 4.50–4.62(m,2H), 5.83(d,1H), 6.74–6.85(m,1H), 7.15–7.40(10H), 7.60–7.70(m,2H), 7.72(s,1H), 8.10–8.20(m,2H), 9.05(bs,1H).

1. Cuadro, A. M. et al., Synth. Comm., 1991, 21(4), 535–544.

6) 1-deoxy-1-[6-[(2,2-diphenylethyl)amino]-2-[[2-(pyrid-3-yl)ethyl]amino]-9H-purin-9-yl]-N-β-D-ribofuranuronamide using 3-(2-aminoethyl)pyridine[1] as the nucleophile as in entry 6 in Table 5 below. The product was purified by preparative HPLC (20 to 60% acetonitrile). The product had MH$^+$=609, nmr(δ,DMSO-d6) includes 1.0(t,3H), 2.95–3.25(m,4H), 3.55–3.8(m,2H), 5.87(d,1H), 7.15–7.4(m,10H), 7.8(dd,1H), 8.0–8.5(m,3H), 8.65–8.8(m,2H), 1.Soeda, Y. and Yamamoto, I., Agr. Biol. Chem. (Tokyo), 1968, 32(6), 747–752.

7) 1-deoxy-1-[6-[(2,2-diphenylethyl)amino]-2-[[2-(pyrid-4-yl)ethyl]amino]-9H-purin-9-yl]-N-ethyl-β-D-ribofuranuronamide using 4-(2aminoethyl)pyridine[1] as the nucleophile as in entry 7 in Table 5 below. The product was purified by preparative HPLC (25 to 47.5% acetonitrile). The product had MH$^+$=609, nmr(δ,DMSO-d6) includes 1.09(t,3H), 3.00–3.22(m,4H), 4.00–4.10(m,2H), 4.15–4.21(m,1H), 4.30(bs,1H), 4.52–4.62(m,2H), 5.83(d,1H), 7.15–7.35(m,10H), 7.81(d,2H), 8.10–8.25(m,2H), 8.71(d,2H).

1. Magnus, G. and Levine, R. J. Am. Chem. Soc., 1956, 78, 4127–4130.

8) 1-deoxy-1-[6-[(2,2-diphenylethyl)amino]-2-[[(pyrid-3-yl)methyl]amino]-9H-purin-9-yl]-N-ethyl-β-D-ribofuranuronamide using 3-aminomethylpyridine as the nucleophile as in entry 8 in Table 5 below. The product was purified by preparative HPLC (25 to 56% acetonitrile over 14 min. then to 90% at 16 min.). The product had MH$^+$=595, nmr(δ, DMSO-d6) includes 1.01(t,3H), 3.10–3.25(m,2H), 4.29(d, 1H), 4.40–4.56(m,3H), 4.65–4.72(bs,2H), 5.83(d,1H), 7.10–7.30(m,10H), 7.75–7.81(m,2H), 8.13–8.30(m,3H), 8.68(d,1H), 8.75(bs,1H).

9) 1-deoxy-1-[6-[(2,2-diphenylethyl)amino]-2-[[(2-(1H-1,2,4-triazol-3-yl)methyl]amino]-9H-purin-9-yl]-N-ethyl-β-D-ribofuranuronamide using 3-(2-aminoethyl)-1,2,4-triazole[1] (prepared by basification of the dihydrochloride) as the nucleophile as in entry 9 in Table 5 below. The product was purified by preparative HPLC (20 to 65% acetonitrile). The product had MH$^+$=599, nmr(δ,DMSO-6) includes 1.01(t, 3H), 3.00–3.20(m,4H), 4.35(d,1H), 4.50–4.65(m,3H), 5.87(d,1H), 7.10–7.40(m,10H), 8.20–8.50(m,3H).

1. Ainsworth, C. and Jones, R., J. Am. Chem. Soc., 1953, 75, 4915–4918.

10) 1-deoxy-1-[6-[(2,2-diphenylethyl)amino]-2-[[2-(1H-1,2,4-triazol-1-yl)ethyl]amino]-9H-purin-9-yl]-N-ethyl-β-D-ribofuranuronamide using 1-(2-aminoethyl)-1,2,4-triazole[1] (prepared by basification of the dihydrobromide) as the nucleophile as in entry 10 in Table 5 below. The product was purified by preparative HPLC (29 to 51% acetonitrile). The product had MH$^+$=599, nmr(δ,DMSO-d6) includes 1.00(t, 3H), 3.10–3.20(m,2H), 5.85(d,1H), 6.80–6.95(m,1H), 7.10–7.40(m,10H), 8.00(bs,1H), 8.16(m,2H), 8.47(bs,1H).

1. Cuadro, A. M. et al., Synth. Comm. 1991, 21(4), 535–544.

11) 1-deoxy-1-[2-[[(5-amino-1H-tetrazol-1-yl)ethyl]amino]-6-[(2,2-diphenylethyl)amino]-9H-purin-9-yl]-N-ethyl-β-D-ribofuranuronamide using 1-(2-aminoethyl)-5-amino-1H-tetrazole (prepared by basification of the dihydrobromide) as the nucleophile as in entry 11 in Table 5 below. The product was purified by preparative HPLC (40 to 60% acetonitrile). The product had MH$^+$=615, nmr(δ, DMSO-d6) includes 1.03(t,3H), 3.05–325(m,2H), 4.0–4.3(m,2H), 4.38(bs,1H), 4.45–4.6(m,1H), 4.55–4.75(m, 2H), 5.87(d,1H), 7.1–7.4(m,10H), 8.3(bs,1H).

12) (trans)-1-deoxy-1-[2-[(4-N,N-dimethylaminocyclohexyl)amino]-6-[(2,2-diphenylethyl)amino]-9H-purin-9-yl]-N-ethyl-β-D-ribofuranuronamide using 4-(N,N-dimethylamino)cyclohexylamine as the nucleophile as in entry 12 in Table 5 below. The product was purified by column chromatography on silica eluted with dichloromethane:ethanol:0.88 ammonia (30:8:1) then preparative HPLC (30 to 70% acetonitrile). The product had MH$^+$=629, nmr(δ, DMSO-d6) includes 1.0(t,3H), 1.2–1.6(m,4H), 1.95–2.25(m,4H), 2.75(s,6H), 3.05–3.3(m, 3H), 3.6–3.85(m,1H), 4.0–4.15(m,2H), 4.15–4.25(m,1H), 4.3(s, 1H), 4.4–4.75(m,2H), 5.85(d,1H), 7.15–7.45(m,10H), 8.2(bs,1H), 9.5(m,1H).

13) 1-deoxy-1-[2-[[(4-amino-pyrimidin-5-yl)methyl]amino]-6-[(2,2-diphenylethyl)amino]-9H-purin-9-yl]-N-ethyl-β-D-ribofuranuronamide using 4-amino-5-aminomethyl-pyrimidine[1] as the nucleophile as in entry 13 in Table 5 below. The product was purified by column chromatography on silica eluted with dichloromethane:ethanol:0.88 ammonia (30:8:1) then preparative HPLC (20 to 60% acetonitrile). The product had MH$^+$=611, nmr(δ,DMSO-d6) includes 1.0(t,3H), 3.05–3.25(m,2H), 4.17(m,1H), 4.3(s, 1H), 4.35–4.45(m,1H), 4.45–4.6(m,2H), 5.85(d,1H), 7.0–7.4(m,10H), 8.05–8.2(3H), 8.7(s,1H).

1. Neef, H., Kohnert, K. D., Schellenberger, A, J. Prakt. Chem., 1973, 315(4), 701.

14) 1-deoxy-1-[6-[(2,2-diphenylethyl)amino]-2-[[2-(2-methyl-1H-imidazol-4-yl)ethyl]amino]-9H-purin-9-yl]-N-ethyl-β-D-ribofuranuronamide using 2-(2-methyl-1H-imidazol-4-yl)ethylamine[1] as the nucleophile as in entry 14 in Table 5 below. The product was purified by preparative HPLC (25 to 46% acetonitrile over 11.5 min.). The product had MH$^+$=612, nmr(δ,DMSO-d6) includes 1.0(3H), 2.85–3.0(m,2H), 3.1–3.25(m,2H), 3.5–3.7(m,2H), 4.0–4.15(m,2H), 4.15–4.25(m,1H), 4.3(s,1H), 5.82(d,1H), 6.8–7.05(m,1H), 7.1–7.4(m,10H), 7.8–8.0(m,1H), 8.1–8.3(m,2H), 13.7–13.8(bs,1H), 13.85–14.0(bs,1H).

1. Dziuron, P. and Schunack, W. Eur. J. Med. Chem.-Chimica Therapeutica. 1975, 10(2) 129.

TABLE 5

| Entry | 2-chloropurine g. | nucleophile g. | DMSO ml | temp. °C. | reaction time |
|---|---|---|---|---|---|
| 1 | 0.253 | 0.6(HCl salt) | 2.0 | 130 | 24 h |
| 2 | 0.250 | 0.439(HCl salt) | 1.0 | 130 | 20 h |
| 3 | 0.203 | 0.45(HCl salt) | 1.5 | 130 | 25 h |
| 4 | 0.117 | 0.230(HCl salt) | 1.0 | 120 | 24 h |
| 5 | 0.250 | 0.655(HBr salt) | 0.5 | 130 | 19 h |
| 6 | 0.254 | 0.3 | 2.0 | 120 | 24 h |
| 7 | 0.250 | 0.292 | 1.0 | 130 | 22 h |
| 8 | 0.200 | 0.154 ml | 1.0 | 125 | 20 h |

TABLE 5-continued

| Entry | 2-chloropurine g. | nucleophile g. | DMSO ml | temp. °C. | reaction time |
|---|---|---|---|---|---|
| 9 | 0.200 | 0.318(HCl salt) | 1.0 | 130 | 20 h |
| 10 | 0.250 | 0.655(HBr salt) | 0.5 | 130 | 42 h |
| 11 | 0.171 | 0.209 | 0.7 | 120 | 24 h |
| 12 | 0.368 | 0.5 | 1.5 | 145 | 16 h |
| 13 | 0.275 | 1.0 | 2.0 | 120 | 20 h |
| 14 | 0.350 | 0.42 | 1.5 | 130 | 16.5 h |

Example 42

1-Deoxy-1-[2-[[2-[(aminoiminomethyl)amino]ethyl] amino]-6-[(2,2-diphenylethyl)amino]-9H-purin-9-yl] -N-ethyl-β-D-ribofuranuronamide A solution of 1-[2-chloro-6-[(2,2-diphenylethyl)amino]-9H-purin-9-yl]-1-deoxy-N-ethyl-β-D-ribofuranuronamide (0.382 g, 0.73 mmol) in dimethylsulphoxide (2.5 ml) was heated at 125° for 18 h with ethylenediamine (1.15 g, 19.2 mmol) under nitrogen. The cooled mixture was partitioned between ethyl acetate (50 ml) and water (50 ml) and the aqueous phase was separated, extracted with ethyl acetate (20 ml) and the extract was combined with the organic phase from the partitioning. The organic solution was dried (MgSO$_4$) and evaporated to leave a brown froth (0.373 g). This froth (0.353 g) was dissolved in 50% aqueous methanol (20 ml) and the solution was heated at 50° with pyrazole-1-carboxamidine hydrochloride (0.099 g, 0.675 mmol) for 18 h. More pyrazole-1-carboxamidine hydrochloride (0.099 g, 0.675 mmol) and imidazole (0.048 g, 0.705 mmol) were added and the reaction was heated at 50° for a further 18 h. The mixture was evaporated to leave a red oil which was purified by preparative HPLC (20–60% acetonitrile) to give the title compound (0.23 g) as a solid from ether. The product had MH$^+$=589, nmr(δ,DMSO-d6) includes 1.02(t, 3H), 3.05–3.25(m,2H) 3.3–3.5(m,2H), 3.4–3.6(m,1H), 4.8 (s,1H), 4.5–4.7(m,2H), 5.85(d,1H), 7.15–7.4(m,10H), 7.57 (m,1H), 8.12(s,1H), 8.1–8.25(m,1H).

Example 43

1-Deoxy-1-[2-[[2-[(aminoiminomethyl)amino]ethyl] amino]-6-[(2,2-diphenylethyl)amino]-9H-purin-9-yl] -N-ethyl-β-D-ribofuranuronamide A solution of 1-[2-chloro-6-[(2,2-diphenylethyl)amino]-9H-purin-9-yl]-1-deoxy-N-ethyl-β-D-ribofuranuronamide (0.310, 0.592 mmol) in dimethylsulphoxide (2 ml) was heated with 1,3-diaminopropane (0.542 g, 7.31 mmol) at 1200 for 24 h. The cooled mixture was partitioned between ethyl acetate (50 ml) and water (50 ml) and the aqueous phase was separated and extracted with ethyl acetate (20 ml). The combined ethyl acetate solution was washed with water (20 ml), dried (MgSO$_4$) and evaporated to leave a froth (0.302 g). This froth (0.3 g)was dissolved in 50% aqueous methanol (20 ml) and the solution was heated at reflux with pyrazole-1-carboxamidine hydrochloride (0.099 g, 0.675 mmol) and imidazole (0.05 g, 0.734 mmol) for 18 h. More pyrazole-1-carboxamidine hydrochloride (0.099 g, 0.675 mmol) was added and heating was continued for a further 24 h. The mixture was evaporated to leave a solid which was purified by preparative HPLC (20–60% acetonitrile) to give the title compound (0.202 g) as a solid from ether. The product had MH$^+$=603, nmr(δ,DMSO-d6) includes 1.02(t,3H), 1.7–1.9(m,2H), 3.05–3.25(m,4H), 3.3–3.5(m,2H), 4.15–4.25(m,1H), 4.8(s,1H), 4.5–4.7(m, 2H), 5.85(d,1H), 7.15–7.4(m,10H), 7.5–7.65(m,1H), 8.12(s, 1H), 8.1–8.25(m,1H).

Example 44

The effects of compounds of the invention on fMLP activation of O$_2^-$ generation The potential for compounds of formula (I) to inhibit leukocyte function was examined by measuring the ability of the compounds to inhibit superoxide (O$_2^-$) generation from neutrophils stimulated with fMLP following the procedure described by W. Busse et al. in J. Allergy Clin. Immunology, 83(2) Part 1, 400–405 (1989). In this test the deprotected compounds of the specific examples were shown to inhibit O$_2^-$ generation. Thus, for example, compounds of Examples 2, 5, 7, 10, 12, 14, 15, 19, 21, 21(3), 21(4), 21(5), 21(6), 21(7), 21(8), 21(11), 21(12), 21(13), 21(14), 21(15), 21(16), 21(21), 21(22), 21(23), 21(25), 21(26), 21(31), 21(36), 21(37), 27, 27(2), 29, 31, 31(1), 33, 33(3), 34(1), 41, 41(2), 41(4), 41(9), 41(12), 41(14), 42 and 43 were at least as active as NECA in this study. Indeed, the compound of Example 33 is 25 times more potent than NECA in this study.

Antigen-induced lung eosinophil accumulation in sensitised guinea pigs

Ovalbumin-sensitised guinea pigs were dosed with mepyramine (1 mg/kg ip) to protect against anaphylactic bronchospasm. A compound of the invention was then given ip 30 minutes before ovalbumin challenge (30 minutes breathing of an aerosol generated from a 50 μg/ml solution of ovalbumin). A second dose of test compound was administered 6 hours after the first dose. Twenty-four hours after challenge, the guinea pigs were killed and bronchoalveolar lavage performed. Total and differential cell counts were then made and the dose of test compound giving a 50% reduction of cell accumulation (ED$_{50}$) was calculated.

Results

In the above test, the compound of Example 33 has an average ED$_{50}$ of 10 μg/kg.

Administration of the compound of Example 33 to guinea pigs ip produced no visible toxic effects at single doses up to 100 μg/kg.

The following are examples of suitable formulations of compounds of the invention. The term "active ingredient" is used herein to represent a compound of the invention and can be, for example, the compound of Example 33.

1. Injection for Intravenous Administration

|  | mg/ml |
|---|---|
| Active Ingredient | 0.5 mg |
| Sodium Chloride BP | as required |
| Water for Injection BP  to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

2. Inhalation Cartridges

|  | mg/cartridge |
|---|---|
| Active ingredient micronised | 0.200 |
| Lactose BP    to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

3. Metered Dose Pressurised Aerosol

A. Suspension Aerosol

|  | mg/metered dose | per can |
|---|---|---|
| Active ingredient micronised | 0.100 | 26.40 mg |
| Oleic Acid BP | 0.010 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The Oleic Acid is mixed with the Trichlorofluoromethane at a temperature of 10°–15° C. and the micronised drug is mixed into the solution with a high shear mixer. The suspension is metered into aluminium aerosol cans and suitable metering valves, delivering 85 mg of suspension, are crimped onto the cans and the Dichlorodifluoromethane is pressure filled into the cans through the valves.

B. Solution Aerosol

|  | mg/metered dose | per can |
|---|---|---|
| Active ingredient | 0.100 | 24.0 mg |
| Ethanol BP | 7.500 | 1.80 mg |
| Trichlorofluoromethane BP | 18.875 | 4.53 g |
| Dichlorodifluoromethane BP | 48.525 | 11.65 g |

Oleic acid BP, or a suitable surfactant, e.g. Span 85 (sorbitan trioleate) may also be included.

The active ingredient is dissolved in the ethanol together with the oleic acid or surfactant if used. The alcoholic solution is metered into suitable aerosol containers followed by the trichlorofluoromethane. Suitable metering valves are crimped onto the containers and dichlorodifluoromethane is pressure filled into them through the valves.

C. Alternative Suspension Aerosol

|  | mg/metered dose | per can |
|---|---|---|
| Active ingredient | 0.100 | 24.0 mg |
| 1,1,1,2-tetrafluoroethane | 75.0 | 18.0 g |

Oleic acid BP or a suitable surfactant may also be included.

The active ingredient is dispersed in the propellant held as a liquid at high pressure and/or low temperature. The resulting dispersion is then metered into suitable containers either at low temperatures prior to crimping a metering valve or by pressure filling through a pre-crimped metering valve.

We claim:

1. A compound of formula (IV):

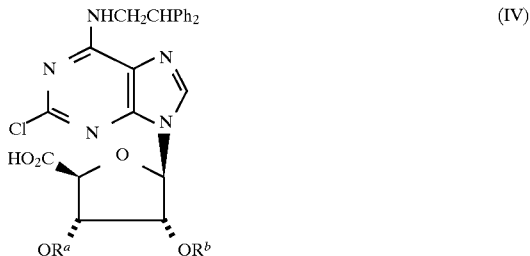

wherein $R^a$ and $R^b$ each represent a hydrogen atom or together form an alkylidene group.

2. A compound of formula (IV) according to claim 1 wherein $R^a$ and $R^b$ each represent a hydrogen atom.

3. A compound of formula (IV) according to claim 1 wherein $R^a$ and $R^b$ together form an isopropylidene group.

* * * * *